United States Patent [19]

Fujiwara et al.

[11] Patent Number: 5,252,493
[45] Date of Patent: Oct. 12, 1993

[54] LASER MAGNETIC IMMUNOASSAY METHOD AND APPARATUS THEREFOR

[75] Inventors: Koichi Fujiwara; Juichi Noda, both of Mito; Hiromichi Mizutani; Hiroko Mizutani, both of Tokyo, all of Japan

[73] Assignee: Nippon Telegraph and Telephone Corporation, Tokyo, Japan

[21] Appl. No.: 221,248

[22] PCT Filed: Sep. 22, 1987

[86] PCT No.: PCT/JP87/00694

§ 371 Date: Jul. 22, 1988

§ 102(e) Date: Jul. 22, 1988

[87] PCT Pub. No.: WO88/02118

PCT Pub. Date: Mar. 24, 1988

[30] Foreign Application Priority Data

| | | | |
|---|---|---|---|
| Sep. 22, 1986 | [JP] | Japan | 61-224567 |
| Oct. 23, 1986 | [JP] | Japan | 61-252427 |
| Oct. 25, 1986 | [JP] | Japan | 61-254164 |
| Feb. 2, 1987 | [JP] | Japan | 62-22062 |
| Feb. 2, 1987 | [JP] | Japan | 62-22063 |
| Jun. 19, 1987 | [JP] | Japan | 62-152791 |
| Jun. 19, 1987 | [JP] | Japan | 62-152792 |
| Jul. 24, 1987 | [JP] | Japan | 62-184902 |

[51] Int. Cl.$^5$ ............................................. G01N 33/553
[52] U.S. Cl. ........................................ 436/526; 435/5; 435/291; 422/73; 422/82.05; 356/337
[58] Field of Search ................. 435/2, 4, 5, 7, 173, 435/174, 176–181, 287, 291, 296, 297–300, 311, 316, 803, 808; 436/518, 526, 532, 538, 543, 544, 547, 164, 166, 174, 177, 805, 806, 807, 809, 810, 824; 422/68, 73, 101, 102, 82.05; 210/695, 222; 209/213–215, 217, 223.1, 223.2, 225–228, 8, 39; 356/36, 337–343, 351, 364, 365, 369, 426–428, 246; 220/505

[56] References Cited

U.S. PATENT DOCUMENTS

| | | | |
|---|---|---|---|
| 849,165 | 4/1907 | Schneider | 220/505 |
| 3,933,997 | 1/1976 | Hersh et al. | 424/1 |
| 3,970,518 | 7/1976 | Giaever | 209/8 |
| 3,990,851 | 11/1976 | Gross et al. | |
| 4,001,583 | 1/1977 | Barrett | 436/532 |

(List continued on next page.)

FOREIGN PATENT DOCUMENTS

| | | | |
|---|---|---|---|
| 0030087 | 6/1981 | European Pat. Off. | 436/526 |
| 0177988 | 4/1986 | European Pat. Off. | |
| 0194156 | 9/1986 | European Pat. Off. | |
| 1128168 | 6/1986 | Japan. | |
| 62-104066 | 4/1987 | Japan. | |
| 62-137988 | 6/1987 | Japan. | |
| WO86/04684 | 8/1986 | PCT Int'l Appl. | |

OTHER PUBLICATIONS

Gruetzmacher et al. "Magnetic Immunoassay: A Heterogeneous Immunoassay Based on the Detection of Magnetic Particles." Clinical Chemistry, vol. 29, No. 6 (1983), p. 1252.

Primary Examiner—Michael G. Wityshyn
Assistant Examiner—William H. Beisner
Attorney, Agent, or Firm—Frishauf, Holtz, Goodman & Woodward

[57] ABSTRACT

An ultra-sensitive laser magnetic immunoassay method comprising the steps of: labeling an antigen or antibody with micro-particles of a magnetic substance to form a magnetic-labeled body; subjecting a specimen and the magnetic-labeled body to an antigen-antibody reaction to form a reacted body-specimen complex; separating and removing unreacted body from the reacted complex; guiding and concentrating the reacted complex magnetically; irradiating the concentrated complex with a laser beam; detecting outgoing light from a measurement system to provide a quantitative result in the picogram range. An apparatus comprising a specimen container for storing a specimen labeled with magnetic micro-particles, concentration means for guiding and locally concentrating the specimen, a laser beam irradiating optical system for guiding a laser beam into the specimen, and a light receiving system arranged so as to detect outgoing beams from the specimen.

7 Claims, 46 Drawing Sheets

U.S. PATENT DOCUMENTS

| | | | |
|---|---|---|---|
| 4,018,886 | 4/1977 | Giaever | 210/222 |
| 4,115,535 | 9/1978 | Giaever | 436/526 |
| 4,152,210 | 5/1979 | Robinson et al. | 435/173 |
| 4,171,956 | 10/1979 | Uzgiris | |
| 4,219,335 | 8/1980 | Ebersole | 422/69 |
| 4,272,510 | 6/1981 | Smith et al. | 436/526 |
| 4,313,734 | 2/1982 | Leuvering | 422/61 |
| 4,446,239 | 5/1984 | Tsuji et al. | 422/73 |
| 4,452,773 | 6/1984 | Molday | 436/526 |
| 4,537,861 | 8/1985 | Elings et al. | 436/526 |
| 4,605,305 | 8/1986 | Lenoir et al. | 356/246 |
| 4,725,140 | 2/1988 | Musha | 356/364 |
| 4,741,619 | 5/1988 | Hummahries et al. | 422/102 |
| 4,762,413 | 8/1988 | Namba et al. | 422/73 |
| 4,784,954 | 11/1988 | Zimmermann | 435/173 |
| 4,859,612 | 8/1989 | Cole et al. | 436/523 |
| 4,990,075 | 2/1991 | Wogoman | 422/58 |

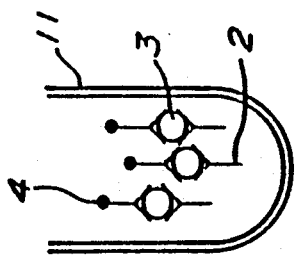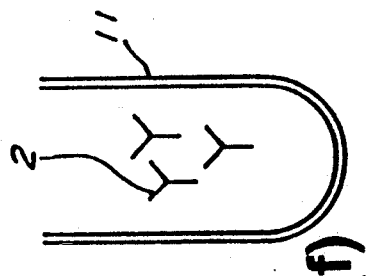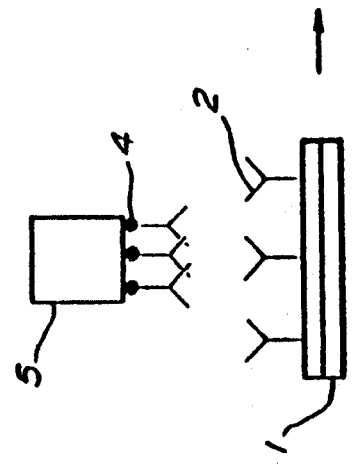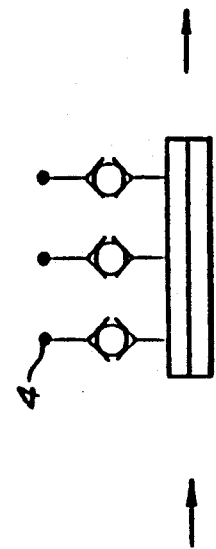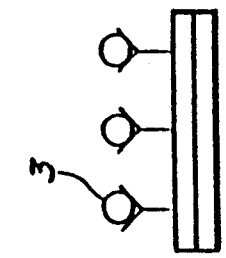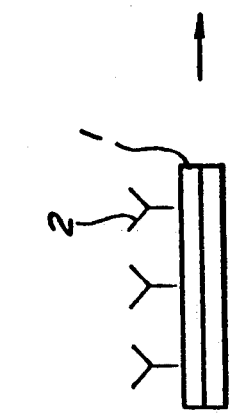

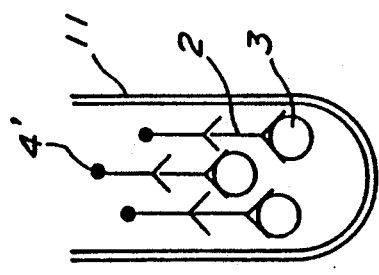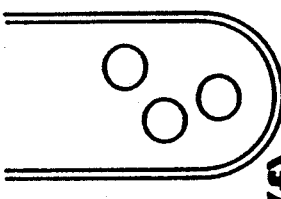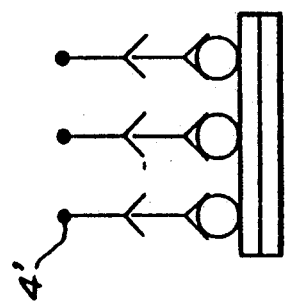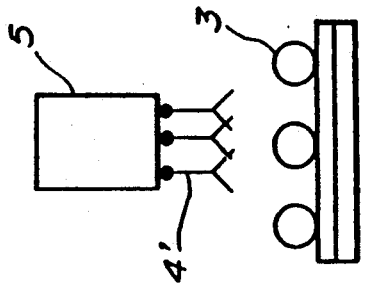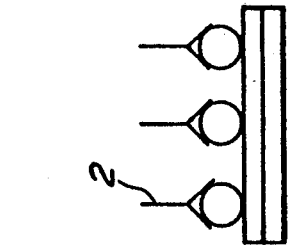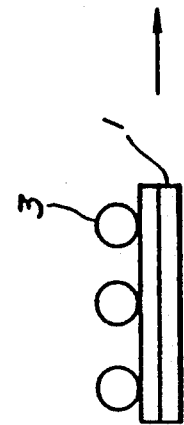

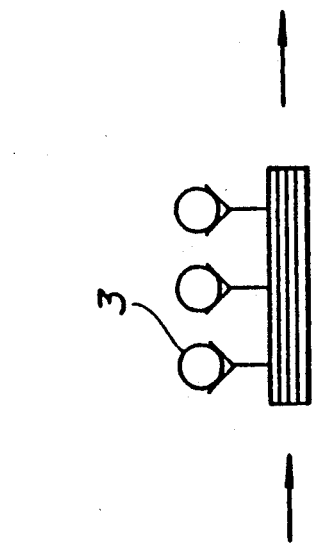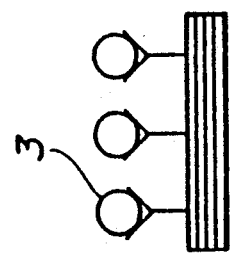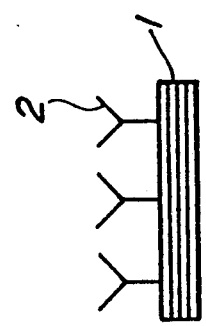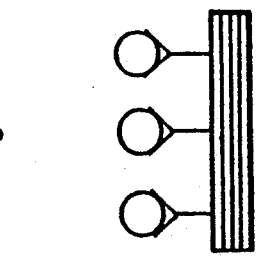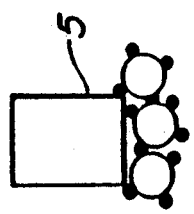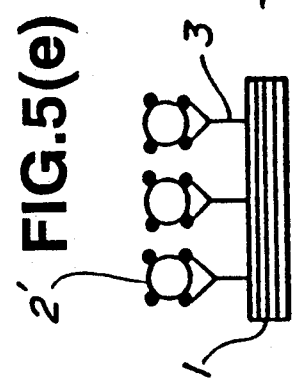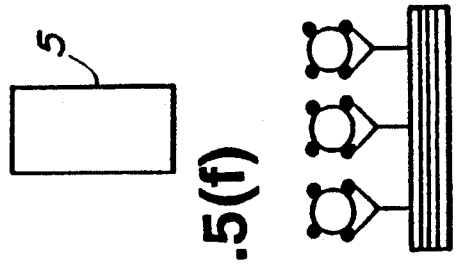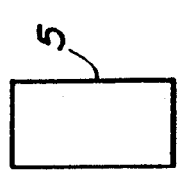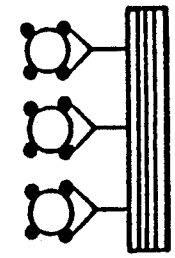
FIG.5(a) FIG.5(b) FIG.5(c) FIG.5(d) FIG.5(e) FIG.5(f)

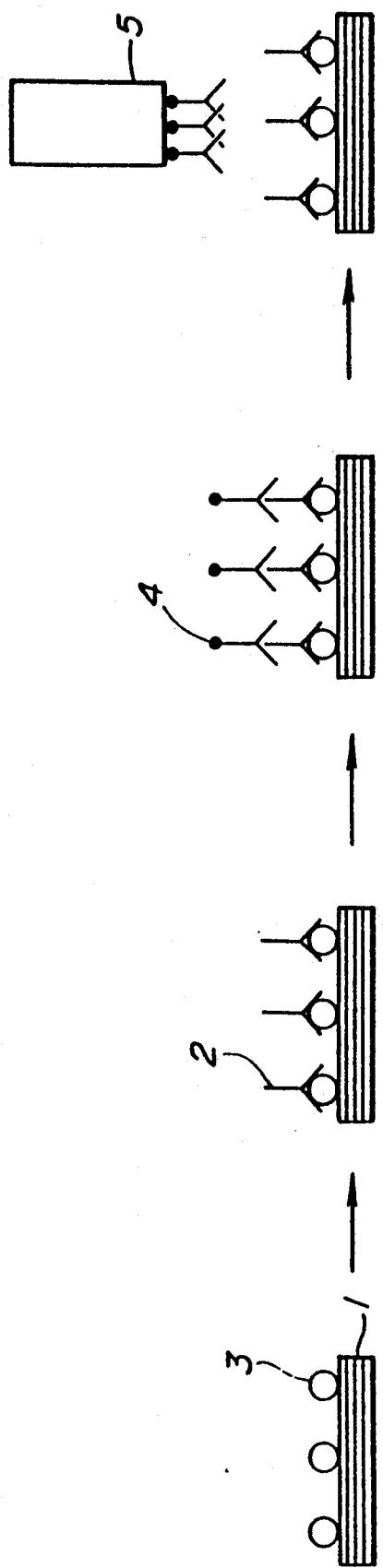
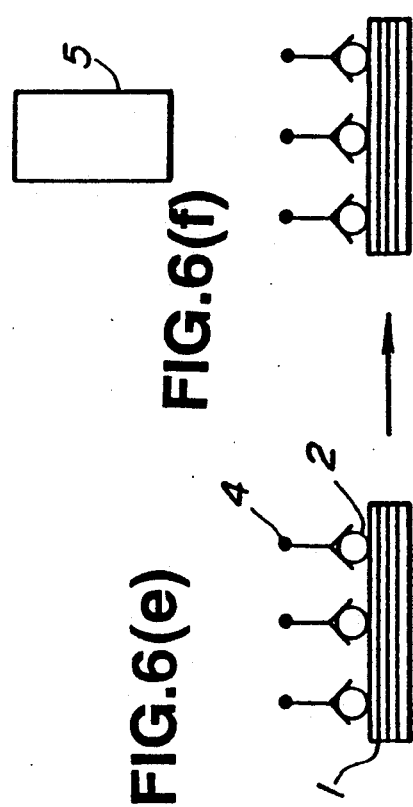

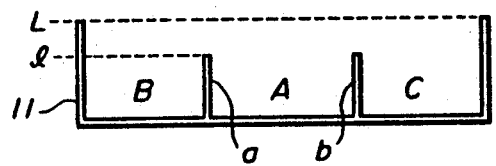
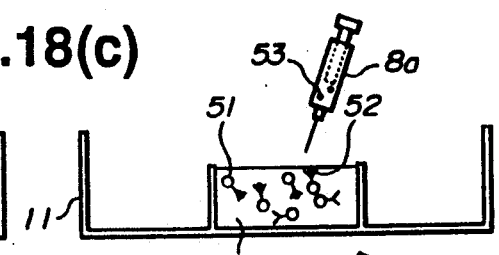
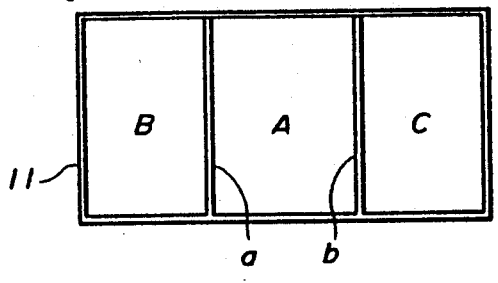
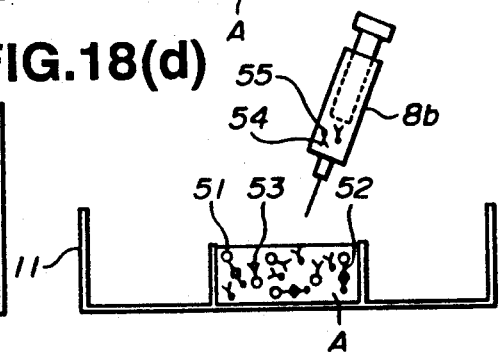
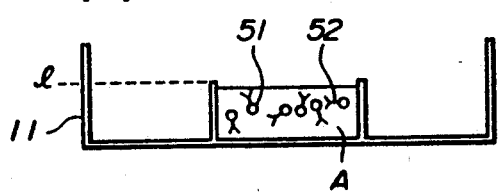
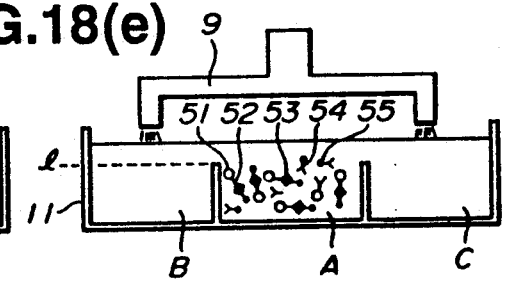

FIG.18(f)
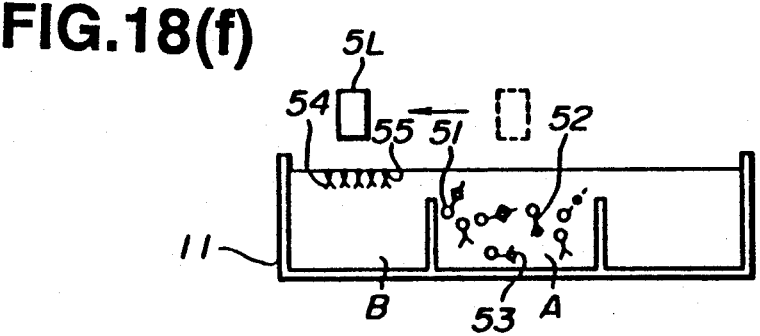
FIG.18(f')
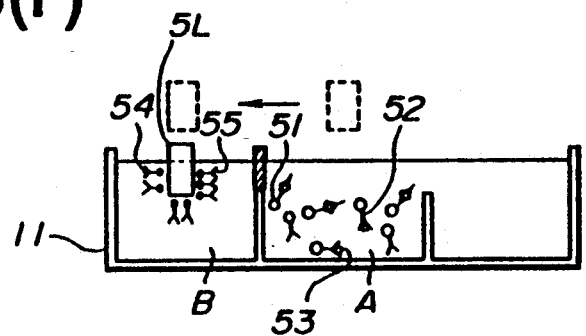
FIG.18(g)
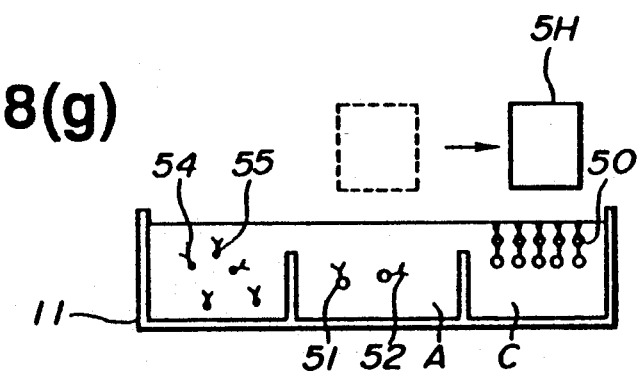
FIG.18(h)
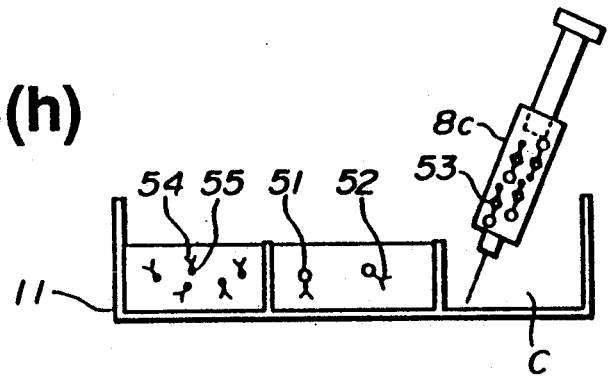

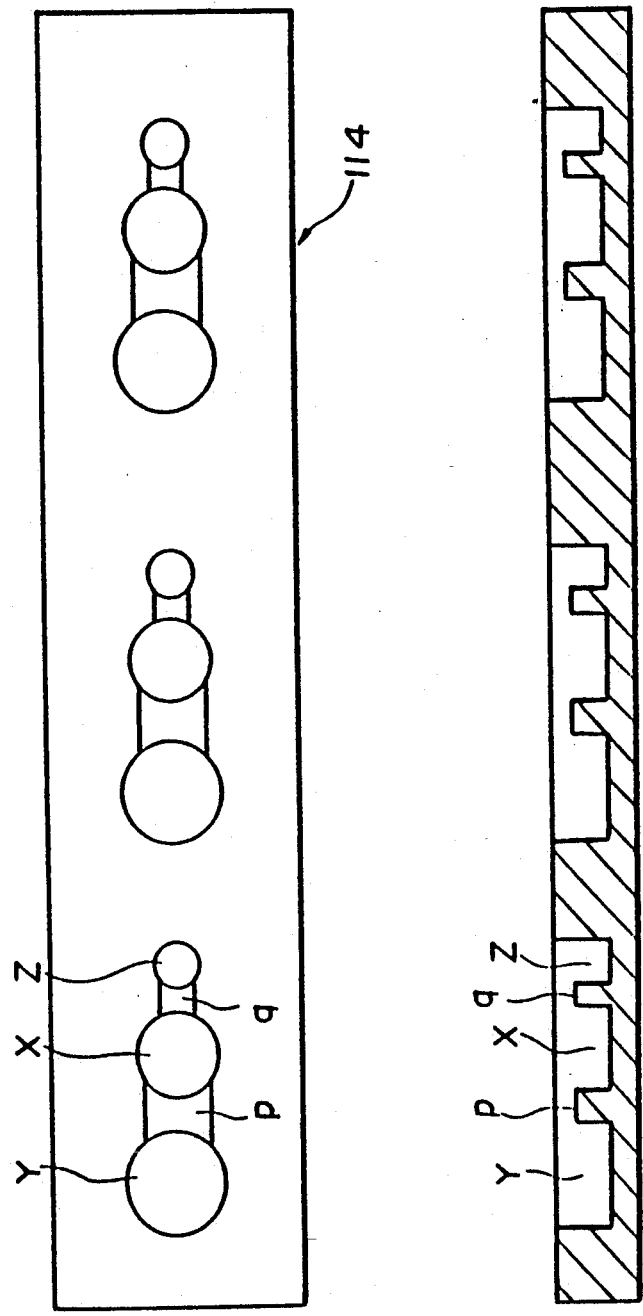

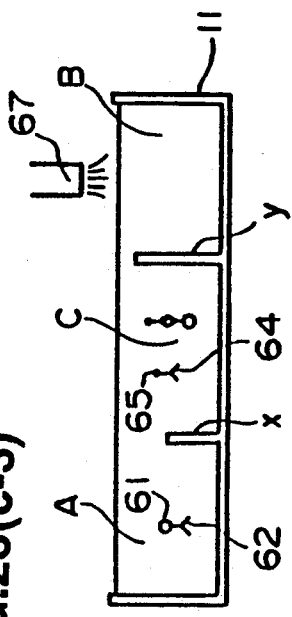
FIG.23(c-0)
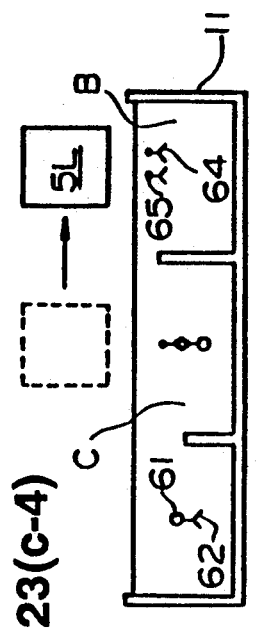
FIG.23(c-1)
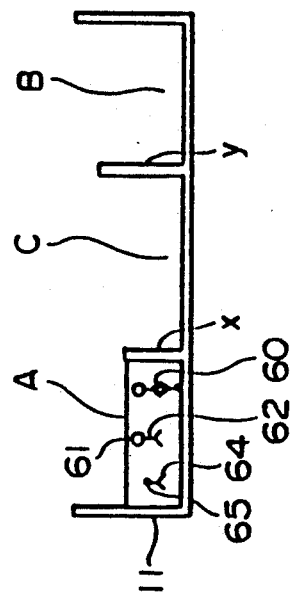
FIG.23(c-2)
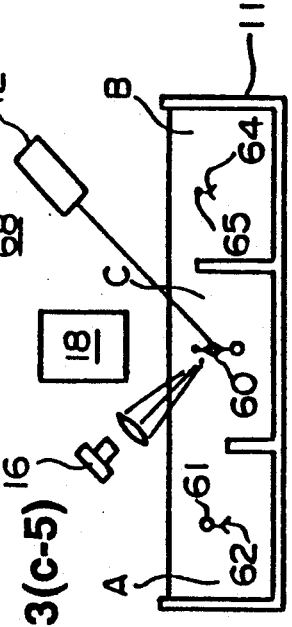
FIG.23(c-3)
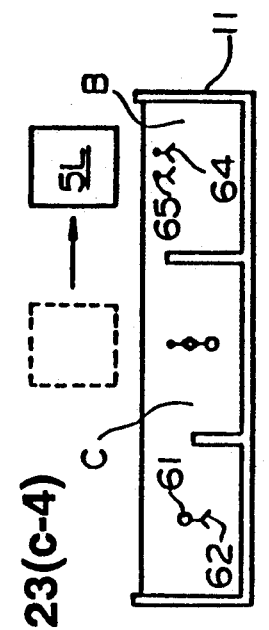
FIG.23(c-4)
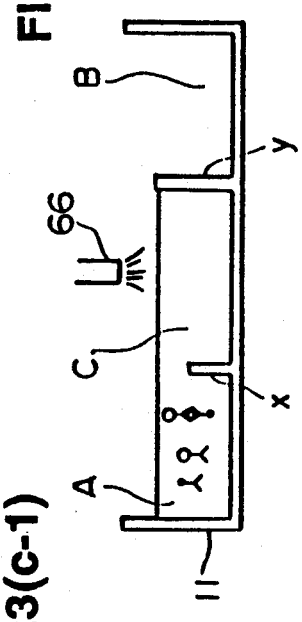
FIG.23(c-5)

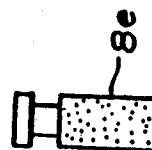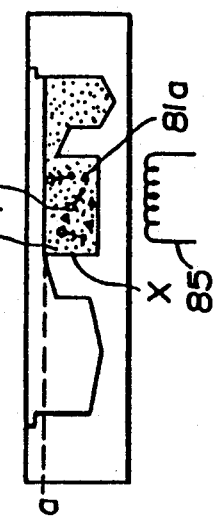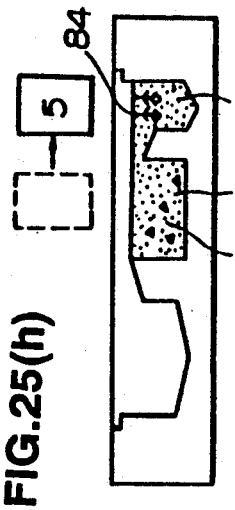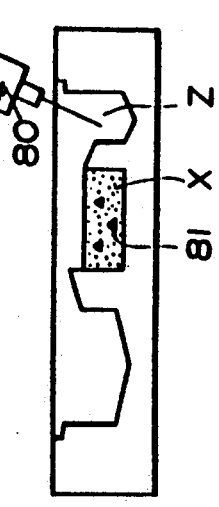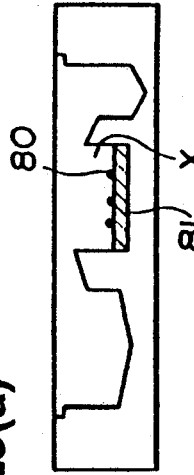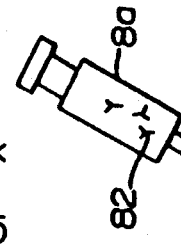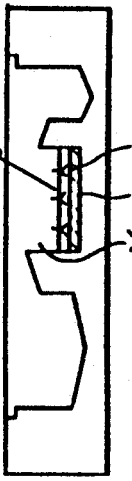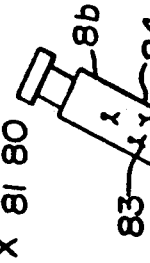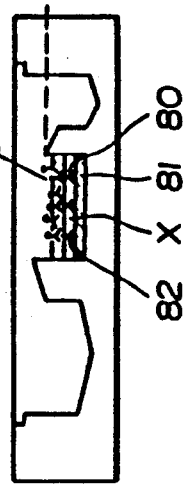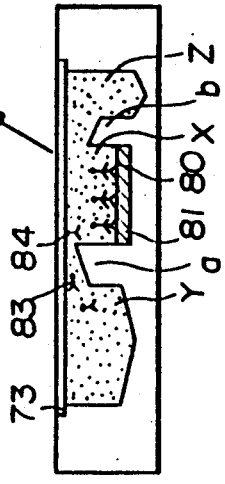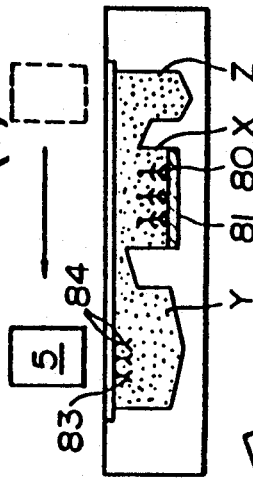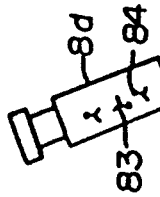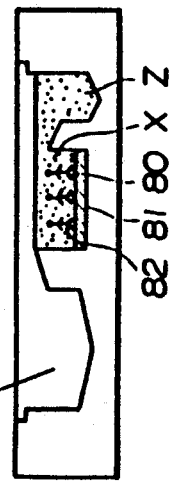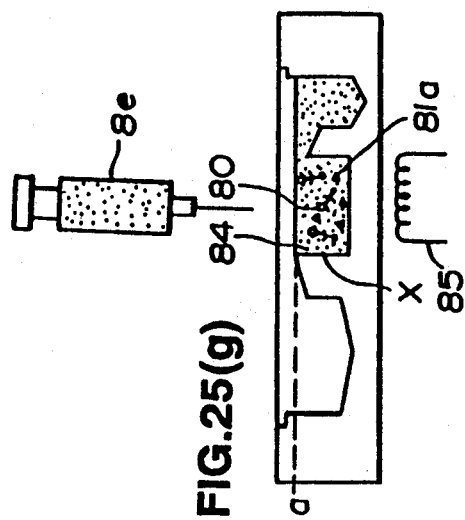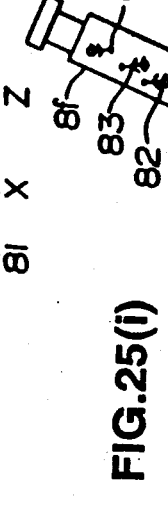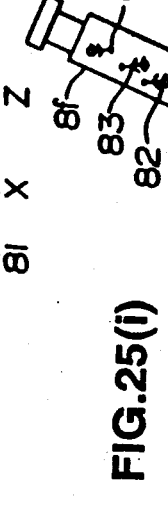

INTERMITTENT PULSATE POWER SOURCE

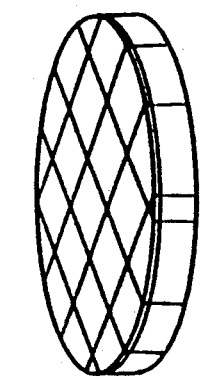
FIG.40(a)
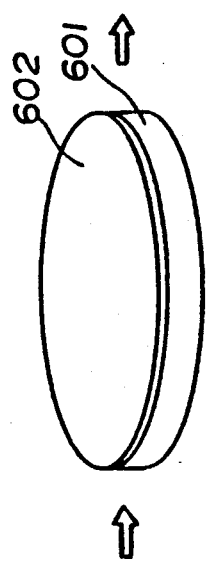
FIG.40(b)
FIG.40(c)
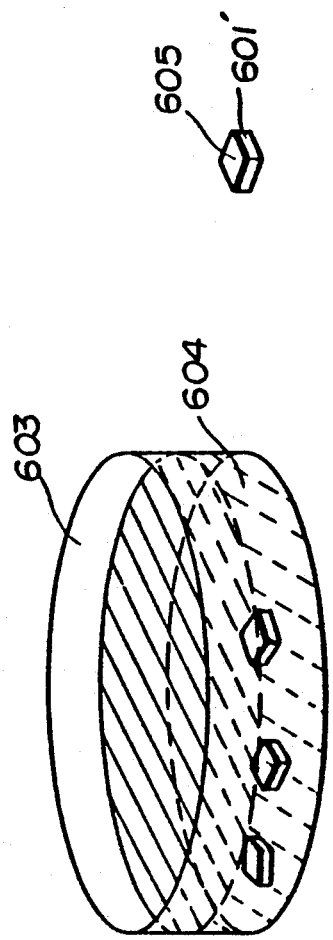
FIG.40(d)
FIG.40(e)

LASER MAGNETIC IMMUNOASSAY METHOD AND APPARATUS THEREFOR

TECHNICAL FIELD

The present invention relates to a laser magnetic immunoassay method utilizing an antigen-antibody reaction and apparatus therefor. More particularly, the present invention relates to a laser magnetic immunoassay method which is capable of detecting a specific antibody or antigen in a very small amount of a specimen.

BACKGROUND ART

Development of immunoassay methods utilizing an antigen-antibody reaction is now being made on a global scale as an early detection method for new virus-based diseases such as AIDS and adult T-cell leukemia as well as various cancers. The methods are designed to detect an antibody or antigen itself utilizing the property of an antibody, which is prepared when virus or a like serving as an antigen has invaded into a living organism, to specifically react with the corresponding antigen (antigen-antibody reaction). As a micro-immunoassay method for this purpose, RIA (radioimmunoassay), EIA (enzyme-immunoassay), FIA (fluorescence-immunoassay), etc. have heretofore been used in practice. These methods use antigens or antibodies which are labeled with an isotope, an enzyme or a fluorescent substance in order to detect the presence of the corresponding antibodies or antigens, respectively, that react therewith.

Among them, RIA is to quantitatively determine the amount of the specimen which contributed to the antigen-antibody reaction by measuring the amount of the radio-activity of the isotope fixed for labeling. To date, only this method is capable of ultramicro measurement in the order of picogram. However, RIA needs special installment since it has to handle radioactive substances and there have heretofore been restrictions with respect to time and place for use and the like in view of the half-life period of the radioactive substances, disposal of wastes and the like. In addition, those methods which use enzymes or fluorescent substances are designed to confirm if the presence of antigen-antibody reactions and therefore they remain semi-quantitative and the detectability limit is in the order of nanogram. Therefore, it has been a demand for an immunoassay method which has a detection sensitivity in the same order as that of RIA but is free of restrictions when in use.

Examples of thus-far published methods in which a laser beam is used to detect the presence of antigen-antibody reaction include a method designed for detecting liver cancer, in which micro-particles of a plastic are provided with an antibody to AFP (alpha-faeto protein) and the change in the mass as the result of agglomeration between the plastic particles due to antigen-antibody reaction is monitored by the change in the scattering or transmission of a laser beam. Reportedly, the detection sensitivity of this method is $10^{-10}$ g, which is one hundred times higher than conventional laser methods, but still one hundred times less sensitive as that of RIA. Since the method utilizes the change in Brownian movement of antigens and antibodies in an aqueous solution, it is necessary to precisely control the temperature of the aqueous solution containing a specimen upon measurement, and the method is defective in that it is susceptible to influences from outside such as ambient temperature and vibration.

Also, there is an essential limitation in the improvement of the detection sensitivity of the conventional laser beam scattering measurement and a large amount of specimen is required since only a part of the aqueous solution in which the specimen is dispersed is irradiated. One approach proposed for obviating this defect is to use as a vessel capillary tubes having the same diameter as that of a laser beam in the laser beam scattering measurement with view to reducing time for measurement and minimizing the amount of a specimen used (U.S. Pat. No. 4,605,305). However, there is a problem in that the detection sensitivity is decreased due to disturbance of measurement by the scattered light from the walls of the capillary tubes.

Further, magnetic micro-particles are used in an attempt to facilitate the adjustment of a specimen. More particularly, magnetic micro-particles are used in the removal or separation of various components in liquid samples. For example, U.S. Pat. No. 4,018,886 and 3,970,518 disclose methods in which magnetic micro-particles are used to collect a specified protein, the protein is cut off from the magnetic micro-particles and the precipitate obtained is observed with one's eyes. Also, U.S. Pat. No. 3,933,997 discloses a method in which a radioactive label is concentrated onto a specimen using magnetic micro-particles. In addition, methods prevail in which magnetic micro-particles bearing a receptor capable of being specifically bound to a specimen, and a label substance are used to separate unused label substances (enzymes, radioactive substances, fluorescent substances, etc.) using magnetic force (WO86/04684 and EP-A-30087). However, although some improvement in the degree or accuracy of separation is observed, the overall degree of separation is unsatisfactory since measurement itself is made according to conventional method and is controlled by the accuracy of the method used.

Further, U.S. Pat. No. 4,219,335 uses the above-described magnetic micro-particles in order to magnetically check the presence of a specified specimen in a body fluid. More particularly, a body fluid sample is affixed to the surface of the particles coated with a receptor reagent having a specific reactivity to the specimen, and upon contacting with the surface an immunoreagent which has a reactivity with the receptor reagent or a complex of the receptor reagent and the specimen, a substance labeled with a reactance label such as micro-particles of a magnetic substance is used as an immuno-reagent, which is applied to the surface of a suspension of the specimen, and then, the change in the electrical reactance such as dielectric constant, conductivity or magnetic permeability of the surface is measured after removing unused immuno-reagent from the surface. This method, in which a measurement is made in order to directly check the presence or abundance of labeled micro-particles, is different at all in its principle from methods in which a laser beam is radiated into a measurement system including an immunocomplex labeled with micro-particles of the magnetic substance and corresponding outgoing light is optically measured.

The present inventors have previously investigated methods for detecting magnetic-labeled specimen using a magnetic head with high sensitivity and applied Japanese Patent Application No. Sho-62-104066 entitled "Detector for magnetic substances" and Japanese Patent Application No. Sho-62-137988 entitled "Magnetic immunoassay and apparatus therefor". However, the detection sensitivity thereof remains in the order of $1 \times 10^{-9}$ g, which is by thousands times as sensitive as that of the laser magnetic immunoassay according to the present invention even when these methods of improving the detection sensitivity invented by the present inventors are applied.

DISCLOSURE OF THE INVENTION

As a result of intensive investigation by the present inventors, it has now been found that various restrictions such as half-life period and disposal of wastes can be removed and an immunoassay can be carried out with a detection sensitivity in the order of picogram, which is as sensitive as RIA by labeling an antigen or antibody with micro-particles of a magnetic substance, subjecting the resulting labeled substance and a specimen to an antigen-antibody reaction, guiding the resulting labeled immuno-complex to a measurement position after removing it from an unused labeled substance, and optically measuring the presence or abundance of the complex, thus completing the present invention.

That is, the present invention provides a laser magnetic immunoassay which comprises a step of labeling an antigen or antibody with micro-particles of a magnetic substance to obtain a magnetic-labeled body and subjecting the magnetic-labeled body and a specimen to an antigen-antibody reaction, a step of removing an unused magnetic-labeled body from a magnetic-labeled body-specimen complex which is a complex of the magnetic-labeled body after the above-described step and the specimen, a step of applying a laser beam, and a step of measuring the outgoing beam from a measurement system containing the magnetic-labeled body-specimen complex obtained in the preceding step.

Further, the present invention provides a laser magnetic immunoassay apparatus comprising a specimen container for storing a specimen labeled with micro-particles of a magnetic substance, a concentrating means for guiding and concentrating the specimen, a laser beam radiating optical system for guiding laser beams into the specimen container and light reception means disposed so as to receive those laser beams scattered by the specimen.

BRIEF DESCRIPTION OF DRAWINGS

FIGS. 2(a) to 2(f), 3(a) to 3(f), 4(a) to 4(d), 5(a) to 5(f), and 6(a) to 6(f) each are a view illustrating a method for preparing a specimen liquid for use in a laser magnetic immunoassay according to the present invention;

FIGS. 18 (a) to 18(h) illustrate preparation of a specimen upon laser magnetic immunoassay according to the present invention, in which FIGS. 18 (a) and 18(a') particularly show the shape of a specimen container used;

FIGS. 21 (b-1) and 21(b-2) illustrate the shape of a specimen container which can be used in the apparatus shown in FIG. 20 (a) with particular advantage, with FIG. 20 (b-1) being a plan view and FIG. 20 (b-2) a cross-sectional view;

FIG. 22 (b) is a graph showing the results of measurement of the change in scattered light which is in synchronization with the waveform shown in FIG. 22(a);

FIG. 23 (b) is a schematical illustration of a layout of an apparatus which can process specimens continuously using the specimen container shown in FIG. 23 (a);

FIGS. 23 (c-0) to 23(c-5) illustrate the operation of the apparatus shown in FIG. 23(b) stage by stage;

FIG. 24 (a) is a plan view, and FIG. 24 (b) a cross-sectional view;

FIGS. 25 (a) to 25(i) illustrate step by step preparation of a specimen for use in the laser magnetic immunoassay carried out using a specimen container according to the present invention;

FIGS. 40(a) to 40(e) are an illustration of a method of immobilizing an antigen or antibody according to the present invention.

BEST MODE FOR CARRYING OUT THE INVENTION

Figure 1:
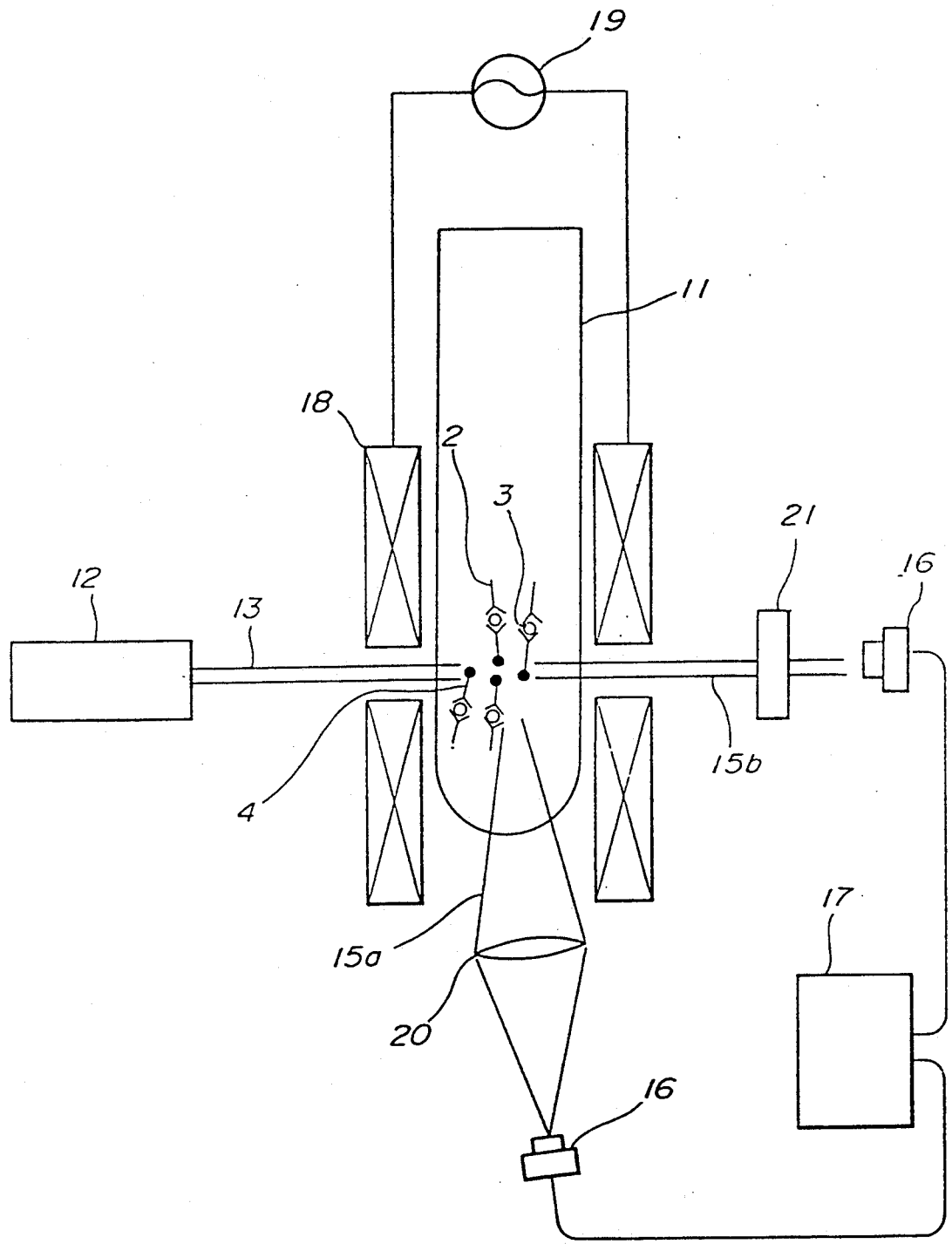
FIG. 1 is a schematical view of an apparatus for measuring outgoing laser beams according to one embodiment of the present invention.
Figure 4A:
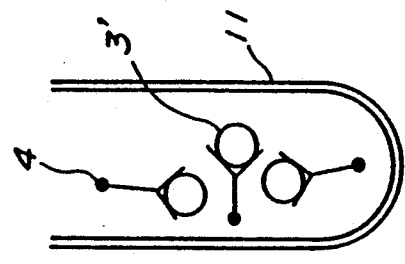
Figure 4B:
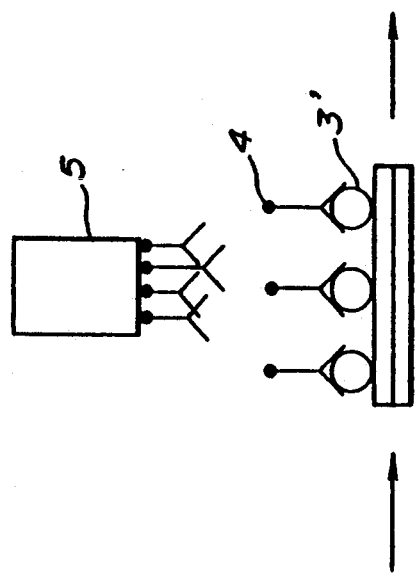
Figure 4C:
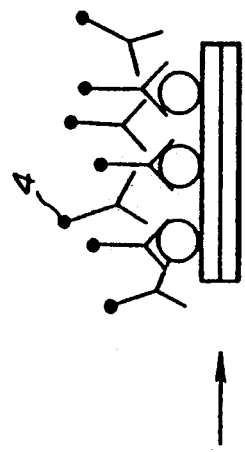
Figure 4D:
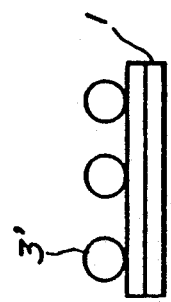

The present invention uses micro-particles of a magnetic substance as a label and attaches the label to a specified or unknown antigen or antibody such as various virus antigens or virus antibodies collected from blood and excreta of patients to prepare a magnetic-labeled body.

The present invention is also applicable to cases where the magnetic-labeled body is used to label, besides virus, antibodies to cancers in the blood of patients or lymphocytes or monoclonal antibodies which recognize corresponding cancers specifically, or cancerated lymphocytes themselves as in the case of leukemia.

Further, compound magnetic substances such as magnetite and $\gamma$-ferrite, and metal magnetic substances such as cobalt can be used as micro-particles of a magnetic substance. In addition thereto, ultramicro-particles of those magnetic substances described at column 3 line 58 to column 4 line 7 of U.S. Pat. 4,219,335 can be used. Among them, magnetite is preferred since it has a good affinity with virus and specific antibodies and therefore it is suitable for labeling virus and the like. Further, in order to carry out removal and separation by means of outer magnetic field and measurement of outgoing beams from a specimen described hereinbelow efficiently and effectively, the magnetite preferably is of a single domain grain structure and suitably has a grain size in the order of 50 nm.

The micro-particles of such magnetic substances can be bound to immunological reactants (antigens or antibodies) by a known method. The micro-particles can be encapsulated with an organic polymer which can bind an immunological reactant thereto or the surface of the micro-particles can be silanated in a known manner followed by binding an organic compound to the silane bond. U.S. Pat. No. 3,954,666 discloses encapsulation of a core material with a polymer, and U.S. Pat. 3,983,299 discloses binding an organic compound to inorganic particles with silane bonds.

Then, an antibody or antigen as a specimen is subjected to an antigen-antibody reaction with a known immobilized antigen or antibody, respectively, or alternatively, an antibody or antigen as a specimen is directly immobilized and subjected to an antigen-antibody reaction with the above-described magnetic-labeled body.

The method of immobilization described above can be carried out using a support made of a non-magnetic substance composed of an inorganic material such as silicon or an organic material such as plastic resin. The support may be tabular or micro-balls of 1 $\mu$m to 1 mm in diameter, or alternatively a specimen container itself may be selected as a support. The support is coated thereon an organic film which is soluble in an organic solvent or an inorganic film and the above-described antigen or antibody is immobilized thereto. The film may be selected from resists which are soluble in methanol or a like for use in, for example, photolithography for the production of semi-conductors, depending on antigen and antibody used. For example, Novolak resin is preferred when influenza virus is to be immobilized to such film.

Further, in addition to the present invention, the method described in Methods in Enzymology, Vol. XLIV, pages 324-326 can be used as a technique of immobilization of enzymes to a magnetic support. For example, agar, gelatin and the like can be used as a support. The present invention is not limited to the above-described binding methods and any other binding methods can be used as far as the ability of the immunological reactant to form immuno-complex is not hindered.

In the present invention, pretreatment in which a specimen and a magnetic-labeled body are reacted includes an indirect method in which a known immobilized antigen or antibody and a corresponding antibody or antigen as a specimen are reacted and a direct method in which an antibody or antigen as a specimen is directly immobilized. Further, the method for reacting the magnetic-labeled body includes a method in which a specimen and a magnetic-labeled body are reacted with each other positively and a method in which the reaction is inhibited (competitive inhibitory reaction detection method).

Thereafter, unused magnetic-labeled body is removed.

The step of separating and, removing unused magnetic-labeled body is different between the case where tabular ones or the bottom surface of the specimen container itself is used as a support and the case where the above-described micro-balls (herein, referred to as non-magnetic balls) are used as a support. When the tabular support or the bottom surface of the specimen container itself is used as a support, the step of removal is carried out using a magnet, for example, a rare earth metal magnet taking advantage of the characteristics of the magnetic-labeled body. However, removal is also possible by washing. Simultaneous use of a magnet and washing is also effective. After the step of removal, in the case of the method of immobilization of the present invention, the bonding between the support and the magnetic-labeled specimen is cut off by dissolving the film out of the support with an organic solvent to fluidize the magnetic-labeled specimen.

When the non-magnetic balls are used as the support, non-magnetic balls floating in a liquid and unused magnetic-labled body can be separated from each other by guiding them using appropriately controlled magnetic force since the non-magnetic balls have size and mass larger than those of the magnetic-labeled body. In order to ensure separation, it is suitable to use a filter which can pass the magnetic-labeled body but not the non-magnetic balls together with the magnetic force. Thus, the specimen to be measured is adjusted.

In the case where the specimen is an antigen or antibody which can be susceptible to a specific antigen-antibody reaction with the magnetic-labeled body, the magnetic-labeled body remains in the liquid phase containing the specimen. In the other cases, the magnetic-labeled body does not remain in the liquid phase. Therefore, identification and quantitative determination of the specimen can be carried out by knowing the presence and abundance of the magnetic-labeled body in the liquid phase.

The presence and abundance of the magnetic-labeled body can be known by radiating (inputting) a laser beam into a measuring system comprising a liquid phase and a specimen dispersed therein, and measuring the change in the intensity of outgoing beams from the measurement system.

Herein, by the term "outgoing beams" it is meant scattered beams, permeated beams, reflected beams, interfered beams or diffracted beams of incident laser beams.

FIG. 1 is a schematical view of a laser magnetic immunoassay apparatus according to one embodiment of the present invention. In this case, the apparatus is one which measures the adjusted specimen and comparative samples described above by laser beam scattering or permeation. In FIG. 1, 12 is a HeNe laser of 5 mW output, for example, 13 is an incident beam, 15a is a scattered beam flux, 15b is a permeated beam, 16 is an Si photo diode, 17 is lock-in-amplifier, 18 is an electromagnet, 19 is a low-frequency power source of 0.5 Hz, for example, 20 is a lens for condensing scattered beams, and 21 is a polarizer plate. A glass cell 11 containing a specimen or a comparative sample is fitted in the electromagnet 18 and the magnetic-labeled body are guided and concentrated around the incident laser beam 13, and then scattered beam flux 15a or permeated beam 15b from the liquid containing the specimen due to the radiation by the laser 12 is detected by means of the photo diode 16. Since the movement of the magnetic-labeled virus antibody 4 in the liquid phase is controlled by the electromagnet 18, the intensity of the scattered beam flux 15a or the permeated beam 15b comes to be in synchronization with the frequency of the low-frequency power source 19. Therefore, amplification of only the scattered beam flux 15a or permeated beam 15b which is in synchronization with the frequency of the low-frequency power source 19 by means of the lock-in amplifier 17 makes it possible to measure the intensity of the scattered beam or permeated beam from the liquid containing the specimen without receiving disturbances from outside such as change in temperature and the like. In this embodiment, the intensity of the scattered beam from the liquid containing the specimen is measured in synchronization with the frequency of alternating current magnetic field. On the other hand, the intensity of the scattered beam from the comparative sample is of direct current-type since the latter contains no magnetic-labeled body and therefore lacks components which synchronizes with the alternating current magnetic field, thus giving information on background level when measurement is made using the lock-in amplifier 17.

Further, although ordinary measurements may be carried out by means of scattered beams, there are sometimes cases that use of permeated beams enables measurement with high S/N ratio depending on the kind and concentration of specimen. 20 is a condenser for converging scattered beams, and the polarizer plate 21 is used in order to measure the polarized component from the specimen separately. More particularly, approximately linear polarized beam is used as an incident laser beam, which is designed to pass across crossed Nicol's prisms so that it can be turned off when no magnetic-labeled body is present in a liquid phase, and when a magnetic-labeled body is guided into the light pass and the state of polarization is changed, outgoing beams can be obtained. In this case, the low-frequency power source is not limited to 0.5 Hz type, but it is preferred to select most suitable frequency depending on the viscosity of an aqueous solution containing a specimen and the intensity of the magnetic field.

According to a second embodiment of the present invention, a laser magnetic immunoassay is provided, which comprises a step of labeling an antigen or antibody with micro-particles of a magnetic substance to form a magnetic-labeled body and subjecting the magnetic-labeled body and a specimen to an antigen-antibody reaction to form a magnetic-labeled body-specimen complex, a step of separating and removing unused magnetic-labeled body from the magnetic-labeled body-specimen complex after the above step, a step of dispersing the magnetic-labeled body-specimen complex after the removal of the unused magnetic-labeled body in a liquid and radiating a laser beam, and a step of measuring outgoing beams from the mgnetic-labeled body-specimen complex due to the radiation of the laser beam, wherein the laser magnetic immunoassay further comprises a step of holding a specimen container for storing the liquid having dispersed therein the magnetic-labeled body-specimen complex with the axis direction of the specimen container being substantially in line with the light axis direction of the radiated laser beam and gradually moving the applied magnetic field along the axis direction to guide and concentrate the magnetic-labeled body-specimen complex to a position near the light axis of an optical system for receiving the outgoing beams, and a step of giving the magnetic-labeled body-specimen complex after being guided and concentrated to the position near the light axis of the outgoing beams a periodically varying magnetic field near the light axis of the outgoing beams, thus enabling selective detection of only an outgoing beam that is in synchronization with the variable component of the periodically varying magnetic field.

According to one variation of the second embodiment, a product of an antigen-antibody reaction obtained from a specimen and a corresponding antibody or antigen specific to the specimen can be used as the specimen which is subjected to an antigen-antibody reaction with the magnetic-labeled body, and anti-immuno-globulin can be used as the antibody to be labeled with the micro-particles of the magnetic substance.

According to another variation of the second embodiment, unknown virus or virus antibody can be used as the specimen, and virus antigen or antibody can be used as the antigen or antibody to be labeled with the micro-particles of the magnetic substance.

According to still another variation of the second embodiment, the specimen to be subjected to the antigen-antibody reaction with the magentic-labeled body does not have to be subjected to the reaction, that is, both the specimen to be subjected to the antigen-antibody reaction with the magnetic-labeled body and the magnetic-labeled body-specimen complex may be antigens and antibodies simultaneously.

In other words, when the specimen is an antigen or antibody which is susceptible to a specific antigen-antibody reaction with the magnetic-labeled body, the magnetic-labeled body remains in the liquid phase containing the specimen and the specimen can be detected by measuring outgoing beams which vary periodically in synchronization with the variation of the magnetic field.

On the other hand, when the specimen is an antigen or antibody which is not susceptible to a specific antigen-antibody reaction with the magnetic-labeled body, no magnetic-labeled body remains in the liquid in the specimen container. In this case, it is possible to identify and quantitatively determine the specimen by measuring the presence and abundance of the magnetic-labeled body in the liquid phase. The presence and abundance of the magnetic-labeled body can be determined by measuring the change in the intensity of the outgoing beams from the specimen dispersed in the liquid phase.

The step of separating and removing the unreacted magnetic-labeled body may be performed by means of a permanent magnet or an electromagnet.

Further, according to a third embodiment of the present invention, a laser magnetic immunoassay apparatus for practicing the assay according to the above-described embodiment is provided, which comprises a specimen container for storing a specimen labeled with micro-particles of a magnetic substance, a laser beam radiating optical system for guiding a laser beam into the specimen container, a light receiving system arranged so as to receive outgoing beams from the specimen which receives the laser beam, a magnetic field moving means for moving the magnetic field along the axis of the specimen container toward the axis of the outgoing beams which is the light axis of the light receiving system, a magnetic field driving means for periodically varying the magnetic field sandwiching the position at which the specimen container is arranged on the light axis of the outgoing beams, and an electronic circuit system for selectively detecting the outgoing beams that are in synchronization with the variable component of the magnetic field generated by the magnetic field driving means.

The magnetic field driving means may comprise a magnet which can move along the axis of the specimen container or a plurality of electromagnets arranged along the axis of the specimen container and sequentially excited. Further, according to a preferred variation of the third embodiment, the magnetic field driving means may comprise a pair of magnets or alternately excitable electromagnets which are held sandwiching the sepcimen container with a predetermined distance from each other and with the relative distance from the specimen container which can be varied periodically.

Further, according to another preferred variation of the third embodiment, the specimen container can be a container having a heterogeneous diameter cross-section, that is, it has an opening of a large cross-section at a position where a laser beam is introduced and a small cross-section on the light axis of the outgoing beam.

According to a fourth embodiment of the present invention, a laser magnetic imunoassay is provided, which comprises at least a first step of subjecting a magnetic-labeled body, which consists of a predetermined antigen or antibody and micro-particles of a magnetic substance attached thereto as a label, and a specimen to an antigen-antibody reaction to form a magnetic-labeled body-specimen complex, a second step of separating and removing unused magnetic-labeled body from the magnetic-labeled body-specimen complex after the first step, a third step of dispersing in a liquid an antigen-antibody complex including the magnetic-labeled body-specimen complex, and a fourth step of radiating a laser beam to the liquid and measuring outgoing beams from the magnetic-labeled body-specimen complex, wherein the method further comprises precipitating floating matters dispersed in the liquid after the third step and removing the magnetic-labeled body-specimen complex from the precipitate.

Also, according to a preferred variation of the fourth embodiment, the treatment of precipitating the floating matters in the solution can be performed by subjecting the container storing the solution having dispersed therein the specimen to centrifugal separation; separation of the magnetic-labeled body-specimen complex from the precipitate thus-formed at one end of the container can be performed by moving the magnet arranged outside the container on the side thereof from the vicinity of the precipitate to farther positions.

Further, advantageously, the immunoassay according to the fourth embodiment of the present invention comprises an operation of holding the container storing the liquid having dispersed therein the magnetic-labeled body-specimen complex on the axis of the laser beam and guiding and concentrating the magnetic-labeled body-specimen complex on the laser beam axis by means of a magnetic field moving in the direction along the axis of the specimen container, an operation of giving a periodically varying magnetic field at a position near the outgoing beam axis to the magnetic-labeled body-specimen complex after the complex being concentrated at the position near the light axis of the outgoing beam, and an operation of selectively detecting such an outgoing beam as to be synchronized with the variable component of the periodically varying magnetic field.

In the above embodiment, various floating matters such as debris of support material for use in immobilization which is inevitably contained in the liquid having dispersed therein the specimen are separated from the magnetic-labeled body-specimen complex. The floating matters in the liquid not only increase the laser beam scattering excessively in the higher concentration region as background scattering but also prevent the improvement in the accuracy of the measurement since they move together with the specimen upon the guiding operation for guiding the specimen by means of magnetic force, or for some other reasons.

Therefore, in the immunoassay according to the present invention, the liquid having dispersed therein the specimen is subjected to centrifugal separation apparatus in order to have all the floating matters including the specimen once precipitated and thereafter, only the specimen is guided to a detection region for detecting outgoing beams by means of magnetic force.

Needless to say, it is also possible to set up conditions for centrifugal separation such that only those floating matters excluding the specimen in order to extract the specimen. However, this approach requires reconsideration on the conditions for separation as soon as whenever conditions for liquidification or fluidization or materials of support layer for immobilization are changed, and therefore it is very disadvantageous in practice.

Although it is also possible to separate the specimen by means of magnetic force at the time of fluidization, the method of the present invention which enables operations in the same container throughout from the stage of fluidization up to separation is more advantageous.

Upon measurement of the outgoing laser beams, disturbances from outside and influences by the background can readily be eliminated, for example, by selectively measuring, while oscillating the magnetic-labeled body-specimen complex in an alternating current magnetic field, only the change in the outgoing beams such as scattered light and permeated light which are in synchronization with the alternating current magnetic field.

With these features of the construction of the present invention, limit of the method utilizing AFP can be overcome while using the same laser beam scattering measurement. Further, these features of the present invention not only contribute to improvement in the detection sensitivity but also enable automatization of measurement.

Furthermore, according to a fifth embodiment of the present invention, a laser magnetic immunoassay is provided, which comprises dispersing in a liquid a specimen to be detected, an antibody or antigen immobilized to a non-magnetic particle having a size or mass sufficiently large as compared with the antigen or antibody and capable of forming an antigen-antibody complex as a result of a specific antigen-antibody reaction with the specimen, and a magnetic-labeled body containing micro-particles of a magnetic substance as a label and susceptible to a specific antigen-antibody reaction with the antigen-antibody complex, forming a magnetic substance-antigen antibody complex which is a complex of the antigen-antibody complex and the magnetic-labeled body, selectively guiding and separating the magnetic substance-antigen antibody complex from unused magnetic-labeled body, radiating a laser beam into the liquid containing only the magnetic substance-antigen antibody complex selectively separated, and detecting the outgoing beams from the magnetic substance-antigen antibody complex to detect the specimen.

Further, as an apparatus for practicing the method according to the fifth embodiment, there is provided a laser magnetic immunoassay apparatus for forming an antigen-antibody complex by subjecting a specimen to be detected and an antibody or antibgen immobilized to a non-magnetic particle having a size or mass sufficiently large as compared with the antibody or antigen and susceptible to a specific antigen-antibody reaction with the specimen, labeling the antigen-antibody complex with micro-particles of a magnetic substance, radiating a laser beam into a liquid containing the resulting magnetic substance-antigen antibody complex, detecting outgoing beams to detect the specimen, wherein the apparatus comprises a first container for storing a liquid in which the specimen, the antibody or antigen immobilized to the non-magnetic particle and the micro-particles of the magnetic substance are added to form the antigen-antibody complex and label the antigen-antibody complex with the micro-particles of the magnetic substance, a guiding means comprising a first magnetic force adjusted so as to be capable of guiding the magnetic substance-antigen antibody complex and a second magnetic force adjusted so as to be capble of guiding the micro-particles of the magnetic substance not bound to the non-magnetic particle but incapble of guiding the magnetic substance-antigen antibody complex, a second container communicated to the first container at the upper part thereof so that the liquid can be transferred and is adapted to receive the magnetic substance-antigen antibody complex guided from the liquid in the first container by moving the guiding means under the conditions of applying the first magnetic force, a third container communicated to the first container at the upper end thereof and is adapted to receive the micro-particles of the magnetic substance not bound to the non-magnetic particle guided from the liquid in the first or second container by moving the guiding means under the conditions of applying the first magnetic force, a radiating means for radiating a laser beam into the second container, and a measuring means for measuring the scattering of the laser beam in the second container.

The laser magnetic immunoassay uses micro-particles of a magnetic substance as a label substance and the antigen or antibody subjected to an antigen-antibody reaction with the specimen is immobilized to a non-magnetic particle which has a size or mass sufficiently large as compared with the antigen and antibody as well as the antigen-antibody complex prepared therefrom, which are one of major features of the present invention.

More particularly, in the case where the antigen or antibody is immobilized on the surface of the non-magnetic particle, the method of this embodiment of the present invention is more advantageous than the case where the non-magnetic particle is absent since not only the subsequent step of fluidization becomes unnecessary but also detection of a complex of the non-magnetic particle which is larger than the specimen, the specimen and the magnetic-labeled body is performed by radiating the laser beam to the complex and therefore results in remarkable increase in the detection sensitivity. Needless to say, the micro-particles of the magnetic substance and non-magentic particle themselves have no problem in view of radioactive rays or toxicity, and there is no limitation in utilizing them.

In addition, various materials, for example, various compound magnetic substances such as magnetite and $\gamma$-ferrite or metal magnetic substances such as iron and cobalt are available as the micro-particles of the magnetic substance and label substances stable to specimens can be selected with ease. Many materials are provided for non-magnetic particle such as plastics, e.g., polystyrene latex or inorganic substances such as silica, and non-magnetic particles stable to antigens or antibodies to be measured are available with ease. More specifically, the non-magnetic particle is formed by coating the surface of micro-particle having a large mass as a core with a substance suitable for immobilizing antigens or antibodies.

In the method according to this embodiment, selective operation can be performed by making use of the fact that the label substance is a magnetic substance and attracting the antigen or antibody labeled therewith (magnetic-labeled body) and further magnetic substance-antigen antibody complex forming an integral body as the result of reaction.

On the other hand, the non-magnetic particle which is attached to the antigen or antibody to be subjected to an antigen-antibody reaction with the specimen has a mass or size larger than the micro-particles of the magnetic substance and therefore, the antibody or antigen subjected to reaction with the corresponding antigen or antibody immobilized to the non-magnetic particle cannot be attracted unless magnetic force stronger than that applied to unused antibody or antigen is applied thereto.

Therefore, there are three types of liquids containing the specimen after the first operation of the method of the present invention as described below.

(1) Those insensitive to magnetic force (unused antigen or antibody immobilized to non-magnetic particle, micro-particles of non-magnetic substance as impurities, etc.).

(2) Those attracted by weak magnetic force (unused antigen or antibody labeled with micro-particles of a magnetic substance).

(3) Those attracted by magnetic force of above a predetermined level of the intensity (antigen-antibody complex including non-magnetic particle).

Therefore, by using guide means with different intensity of applied magnetic force, antigen-antibody complex after reaction or unused antigen or antibody can be selectively guided from the above-described liquids.

Further, there are enumerated some examples of operational procedure in the above cases. That is, an aqueous solution in which only (3) is dispersed can be obtained by at first operating the weak magnetic force guiding means in order to remove (2) from the liquid having dispersed therein (1), (2) and (3), and then operating the strong magnetic force guiding means is used to guide (3) into deionized water. On the other hand, only (2) can be removed by at first operating the strong magnetic force guiding means in order to guide (2) and (3) into deionized water followed by operating the weak magnetic force guiding means. Any appropriate combination of operational procedures can be selected.

Separation based on size can be performed using a porous filter.

One of major features of the laser magnetic immunoassay according to the present invention is that detection step using laser beam scattering is performed subsequently and continuously after the above-described step of adjusting the specimen.

More particularly, when a laser beam is applied to the specimen liquid prepared by the above-described procedures, the laser beam is scattered by the magnetic substance-antigen-antibody complex dispersed in deionized water, and therefore, the magnetic substance-antigen antibody complex in deionized water can be detected and determined quantitatively by measuring scattering of the laser beam. In this case, the intensity of outgoing beams can be measured by arranging a light receptor at a position deviated from the outgoing pass of the laser beam, or alternatively, a light receptor may be arranged on the light pass of the laser beam in order to measure the intensity of the laser beam which is decreased due to scattering corresponding to the intensity of the outgoing beams. Further, the present inventors confirmed that high sensitivity detection without being influenced by the presence of the container is possible by radiating a laser beam in the direction of the opening of the container (from above in practice) and measuring outgoing beams in the direction of the opening of the container (from above in practice).

Also, upon the measurement of laser beam scattering, it has been confirmed that the magnetic substance-antigen-antibody complex can be concentrated in a predetermined region in deionized water by applying a predetermined level of magnetic field to the container filled with a specimen, and by such procedures the detection sensitivity can be further improved and detection with sensitivity in the order of picogram is possible.

Furthermore, influences by disturbances from outside and background can be very effectively eliminated and detection sensitivity can be further improved by modulating the applied magnetic field described above with a predetermined frequency by means of alternating current power source and detecting only variation in the laser beam scattering that is in synchronization with the modulation frequency.

An apparatus which the present inventors propose as an apparatus constructed for practicing the assay as described above advantageously must comprise at least a container for storing a specimen, a guiding means for performing various operations on the specimen in the container and a measuring means for measuring laser beam scattering.

Although a concrete description will be made later herein-below, as for the container, it is advantageous to perform an antigen-antibody reaction, separation of unused antigen or antibody, selective separtion of magentic substance-antigen-antibody complex continually in on specimen container provided with a low partition wall so constructed that the contents can communicate in the vicinity of the surface of the liquid contained therein. In this technique, unused magnetic-labeled body or various floating matters which are present inevitably together with antigen, antibody and the like in the liquid, which are factors preventing improvement in the detection limit and detection accuracy, can be removed very efficiently by a series of oeprations performed throughout in the specimen container.

As for the guiding means, two or more permanent magnets having predetermined magnetic forces may be used. However, it is advantageous to use electromagnets with which magnetic force can be varied freely. By the use of the electromagnets concentration of the specimen in deionized water or application of alternating current magnetic field can be performed with ease.

Further, considering these functions collectively, it is advantageous to construct the apparatus such that the container storing the specimen moves relatively with respect to the concentrating means fixed to the base on which the appparatus is mounted, and that the laser beam is radiated just below the concentrating means. Details will be described later hereinbelow with reference to concrete examples.

With the construction characteristic to the present invention, the method of the present invention by far exceeds the limit of the method utilizing AFP and has attained detection sensitivity and detection accuracy which approach those of RIA method. Further, the method of the present invention is very advantageous in view of automatization of tests, for example, as will be described later hereinbelow.

The description in this section has been made in the case where the present invention is applied to so-called indirect method, in which an antigen or antibody having attached thereto micro-particles of a magnetic substance and non-magnetic particle is subjected to an antigen-antibody reaction, and immunological measurement is performed. However, the present invention is also applicable to a method in which unknown antibody in the specimen is directly immobilized on the surface of the non-magnetic particle and the product is subjected to an antigen-antibody reaction with the magnetic-labeled body. The latter method is a direct method. The indirect method includes one in which the specimen and the magnetic-labeled body are reacted positively, and so-called competitive inhibitory reaction detection method in which the reaction between the specimen and the magnetic-labeled body is inhibited. The present invention can be applied effectively to both of them.

According to the above-described embodiment, no resort is had to the method in which a specimen is immobilized to a support such as gelatin and removed from unused antigen or antibody labeled with microparticles of a magnetic substance, and therefore, there is no need to rupture the support before removing the specimen upon measurement of scattering of laser beam, which is very convenient.

As described above, in the assay which makes use of scattering of a laser beam by the specimen dispersed in the liquid, it is critical for improving the sensitivity to remove unused labeled body and impurities in the liquid serving as background. Therefore, a method of preparing specimens is desired which is easy and accurate to remove unreacted labeled body and impurities and which can prevent contamination of impurities as far as possible.

That is, according to a sixth embodiment of the present invention, a specimen container for use in a laser magnetic immunoassay is provided, which comprises a side walls of a predetermined height defining a storage cavity, a first partition wall provided in the storage cavity and having a predetermined second height which is lower than the side walls, and a second partition wall provided in the storage cavity and having a predetermined third height which is lower than the first partition wall, a part of the side walls and the first partition wall as well as the second partition wall defining a first storage cell, a part of the side wall and the first partition wall defining a second storage cell and a part of the side walls and the second partition walls defining a third storage cell, with the container being open upwards, and the bottom of the first storage cell being adapted so that an antibody or antigen which is susceptible to a specific antigen-antibody reaction with a corresponding antigen or antibody to be measured can be immobilized in a solid phase.

Also, a method of preparing specimens for use in a laser magnetic immunoassay using the above specimen container is provided, which comprises using an integrally constructed specimen container comprising first and second storage cells partitioned by a first partition wall lower than the side walls, a third storage cell partitioned by the first partition wall and the second partition wall lower than the first partition wall, with the upper end of each storage cell being open upwards, a first operation of immobilizing in a solid phase an antibody or antigen susceptible to a specific antigen-antibody reaction with a specimen to be quantitatively determined on the bottom the first storage cell, a second operation of filling the first storage cell with purified water to the height of the second partition wall, dispersing in the purified water an antibody or antigen labeled with micro-particles of a magnetic substance and subjecting the antibody or antigen as well as specimen in the solid phase to an antigen-antibody reaction, a third operation of filling the second and third storage cell with purified water to the height of the side walls so that the first, second and third storage cells can be communicated with each other above the height of the first and second partition walls, a fourth operation of guiding unused magnetic-labeled body in the first storage cell with a guiding means capable of generating magnetic force to the second storage cell and then removing the contents in the second storage cell, a fifth operation of fluidizing the antigen or antibody immobilized in the first storage cell and guiding the magnetic substance-antigen-antibody complex in the first storage cell with a guiding means capable of generating magnetic force to the third storage cell, and after the fifth operation, quantitatively determining the antigen-antibody complex in the specimen obtained in the third storage cell.

In the above-described apparatus, the mechanical process using a permanent magnet is complicated in construction while the process using an electromagnet takes a long time for local concentration of the magnetic-labeled body by means of magnetic field since the construction of the electromagnet is unsuitable for generating strong magnetic field, which is disadvantageous.

Therefore, the present invention has for its object to provide a laser magnetic immunoassay apparatus which has a simple constructtion and can perform local concentration the magnetic-labeled body in a short period of time.

That is, according to a seventh embodiment of the present invention, the apparatus comprises a specimen container for storing a liquid containing a magnetic-labeled body, a pair of electromagnets arranged sandwiching the specimen container, a power source capable of generating two kinds of currents, one direct current and the other intermittent pulsate current and providing the generated current to the electromagnets, a laser beam radiating optical system for guiding a laser beam to the specimen container, a light receiving system arranged so as to be capable of receiving outgoing beams from a magnetic-labeled body-specimen complex to which the laser beam is applied, and an electronic circuit system for selectively detecting only the outgoing beams that are in synchronization with the intermittent pulses from the light receiving system and processing signals of the outgoing beams by repeated summation and finding average, with the magnetic core and magnetic pole piece of the electromagnets being made of a material having a low residual magnetization so that the magnetic field can increase toward the center of the magnetic core where the magnetic field is maximum.

According to a preferred variation of the seventh embodiment, the specimen container is a small tube or pipe, and the apparatus is provided with a means for holding the small tube horizontally between the pair of electromagnets, an optical system for guiding the laser beam radiated along the axis of the small tube toward the central portion of the small tube, and an optical system for extracting outgoing beams from the specimen in the central position between the pair of electromagnets from above or from below of the specimen and guiding it to a photomultiplier.

According to another preferred variation, the power source is controlled so as to output, after continuously outputting strong direct current in a predetermined period of time, intermittent pulses of a frequency within the range between 0.05 Hz and 10 Hz and having a peak value smaller than that of the continuous direct current and without DC off-set.

According to still another preferred variation, the pair of electromagnets are provided with a electric circuit and magnetic circuit so that indepedent excitation or cooperative excitation can be selected.

In the present invention, a pair of special electromagnets are used with switch between direct current excitation and intermittent pulse excitation to control the concentration of the specimen and control outgoing beams from the specimen effectively. This is very advantageous for improving in the reduction of measurement time and in the accuracy of measurement.

Further, upon measurement of outgoing laser beam, the measurement sensitivity and reproducibility of measurement can be remarkably increased by performing repeated summation and finding average of outgoing beam signals from the specimen in addition to detection of outgoing beams in synchronization with the variation period of the magnetic field according to the above embodiment of the present invention.

According to an eighth embodiment of the present invention, a laser magnetic immunoassay is provided, which comprises at least a first step of subjecting a magnetic-labeled body prepared by attaching microparticles of a magnetic substance as a label to a predetermined antigen or antibody and an antibody or antigen as a specimen to an antigen-antibody reaction, and a second step of applying a magnetic field to a solution containing a magnetic-labeled body-specimen complex which is a complex between the magnetic-labeled body after the first step and the sepcimen and guiding and concentrating the magnetic-labeled body-specimen complex to a region where a laser beam is radiated, with detection being performed by (a) selectively detecting only the outgoing beams that are in synchronization with the intermittent pulses, or (b) controlling the movement of the concentrated magnetic-labeled body-specimen complex by means of magnetic force and surface tension of the liquid and detecting only the outgoing beams that are in synchronization with the control.

According to a preferred embodiment of this embodiment, the above-described steps are preformed in a specimen container having an opening upwards, and the guiding and concentration step and the detection step are performed by using an electromagnet arranged below the specimen container and a magnetic pole piece arranged immediately above the water surface of the specimen container and opposing the core of the electromagnet, and detecting the change in the amount of reflected light which is in synchronization with the period of the varying magnetic field.

Further, in the above detection step, quantitative determination of the specimen can be performed by counting the number of interference fringes appearing in the reflected laser beam due to the movement of the magnetic-labeled body-specimen complex.

Further, according to a ninth embodiment of the present invention, a laser magnetic immunoassay apparatus is provided, which comprises at least a specimen container having an upward opening for storing a magnetic-labeled body-sepcimen complex, a laser beam source, an incident optical system for guiding a laser beam from the laser beam source to the water surface of the specimen container, a light receiving system for receiving reflected beam from the specimen to which the laser beam is applied, a concentrating means for concentrating the magnetic-labeled body-specimen complex to a point immediately below the water surface of the specimen container, and a driving means for periodically driving the magnetic-labeled body-specimen complex, wherein the concentrating means and the driving means are constructed by an electromagnet, a magnetic pole piece arranged as opposing the core of the electromagnet and sandwiching the specimen container together with the electromagnet, and a power source for exciting the electromagnet, and wherein the apparatus further comprises an electronic circuit system for selectively detecting the reflected beams which are in synchronization with the period.

According to a preferred variation of this embodiment, a means for moving the specimen container, or the electromagnet and the magnetic pole piece, in a horizontal plane.

As the result of investigation by the present inventors on a method for detecting reflected light from magnetic-labeled body-specimen complex, it has now been found that changes in the intensity of reflected light in synchronization with alternating current magnetic field as a feature specific to the construction of the present invention. That is, as described above, the magnetic-labeled body-specimen complex concentrated on the water surface immediately below the magnetic pole piece is strongly attracted by the magnetic pole piece when the electromagnet is excited strongly so that a phenomenon occurs in which the water surface immediately below the magnetic pole piece is slightly elevated. When the attraction of the magnetic-labeled body-specimen complex by magnetic force is ceased, the elevated water surface automatically returns flat due to the surface tension of water.

When a laser beam is radiated to the minute elevate portion, interference fringes appear in the reflected light in numbers corresponding to the degree of elevation. Since the interference fringes can also appear due to floating matters on the water surface, only those interference fringes that are in synchronization with the variation of magnetic field must be detected in order to avoid disturbances from outside. If the amount of the magnetic-labeled body-specimen complex is not larger than picogram, the number of the interference fringe is at most one. In this case, it is sufficient to detect the change in the intensity since the intensity of the reflected light varies in synchronization with the variation of magnetic field. It is also satisfactory to detect the change in the diameter of the interference fringe.

According to a tenth embodiment of the present invention, a laser magnetic immunoassay is provided, which comprises at least a first step of subjecting a magnetic-labeled body prepared by attaching microparticles as a label to a predetermined antigen or antibody and a corresponding antibody or antigen as a specimen to an antigen-antibody reaction, and a second step of applying magnetic field to a solution containing a magnetic-labeled body-specimen complex which is a complex between the magnetic-labeled body and the specimen after the first step in order to guide and concentrate the magnetic-labeled body-specimen complex to a predetermined position, wherein the laser beam is radiated simultaneously or in chronological sequence both at the position of concentration where the magnetic-labeled body-specimen complex is present and at a position of non-concentration where the magnetic-labeled body-specimen complex is absent, and differential between the outgoing beam from the position of concentration and the outgoing beam from the position of non-concentration.

According to a variation of this embodiment, the second step is performed using a specimen container having an upward opening, and guiding and concentration are performed by means of a magnet arranged below the specimen container and a magnetic pole piece arranged immediately above the water surface of the specimen container in opposition to the magnet, with the detection step being carried out by radiating simultaneously or in chronological sequence at the water surface immediately below the magnetic pole piece and at the water surface in the vicinity of the magnetic pole piece.

According to another variation of the embodiment, the second step is performed using a specimen container in the shape of small tubes, and the guiding and concentrating step is performed by using a magnet so constructed that the magnetic field at a predetermined position in the specimen container is maximum and the magnetic field increases toward the maximum point of the magnetic field and radiating at the position of the specimen container where the magnetic field is maximum and a position in the vicinity thereof simultaneously or in chronological sequence.

In the above-described detection step, any one of outgoing light, permeated light, reflected light, interference light and diffracted light from the specimen can be selected.

Further, in the above-described detection step, simultaneous radiation can be performed by dividing the laser beam into two beams.

Furthermore, in the above-described detection step, the chronological radiation can be performed by scanning the laser beam between the position of concentration and the position of non-concentration.

In this case, quantitative determination of the specimen with selectively detecting outgoing beams in synchronization with the frequency at which the laser is scanned results in improvement in the detection sensitivity. According to an eleventh embodiment of the present invention, a laser magnetic immunoassay apparatus is provided, which comprises at least a specimen container for storing a specimen labeled with microparticles of a magnetic substance, a guide means for guiding and concentrating a magnetic-labeled body-specimen complex to a point in the specimen container, an incident optical system for guiding a laser beam to the sepcimen container, a light receiving system for receiving scattered light, permeated light, reflected light, interefered light or diffracted light from the magnetic-labeled body-specimen complex and a solution not containing the magnetic-labeled body-specimen complex, wherein the apparatus further comprises a gradient magnetic field generating means and a beam splitter or a polarizer.

According to a preferred variation of this embodiment, the gradient magnetic field generating means comprises a permanent magnet or an electromagnet and a magnetic pole piece arranged in opposition to the permanent magnet or electromagnet and sandwiching the specimen container together therewith.

Further, according to another variation of this embodiment, the apparatus is so constructed that either the specimen container, or the permanent magnet or electromagnet and the magnetic pole piece can move in a horizontal plane.

When the method in which the magnetic-labeled body-specimen complex is driven in the liquid by means of outside magnetic force, there is naturally a limitation in the followability to the outside magnetic force due to the viscosity resistance of the solution. Therefore, the tenth and eleventh emobodiments described above enables measurements with high S/N ratios in a short period of time since they can eliminate background noises from other than the specimen which disturb signals from the magnetic-labeled body-specimen complex in spite of the problem that it takes a long time to perform measurement, which is encountered when repeated summation and finding average of the outgoing light, permeated light, reflected light or interefered light from the magnetic-labeled body-specimen complex are performed in order to increase S/N ratio.

EXAMPLES

The present invention will be described in greater detail with reference to the following examples but the present invention is by no means limited thereto.

Firstly, methods for preparing a liquid having dispersed therein a magnetic-labeled body-specimen complex for use in the laser magnetic immunoassay of the present invention.

Preparation Method I

FIGS. 2(a) to 2(f) illustrate an example of the method for preparing the liquid having dispersed therein a magnetic-labeled body-specimen complex for use in the laser magnetic immunoassay of the present invention.

FIGS. 2 (a) to (d) illustrate steps of preparing test specimen liquid and FIG. 2 (e) illustrate steps of preparing a comparative sample.

FIG. 2 (a) illustrates a step of immobilizing to a support 1 a known virus antibody 2, FIG. 2 (b) a step of injecting into the virus antibody an unknown virus antigen 3 in the blood of a patient and allowing an antigen-antibody reaction to occur, FIG. 2 (c) a step of reacting the virus antigen 3 with a magnetic-labeled virus antibody 4, and FIG. 2 (d) a step of introducing a magnetic-labeled body specimen-complex obtained after dissolving and removing the support 1 into a glass cell 11 and dispersing it in an aqueous solution.

On the other hand, FIG. 2 (e) illustrates a step of separating and removing the magnetic-labeled virus antibody 4 which does not undergo antigen-antibody reaction with the specimen because of absence of the virus antigen 3 from the immobilized antibody using a rare earth metal magnet 5. FIG. 2 (f) illustrates a step of fluidization of a comparative sample by introducing the specimen 2 into the glass cell 11 after dissolving and removing the support 1 and dispersing it in an aqueous solution.

Excessive unused magnetic-labeled virus antibody 4 can be removed from the magnetic-labeled body-specimen complex by applying a step similar to the step shown in FIG. 2 (e) to the step shown in FIG. 2 (c), that is, by removing unused magnetic-labeled virus antibody 4 by means of the rare earth metal magnet 5.

The step of FIG. 2 (e) may be performed using a magnet and washing in combination. An antibody which has a good affinity with virus and specific antibodies and therefore is suited for labeling virus and the like and which can specifically bind with the virus antigen 3, after being coated on the surface thereof with micro-particles of magnetite were used as the magnetic-labeled virus antibody 4. Suitable particle size of the magnetic micro-particles is in the order of 50 nm.

Preparation Method II

FIGS. 3 (a) to (f) illustrate a second example of the method of preparing a liquid having dispersed therein a magnetic-labeled body-specimen complex for use in the laser magnetic immunoassay of the present invention. FIGS. 3 (a) to (d) illustrate steps of preparing test specimen liquid and FIG. 3 (e) and (f) illustrate steps of preparing a comparative sample. In this example, the virus antigen 3 is immobilized to the support 1 as shown in FIG. 3 (a). The virus antigen 3 and the virus antibody 2 in the blood of a patient which serves as a specimen are subjected to an antigen-antibody reaction (FIG. 3 (b)), and the product is further reacted with a magnetic-labeled anti-immunoglobulin 4' labeled with ultramicro-particles of magnetite, which is susceptible to a specific antigen-antibody reaction with the virus antibody 2 (FIG. 3 (c)). Then, after dissolving and removing the support 1, the magnetic-labeled body-specimen complex is introduced into a glass cell 6 and dispersed in an aqueous solution (FIG. 3 (d)).

FIG. 3 (e) illustrates a step of separating and removing unused magnetic-labeled anti-immunoglobulin 4' from the immobilized antigen using a rare earth metal magnet 5. FIG. 3 (f) illustrates a step of fluidization of a comparative sample.

After preparing test specimen liquid through these steps, quantitative determination of the specimen is performed according to the laser beam scattering method of the present invention.

Preparation Method III

FIGS. 4 (a) to (d) illustrate a third example of the method of preparing a liquid having dispersed therein a magnetic-labeled body-specimen complex for use in the laser magnetic immunoassay of the present invention.

In this example, unknown influenza virus 3' collected from a patient, for example, is immobilized to the support 1 as shown in FIG. 4 (a). The influenza virus 3' and known magnetic-labeled virus antibody 4 labeled with ultramicro-particles of iron are subjected to an antigen-antibody reaction (FIG. 4 (b)), excessive magnetic-labeled virus antibody 4 is separated and removed by means of the electromagnet 5. Then, after dissolving and removing the support 1, the magnetic-labeled body-specimen comlex is introduced into the glass cell 6 and dispersed in an aqueous solution to prepare test specimen liquid (FIG. 4 (d)).

Preparation Method IV

FIGS. 5 (a) to (f) illustrate an example of the method of preparing a liquid having dispersed therein a magnetic-labeled body-specimen complex for use in the laser magnetic immunoassay of the present invention based on a competitive inhibitory reaction.

In this example, known virus antibody 2 is immobilized to the support 1 composed of gelatin as shown in FIG. 5 (a). The thus-immobilized antibody 2 and virus antigen 3 from a patient are subjected to an antigen-antibody reaction (FIG. 5 (b)). A magnetic-labeled virus antigen 2' labeled with a magnetic substance in a separate step is reacted with the specimen after the antigen-antibody reaction in the step (b) (FIG. 5 (c)), and excessive, i.e., unused magnetic-labeled virus antigen 2' is separated and removed by means of the electromagnet 5 (FIG. 5 (d)). Then, after dissolving and removing the support 1, the magnetic-labeled body-specimen comlex is introduced into the glass cell 11 and dispersed in an aqueous solution to prepare test specimen liquid (FIG. 5 (d)).

FIG. 5 (e) illustrates a step of reacting a comparative sample with the magnetic-labeled virus antigen 2', and FIG. 5 (f) a step of collecting unused magnetic-labeled virus antigen 2' by means of the magnet 5.

Preparation Method V

FIGS. 6 (a) to (f) illustrate another example of the method of preparing a liquid having dispersed therein a magnetic-labeled body-specimen complex for use in the laser magnetic immunoassay of the present invention based on a competitive inhibitory reaction.

In this example, known virus antigen 3 is immobilized to the support 1 composed of gelatin as shown in FIG. 6 (a). The thus-immobilized antigen 3 and virus antibody 2 from a patient are subjected to an antigen-antibody reaction (FIG. 6 (b)). A magnetic-labeled virus antibody 4 labeled with a magnetic substance in a separate step is reacted with the specimen after the antigen-antibody reaction in the step (b) (FIG. 6 (c)), and excessive, i.e., unused magnetic-labeled virus antibody 4 is separated and removed by means of the electromagnet 5 (FIG. 6 (d)). Then, although not shown, after dissolving and removing the support 1, the magnetic-labeled body-specimen complex is introduced into the glass cell 11 and dispersed in an aqueous solution to prepare test specimen liquid (FIG. 4 (d)).

FIG. 6 (e) illustrates a step of reacting a comparative sample with the magnetic-labeled virus antibody 4, and FIG. 6 (f) a step of collecting unused magnetic-labeled virus antibody 4 by means of the magnet 5.

In this example, too, the magnetic-labeled virus antibody 4 remains unused since it is inhibited for reaction with the virus antigen 3 by the virus antibody 2 in the liquid phase containing the specimen, and therefore, it can be removed by means of the magnet. However, since the virus antigen 3 is absent in the liquid phase containing a comparative sample, the magnetic-labeled virus antibody 4 reacts with the virus antibody 2, and thus can be detected. As the result, no magnetic-labeled body-specimen complex is detected in the liquid phase containing the specimen, and the magnetic-labeled body-specimen complex is detected only in the liquid phase that contains the comparative sample.

EXAMPLE 1

The specimen prepared according to Preparation Method I (FIG. 2) was measured using the apparatus shown in FIG. 1. A standard solution containing a known amount of the magnetic-labeled body was measured while diluting using an HeNe laser of an output of 5 mW and a low-frequency power source at a cycle of 0.5 Hz. As the result, It was confirmed that the measurement had detecting limit in the order of picogram, which was substantially the same as RIA.

Further, the same procedures as above were repeated except that the application of alternating current magnetic field was not used. The difference between the intensity of scattering of the specimen and that of the comparative sample shown that detection in the order of $10^{-11}$ g/ml was possible.

EXAMPLE 2

The specimen prepared according to Preparation Method II (FIG. 3) was quantitatively determined by the laser beam scattering method described in Example 1 above. As the result, virus antibody in the order of picogram was detected, which was as sensitive as Example 1.

EXAMPLE 3

Various types of influenza virus antibodies and unknown specimen collected from a patient were prepared according to Preparation Method III (FIG. 4), and examination of specimen was performed using the same laser magnetic immunoassay apparatus as used in Example 1 to identify influenza virus.

The assay according to this example showed a high detection sensitivity and therefore enabled identification of influenza virus in a stage of infection much earlier than was identified by the conventional methods using enzymes or fluorescent substances.

EXAMPLE 4

A specimen and a comparative sample were prepared according to Preparation Method IV (FIG. 5) and then were measured by the laser beam scattering method described in Example 1 above. As the result, in this example, the magnetic-labeled virus antigen 2' remained unused since its reaction with the virus antibody 2 was inhibited by the virus antigen 3 in the liquid phase containing the specimen and therefore, removed as is by means of the magnet. However, since the virus antigen 3 was absent in the liquid phase containing the comparative sample, the magnetic-labeled virus antigen 2' reacted with virus antibody 2 and thus was detected. As the result, the magnetic-labeled body-specimen complex was not detected in the liquid phase containing the specimen but the complex was detected only in the liquid phase containing the comparative sample. However, since specimens from patients in the early stage of infection with virus contained the virus antigen 3 in a very small numbers, and since only a part of the immobilized antibody reacted with the virus antigen 3 in the step (b), the magnetic-labeled body-specimen complex was also detected in the liquid phase containing the specimen although the amount of the complex detected decreased with increase in the amount of the virus antigen 3. The amount of the virus antigen 3 could be determined quantitatively based on the decrease in the amount of the complex.

EXAMPLE 5

Test specimen liquid was prepared according to Preparation Method V (FIG. 6) and was measured in the same manner as in Example 4 above.

In this example, too, the same results as in Example 4 were obtained.

In this example, agar or gelatin was used as a support. However, there is no critical difference therebetween; the support may be selected empirically depending on what antigens or antibodies to be immobilized are used in combination.

EXAMPLE 6

Figure 7:
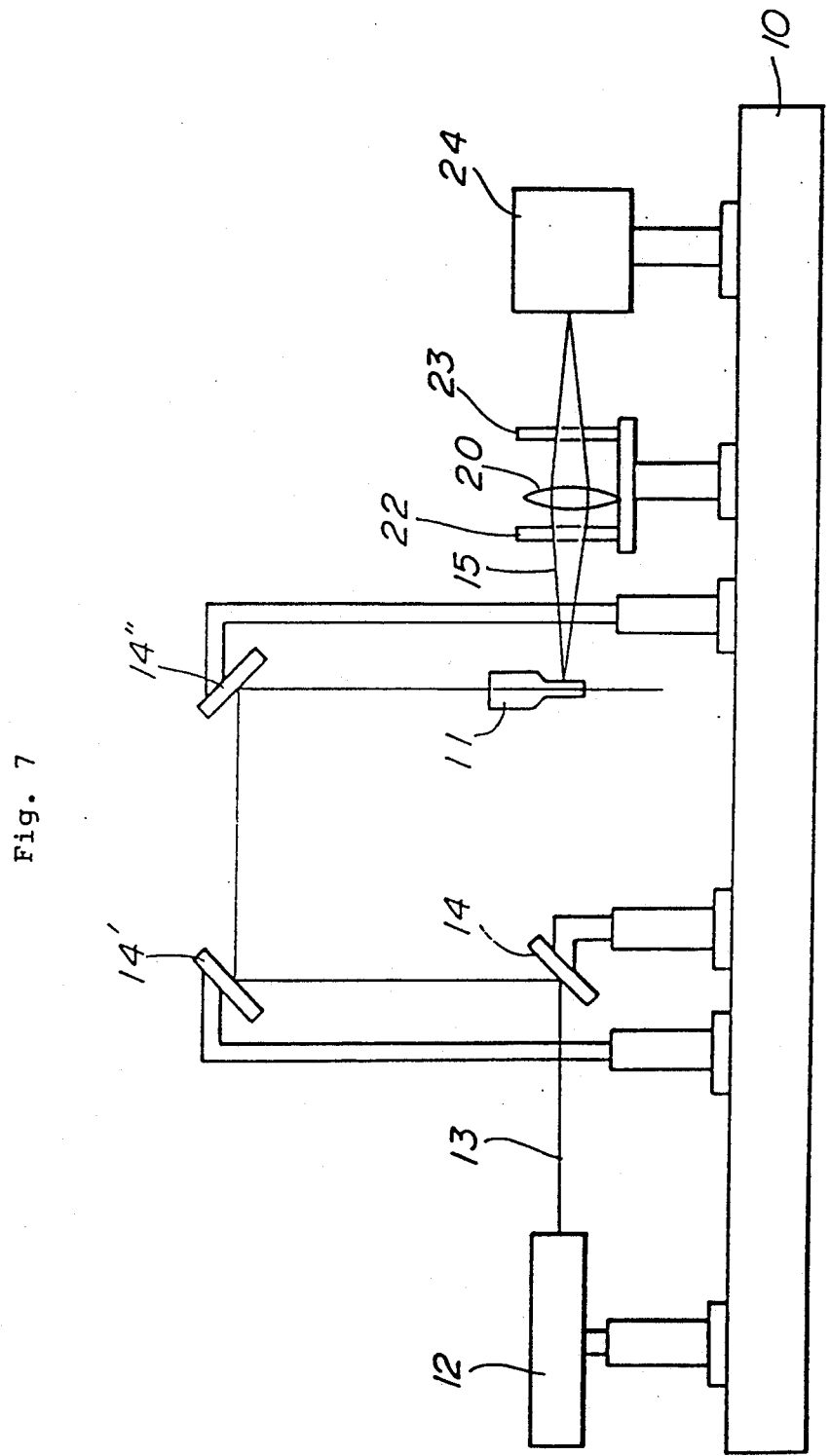
FIG. 7 is a schematical view of a laser magnetic immunoassay apparatus according to one embodiment of the present invention.

FIG. 7 is a schematical side view of an example of the laser magnetic immunoassay apparatus of the present invention. In FIG. 7, of the components of the laser magnetic immunoassay apparatus of the present invention, a magnet driver for guiding and concentrating magnetic micro-particle label and magnetic micro-particle label driving mechanism for periodically control the movement of the magnetic micro-particle label by means of outer magnetic field are not shown.

As shown in FIG. 7, the laser magnetic immunoassay apparatus is provided with an optical stage 10 on which a laser beam source 12, mirrors 14, 14' and 14" which change the light passage of the laser beam 13 from the laser beam source 12. The light passage of the laser beam 12 is changed so that a specimen container 11 is arranged thereon. The specimen container 11 is arranged with the direction of its axis being substantially in alignment with the light passage of the laser beam 13. The container has a different diameter cross-section as described later hereinbelow.

The laser beam 13 is introduced in the direction of the axis of the specimen container 11 as stated above, and it is scattered by a magnetic-labeled body-specimen complex contained in the liquid stored in the specimen container 11. The scattered light is taken out through a small opening portion of the specimen container 11. On a scattered light flux 15 are provided a slit 22, a condenser 20, and an ND filter 23 as well as a photomultiplier 24, which is placed at the position where the scattered light is converged by the condenser 20.

In this example, the specimen container 11 used was a different diameter cross-section container made of pyrex glass having two inner diameters, 8 mm and 0.5 mm. The laser beam was introduced through the larger aperture end of the specimen container 11 and is taken out through the smaller aperture end.

The reason why the different diameter cross-section container was used as a specimen container and the laser beam was introduced through the larger aperture end was as follows. That is, when the aperture of the container is larger than the diameter of the incident laser beam only a part of the specimen contributes to light scattering, resulting in limitation in improving the sensitivity of measurement. On the other hand, if the aperture of the container is substantially the same as the diameter of the laser beam, introduction of the laser beam through the opening of the container as done in this example results in broadening of the incident beam because of the meniscus on the surface of the specimen, which is undesirable from the viewpoint of improvement in the sensitivity of measurement.

Further, it is of course possible to apply a method in which a laser beam is introduced through the side wall of the cell for measurement, as commonly used in conventional light scattering measurement apparatuses. However, when the aperture of the cell for measurement is in the order of several hundreds microns, which is of same level as the diameter of the laser beam, it is necessary to use a matching oil having the same refractive index as the measurement cell in order to efficiently introduce the laser beam into the measurement cell. Thus, the method of introducing laser beams without using a matching oil as in this example is advantageous.

Figure 8:
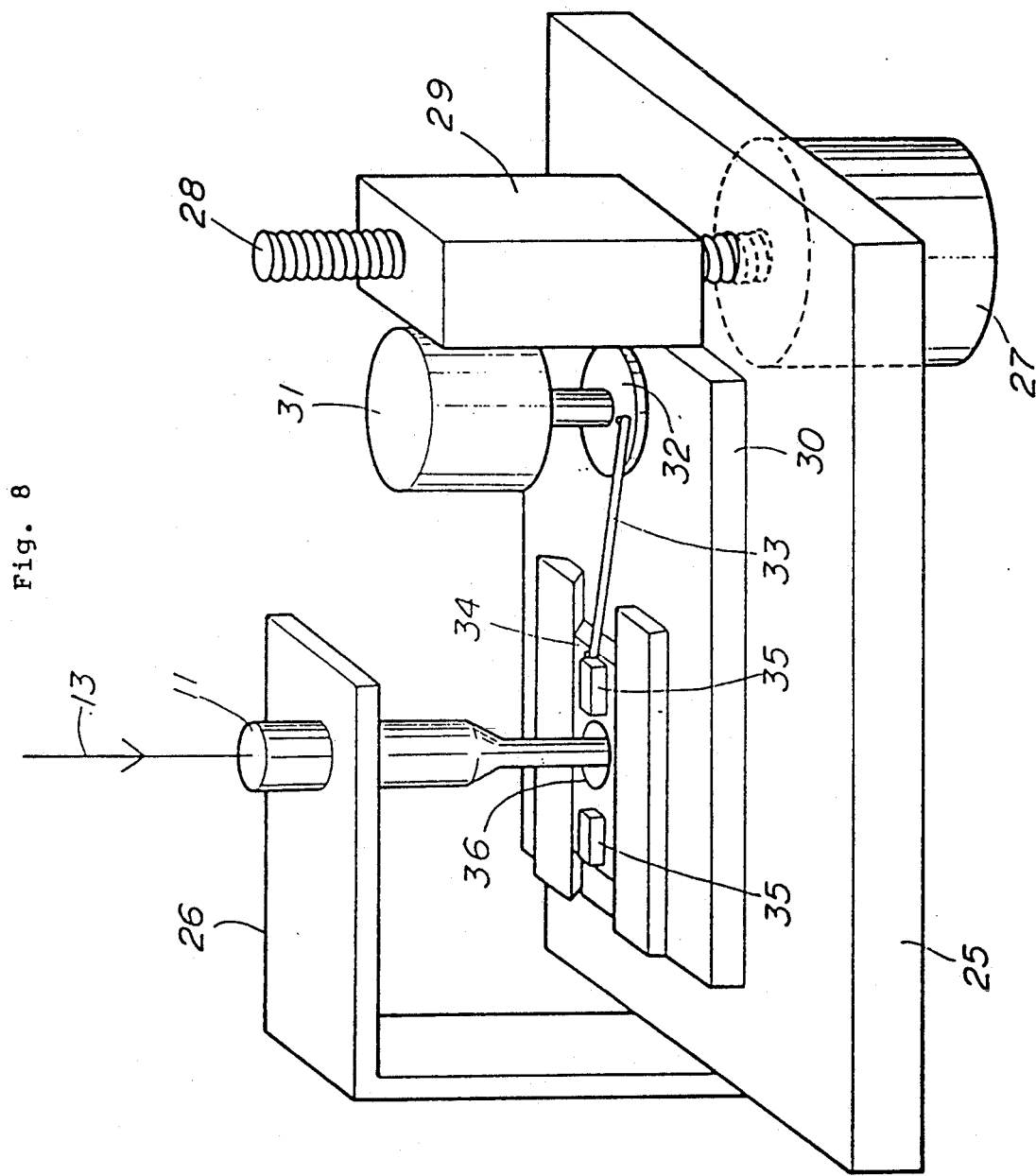
FIG. 8 is a schematical view of a magnet-driving unit for guiding and concentrating micro-particles of a magnetic substance and a driving device for driving the micro-particles of the magnetic substance, which are used in the laser magnetic immunoassay according to the present invention.

FIG. 8 schematically illustrate the magnet driver for guiding and concentrating magnetic micro-particle label, and the magnetic micro-particle label driving mechanism for periodically controlling the movement of the magnetic micro-particle label by means of outer magnetic field.

The magnet driver and ultramicro-particle driving mechanism comprise a fixing stage 25 to which a support base 26 for vertically supporting the specimen container, and a housing 29 for a screw bearing moving up and down in mesh with a feed screw 28 driven by a motor for guiding and concentration, and a movable stage 30 attached to the housing.

As described above, the specimen container 11 is a different diameter cross-section container, and the laser beam 13 is introduced through the larger aperture end. As described later hereinbelow, the smaller aperture end penetrates the movable stage 30. The movable stage 30 is provided with a motor 31, an eccentric cam 32 attached to the shaft of the motor 31, and a guide stage 34 connected to the eccentric cam through a rod 33. The guide stage 34 is slidable reciprocatingly on a track defined by a pair of guide members. Further, the guide stage 34 is provided with a pair of permanent magnets 35 and the opening 36 of the guide stage is positioned between them. The smaller diameter portion of the specimen container penetrates the opening 36. The inner diameter of the opening 36 is constructed to be sufficiently larger than the smaller diameter portion of the specimen container so that the smaller diameter portion of the specimen container will not collide against the guide stage 34 when the guide stage 34 is in reciprocation movement.

Then, explanation will be given on the operation of the magnet driver for guiding and concentrating label magnetic micro-particles and the label magnetic micro-particle driving mechanism for periodically controlling the movement of the label magnetic micro-particles in the laser magnetic immunoassay apparatus of the present invention shown in FIG. 8.

Firstly, the specimen container 11 is attached to the support for the specimen container, and the motor for driving and concentrating the label magnetic micro-particles is actuated to elevate the housing 29, more particularly the movable stage 30 attached to the housing 29, from the smaller aperture side to the larger aperture side of the specimen container. Then, the movable stage 30 is lowered to the smaller aperture side of the specimen container at a low speed of 5 mm/minute by means of the motor 27 until the movable stage 30 reaches the position of guiding and concentrating the label magnetic micro-particles, the position being in in alignment with the light axis of scattered light detection of the optical system comprising the slit 22, the lens 20, the ND filter 23, the photomultiplier 24 as illustrated in FIG. 7, at which position the movement of movable stage 30 is stopped. With this operation, the label magnetic micro-particles dispersed uniformly in the specimen container are collected around a pair of the permanent magnets 35 while the magnets move and are concentrated at a portion, i.e., the smaller aperture portion, of the specimen container on the light axis of scattered light detection.

Subsequently, the guide stage 34 mounting thereon a pair of the permanent magnets 35 fixed sandwiching the specimen container 11 at a distance of 12 mm therefrom is moved in reciprocation at a stroke of 5 mm and a movement speed of 300 mm/minute by means of the motor 31 for controlling the movement, the eccentric cam 32 and the rod 33. This operation gives rise to movement of the concentrated label magnetic micro-particles within the smaller diameter portion in synchronization with the reciprocating movement of the permanent magnets 35.

Figure 9:
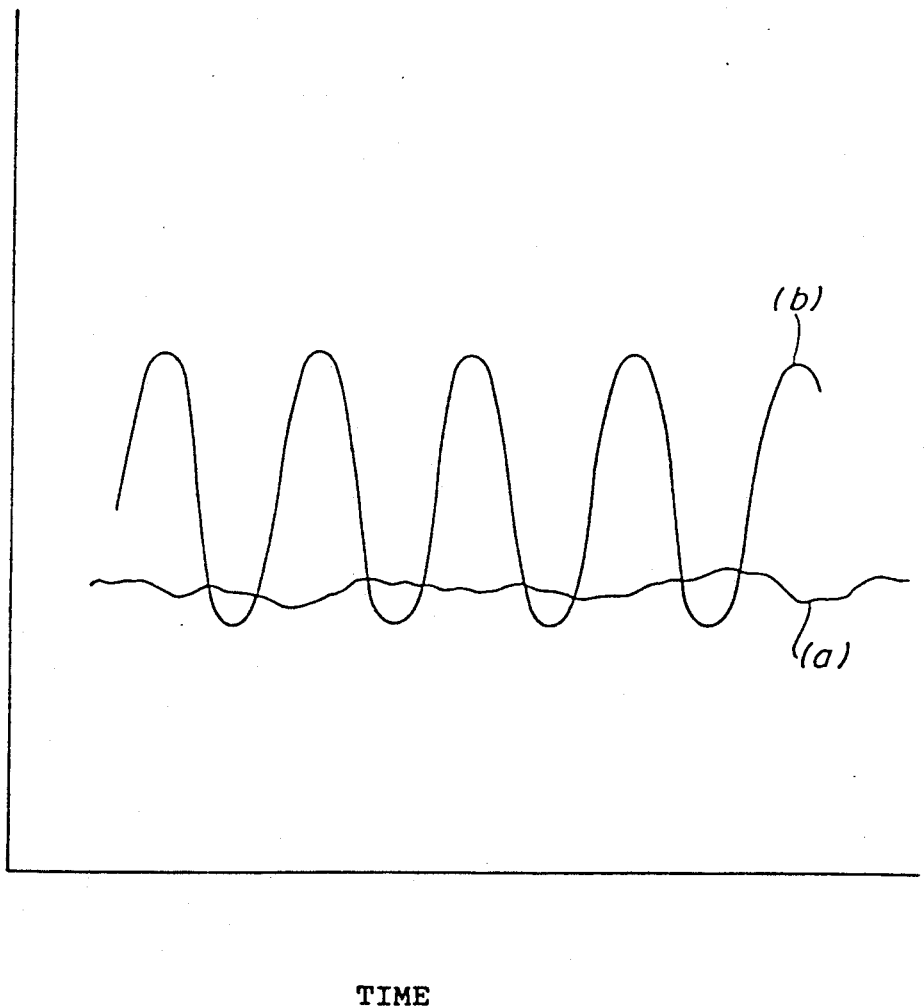
FIG. 9 is a graph plotting (a) the intensity of scattered beam measured without giving micro-particles of a magnetic substance a periodical movement in contrast to (b) the intensity of scattered beam measured with giving the micro-particles of the magnetic substance a periodical movement according to the present invention.

FIG. 9 illustrates variation in the intensity of scattered light from the micro-particles measured by means of the photomultiplier 24 shown in FIG. 7.

FIG. 9 also shows the results obtained when the permanent magnets were at a standstill under symbol (a). In this case, only irregular variation in the intensity due to Browninan movement of the micro-particles was observed.

On the other hand, the results obtained when the permanent magnets 35 were moved in reciprocation, which are shown in FIG. 9 under symbol (b). As shown in FIG. 9, when the reciprocating movement of the permanent magnets 35 was given, variation in the intensity of the scattered light observed is in synchronization with the period of the reciprocating movement. Detection of the scattered light in synchronization with the reciprocating movement using a lock-in amplifier confirmed that improvement in the sensitivity of measurement by two figures was attained, thus enabling ultramicro measurement in the order of picogram.

EXAMPLE 7

Figure 10:
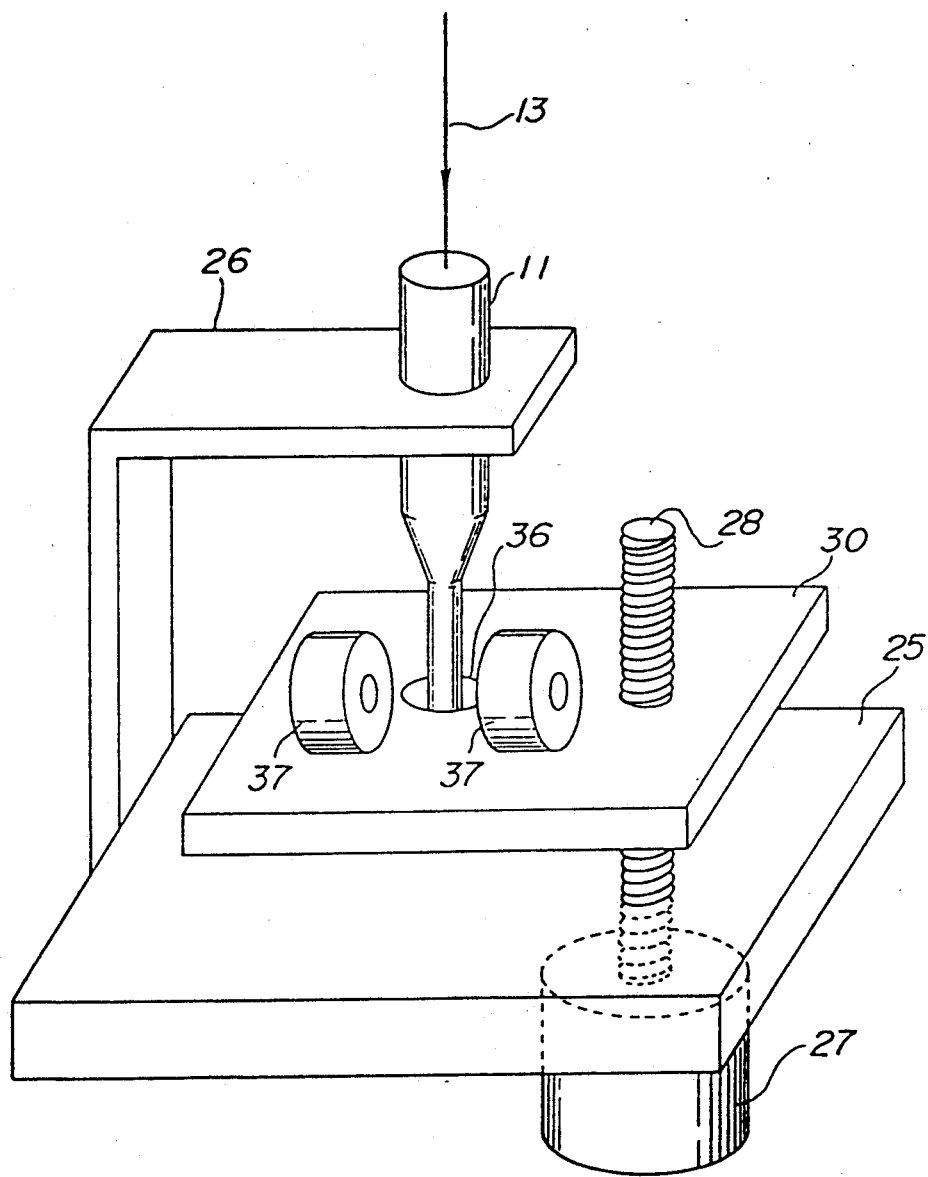
FIG. 10 is a schematical view of a magnet-driving unit for guiding and concentrating micro-particles of a magnetic substance and a driving device for driving the micro-particles of the magnetic substance, which are used in a laser magnetic immunoassay according to another embodiment of the present invention.

FIG. 10 is a schematical view illustrating the magnet driver for guiding and concentrating label magnetic micro-particles and the label magnetic micro-particle driving machanism for periodically controlling the movement of the label magnetic micro-particles by means of outer magnetic field, according to the second embodiment of the present invention. In FIG. 10, those members which are the same as or correspond to those shown in FIG. 8 have the same reference numerals, respectively.

In this example, the magnet driver for guiding and concentrating the label magnetic micro-particles is provided with a fixing stage 25, a motor 27 for guiding and concentration attached to the fixing stage 25, and a movable stage 30 which is in mesh directly with a feed screw 28 driven by the motor 27. An opening 36 is provided on the movable stage 30 through which the smaller aperture portion of the specimen container 11 penetrates, and on the both sides of the opening 36 are provided a pair of electromagnets 37, thus forming a label magnet micro-particle driving machanism.

Difference is that in contrast to the first embodiment shown in FIG. 8 which uses permanent magnets, this example shown in FIG. 10 uses the electromagnets 37 and the label magnetic micro-particle driving mechanism which lacks movable portion and drives microparticles electrically. In this example, guiding and concentration as well as control of the movement of the micro-particles by alternatingly energizing the pair of electromagnets.

That is, upon guiding and concentration, the movable stage 30 is moved up and down in the same manner as in Example 6 under the conditions of simultaneously exciting the both electromagnets 37 to guide and concentrate the micro-particles to a predetermined position within the smaller aperture portion of the specimen container 11. Subsequently, alternating excitation of the electromagnets is performed at the position of concentration. The label magnetic micro-particles thus-concentrated come to move periodically within the smaller aperture portion of the specimen container 11 in synchronization with the period of excitation. Although the period of excitation varies depending on the magnetic field of the electromagnets, the distance between the specimen container and the electromagnets, configuration of the specimen container, etc., 1 Hz or so was suitable in this example. The optical system used was the same as used in the first embodiment.

EXAMPLE 8

Figure 12:
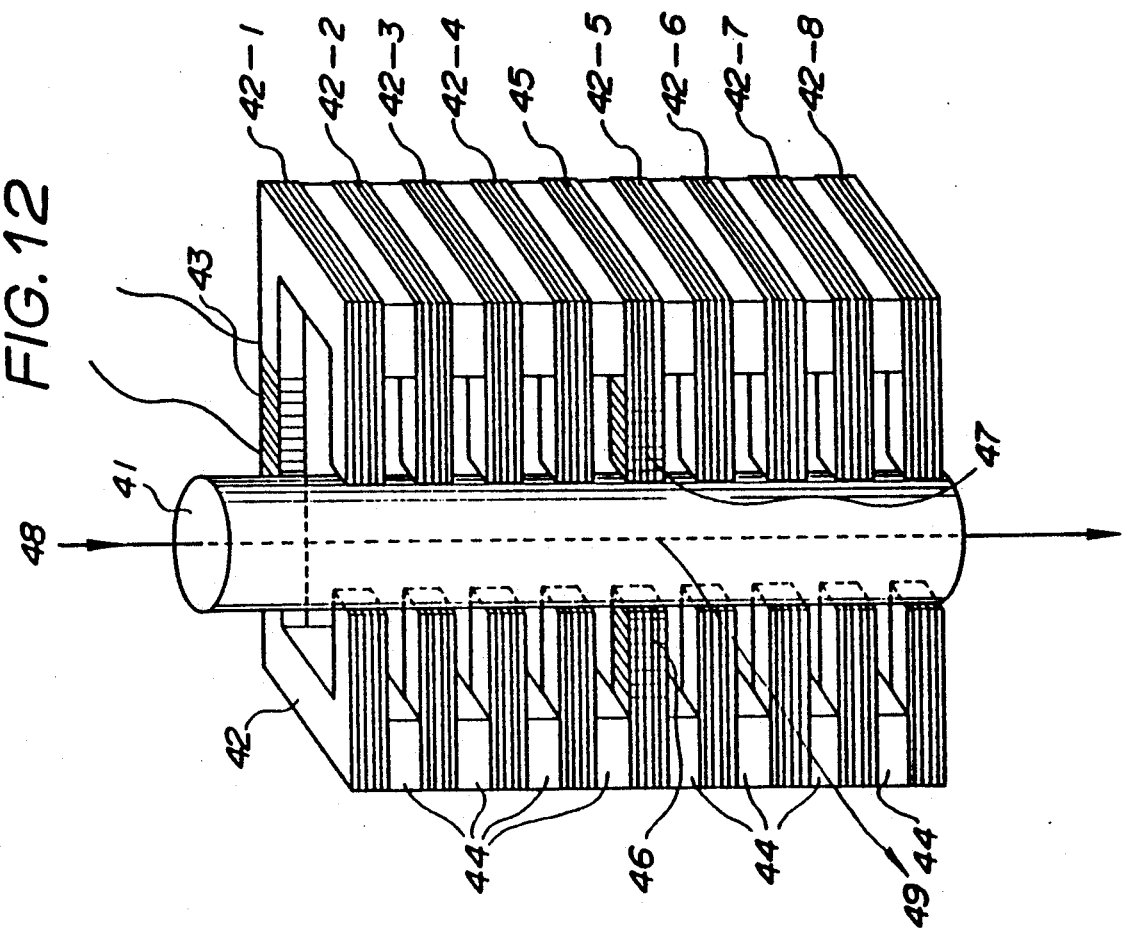
FIG. 12 is a schematical view of a magnet-driving unit for guiding and concentrating micro-particles of a magnetic substance and a driving device for driving the micro-particles of the magnetic substance, which are used in the laser magnetic immunoassay according to still another embodiment of the present invention.

FIG. 12 is a schematical view illustrating the magnet driver for guiding and concentrating label magnetic micro-particles and the label magnetic micro-particle driving mechanism for periodically controlling the movement of the label magnetic micro-particles by means of outer magnetic field, according to still another embodiment of the present invention.

The apparatus of this example has an iron core portion which comprises alternatingly superimposed one after another an iron core 42 composed of laminated silicon steel plates for guiding and concentrating the label magnetic micro-particles and a spacer 44 made of aluminum which is non-magnetic. The iron cores 42 and spacers 44 together as a whole form C-shape, and in the space defined thereby is arranged a specimen container 41. Iron cores 42-1, 42-2, . . . 42-8 each are wounded therearound a coil 43, thus forming an electromagnet. Further, the iron core 45 positioned approximately in the center of the laminates of the iron core 42 is wound therearound coils 46 and 47 on the both side portions thereof sandwiching the specimen container 41. In this example, the specimen container 41 used is a glass tube having an inner diameter of 2.0 mm and an outer diameter of 2.8 mm. The iron core for guiding and concentrating the label magnetic micro-particles is composed of eight layers 42-1 to 42-8, and one layer of the iron core 45 for controlling the movement of the label magnetic microparticles is provided at the central portion thereof.

Figure 13A:
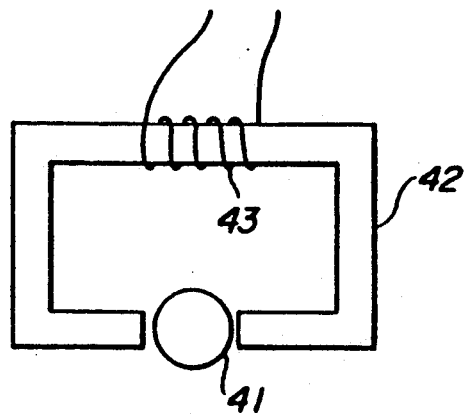
FIGS. 13 (a), 13(b) and 13(c) each are a cross-sectional view of the apparatus illustrated in FIG. 12.
Figure 13B:
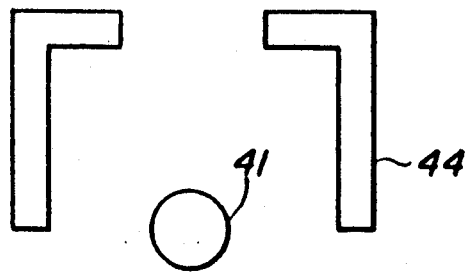
Figure 13C:
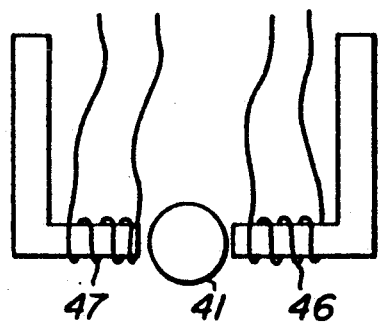

FIG. 13 (a) shows a cross-sectional view of the iron core 42 for guiding and concentrating the label magnetic micro-particles, FIG. 13 (b) is a cross-sectional view of the spacer 44, and FIG. 13 (c) is a cross-sectional view of the iron core 45 for guiding and concentrating the label magnetic micro-particles. The iron core 42 for guiding and concentration is wound therearound the coil 43 at one position and the iron core 45 for controlling the movement is wound therearound the coils 46 and 47.

Figure 11:
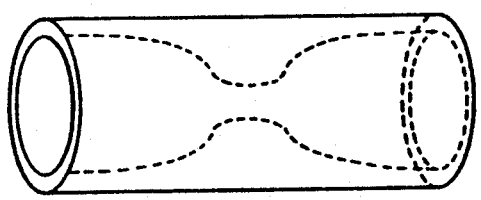
FIG. 11 illustrates a specimen container used in a preferred embodiment of the present invention.

The apparatus shown in FIG. 12 is arranged in the scattered light measurement portion of the laser magnetic immunoassay apparatus of the present invention shown in FIG. 7, more particularly, in such a manner that the axis of the specimen container 41 overlaps the light axis 48 of the incident laser beam. In addition, although the specimen container 41 used in the apparatus shown in FIG. 12 is a glass cell having the same inner diameter, that which has a shape shown in FIG. 11 is also preferred. In FIG. 12, the axis of detecting the scattered light is shown by reference numeral 49.

Figure 14:
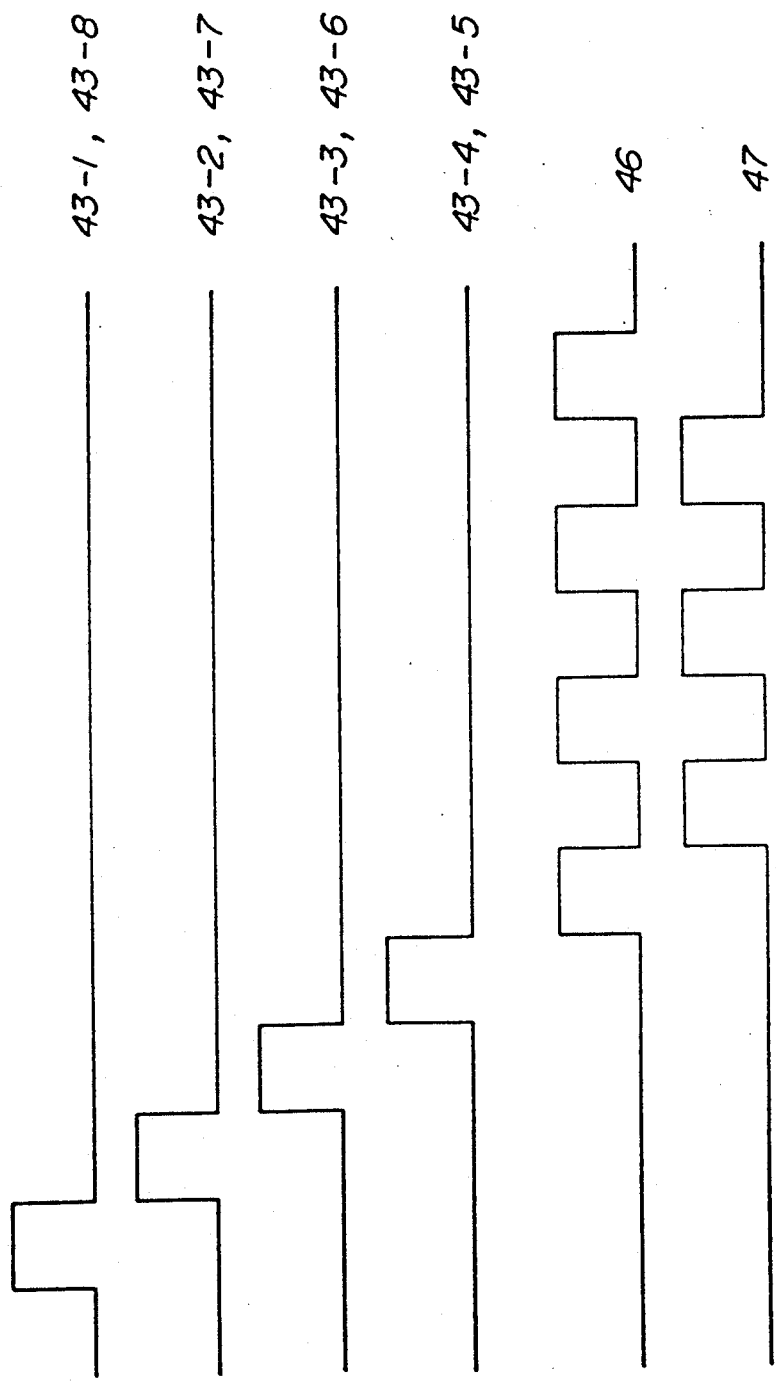
FIG. 14 illustrates timing for energizing an electromagnet in the apparatus shown in FIG. 12.

FIG. 14 is a diagram showing the timing of exciting the electromagnets shown in FIG. 12. Assuming the coils wound around the iron cores 42-1 to 42-8 for guiding and concentration are assigned reference numerals 43-1 to 43-8, respectively, excitation occurs sequentially starting from the outermost electromagnet, thus guiding and concentrating the label magnetic micro-particles in the sepcimen container 41 to the position of the iron core 45 for controlling the movement thereof. Then, the pair of electromagnets 46 and 47 for the iron core 45 are alternatingly excited to give the label magnetic microparticles a periodical movement.

As the result of the measurement of detection sensitivity conducted by incorporating the apparatus shown in FIG. 12 into the laser magnetic immunoassay apparatus of the present invention shown in FIG. 7, it was confirmed that detection in the order of picogram could be performed which is as sensitive as attained by similar apparatus with permanent magnets shown in FIG. 8.

Comparing with the apparatus using permanent magnets shown in FIG. 8, the apparatus of this example is advantageous in view of reduction in size and prolonged service life since it does not include mechanical parts. On the other hand, in the apparatus using permanent magnets shown in FIG. 8, it is possible to use magnets having large energy product such as rare earth Co magnet while in the appratus of this example, it is desirable to use a specimen container having a small crosssection in order to exhibit effects of the present invention since the intensity of the magnetic field is low.

Further, the iron cores 45 for controlling the movement of the label magnetic micro-particles are placed in the central portion in this example. However, it does not have to do so, and it may be placed at any desired position. In addition, although the iron cores 42 for guiding and concentrating the label magnetic microparticles is disposed as opposing each other and sandwiching the sepcimen container in this example, it is also possible to arrange them only on one side of the specimen container. However, it is desirable to arrange the iron core 45 for controlling the movement so as to oppose each other as sandwiching the specimen container since greater amount of deviation of the label magnetic micro-particles is more advantageous for the control of the variation in the intensity of scattered light.

EXAMPLE 9

Figure 15A:
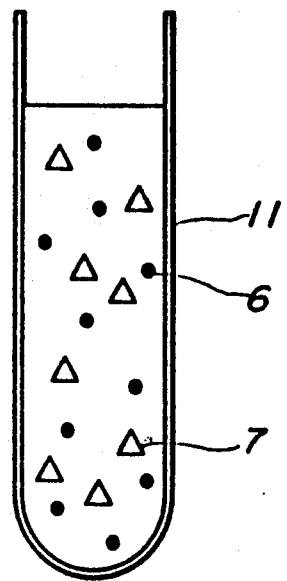
FIGS. 15 (a), 15(b) and 15(c) are views illustrating separation treatment according to the present invention for separating floating matters from a liquid phase specimen.
Figure 15B:
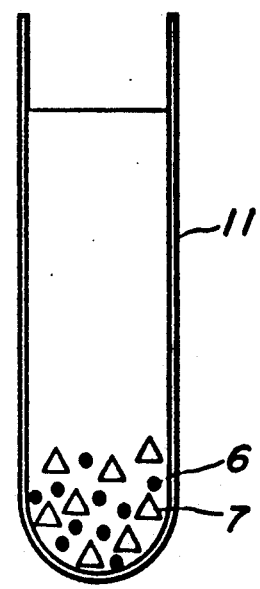
Figure 15C:
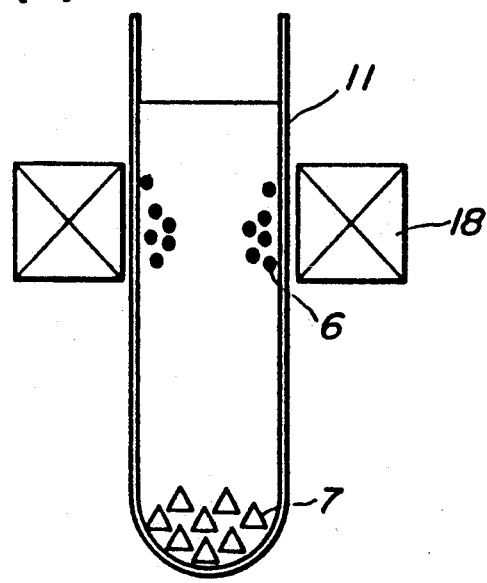

FIGS. 15 (a) to (c) illustrate pretreatment for the immunoassay according to the method of the present invention applied to each liquid phase magnetic-labeled body-specimen complex prepared as in Preparation Method I.

FIG. 15 (a) shows each magnetic-labeled body-specimen complex prepared as described above, immediately after being dispersed in water to fluidize and stored in a glass cell 11 having an inner diameter of 2.0 mm and an outer diameter of 2.8 mm. In the drawing, 6 with a symbol " " indicates magnetic-labeled body specimen-complex, and 7 with a symbol "Δ" designates unnecessary floating matters mainly composed of fragments of the immobilized support after pulverization.

After subjecting these samples to centrifugation at a rotation of 4,000 rpm for 3 minutes, all the floating matters including the magnetic-labeled body-specimen complex precipitated on the bottom of the glass cell 11 as shown in FIG. 15 (b).

Then, a pair of rare earth metal permanent magnets 18 were positioned so as to sandwich the glass cell 11, and they were moved from the lower to the upper of the glass cell 11 until the sample 6 containing the magnetic-labeled body-specimen complex is guided near the central portion in the height of the glass cell 11. By so doing, essentially the magnetic-labeled body-sepcimen complex 6 alone was guided upwards.

Figure 16:
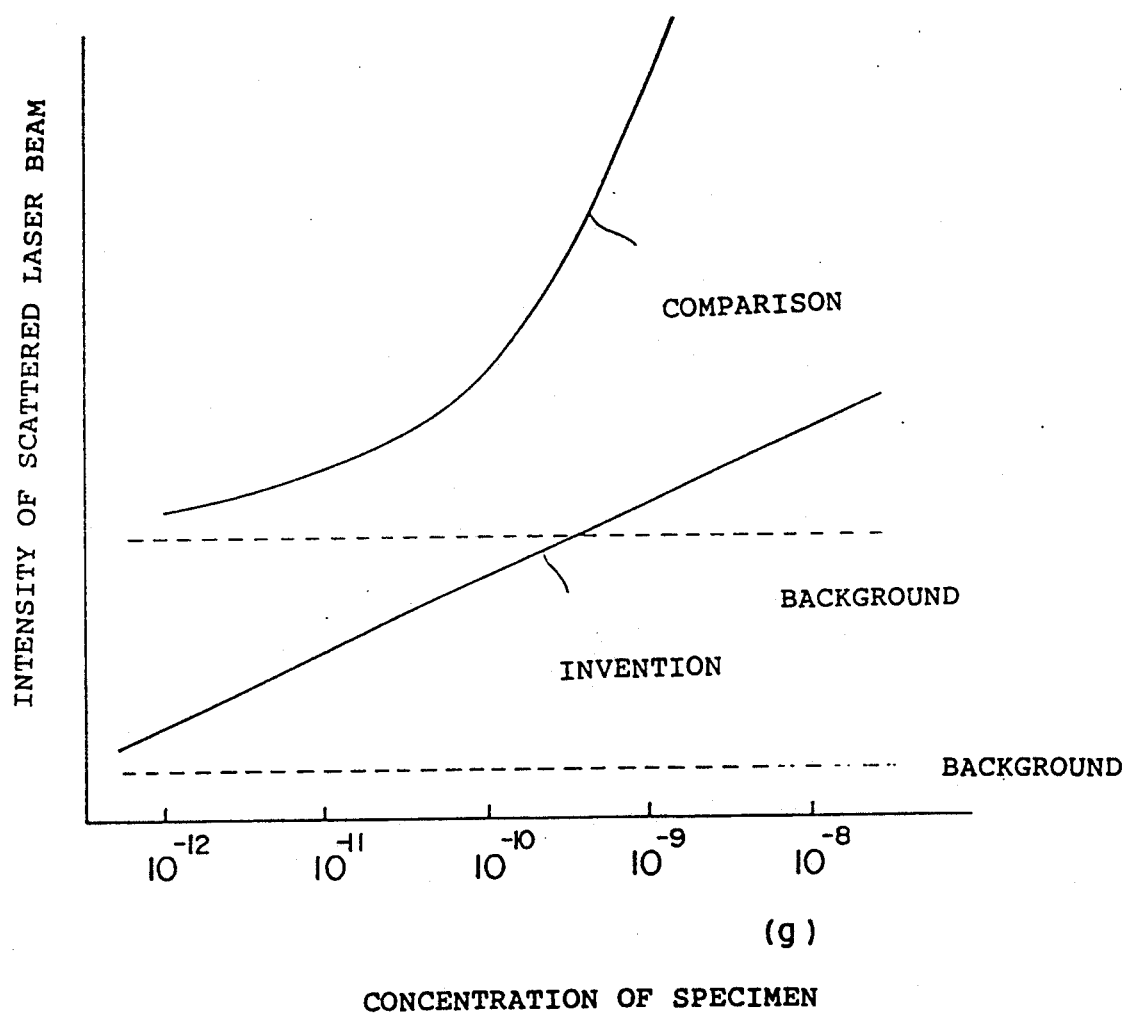
FIG. 16 is a graph showing relationship between the concentration of a specimen and the intensity of scattered light measured according to the method of the present invention.

FIG. 16 is a graph showing the results of immunoassay of a plurality of samples obtained by regularly varying their concentration, in procedures described later hereinbelow. The graph also describes the results of measurements in which the precipitation operation of the above-described floating matters and guiding operation of the sample were omitted.

As shown in FIG. 16, when the above-described operations were omitted, the intensity of the scattered laser beam increased excessively with increase in the concentration of the magnetic-labeled body-specimen complex. Therefore, this method does not enable quantitative measurement although it makes it possible to confirm if the specimen is present.

In contrast, the method of this invention gives rise to good linearity of detection accuracy, enabling detection of variation in the intensity of scattering in an accurate proportion to the concentration of the specimen.

Further, in FIG. 16, what is shown by dotted line together with the results of each detection is the level of each background corresponding to each detection limit. That is, in the method of the present invention, background is very low and detection limit is about twice that of the comparative method.

Figure 17:
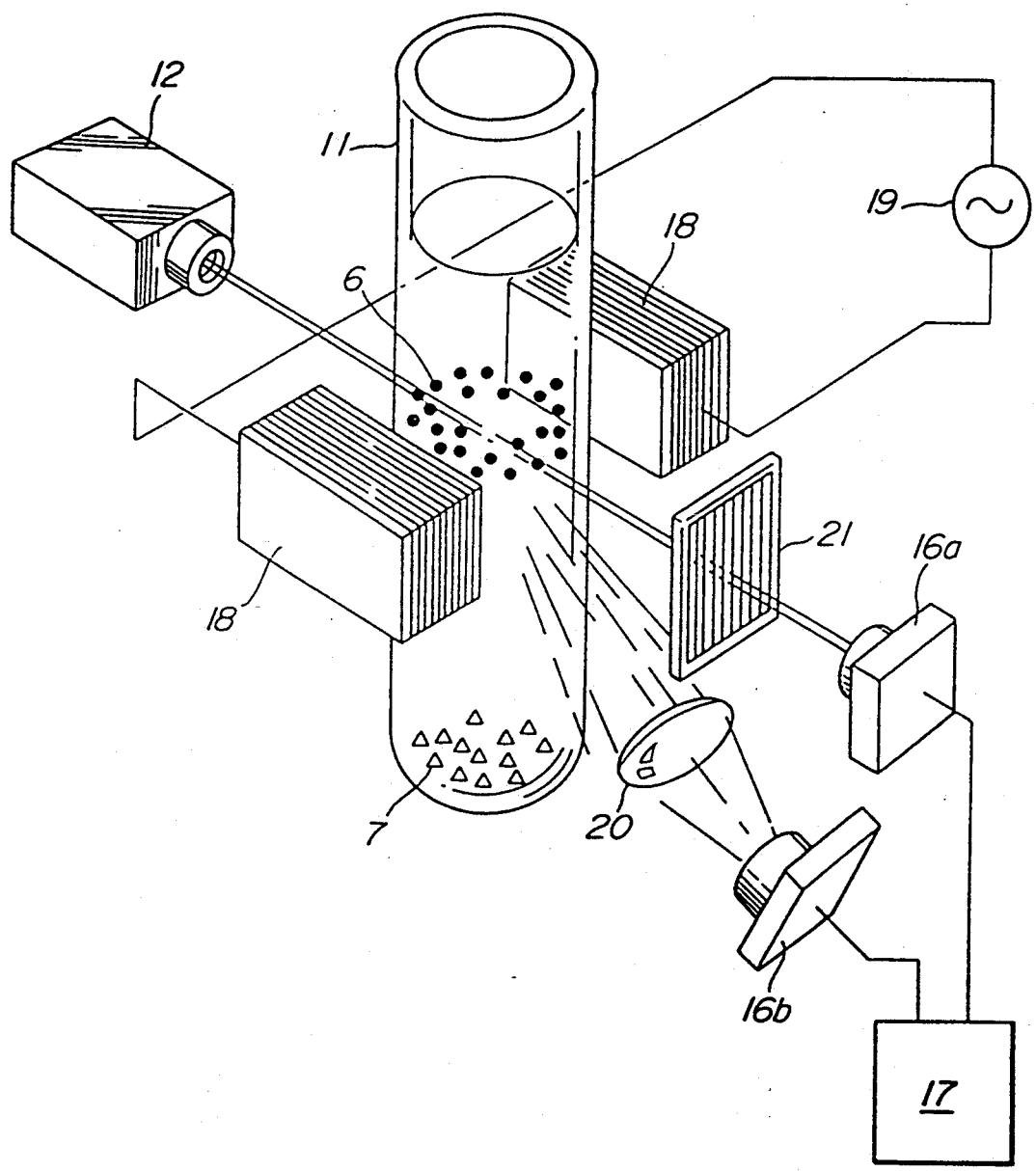
FIG. 17 is a schematical illustration for indicating a quantitative measurement of a specimen by means of laser beam scattering according to the present invention.

The measurement of the magnetic-labeled body in the liquid phase specimen by laser beam scattering was as described hereinbelow. FIG. 17 illustrates this method schematically.

On the side of the glass cell 11 storing a specimen liquid prepared for test are arranged a pair of electromagnets 18 so as to sandwich the glass cell 11. The electromagnets 18 serve to hold the magnetic labeled body-specimen complex separated from other floating matters 7 which precipitated in the glass cell 11 at a central position in the height of the glass cell. The electro-magnets 18 may also be used for separating the floating matters 7 and the magnetic-labeled body-specimen complex 6 from each other. The electromagnets 18 are driven by an alternating current power source 19 of a low-frequency as low as 0.5 Hz, and the magnetic field generated varies in accordance with the frequency of the power source.

On the other hand, the magnetic-labeled body-specimen complex 6 held in the middle of the glass cell 11 by means of the electromagnets 18 is radiated with a laser beam of 5 mW by means of He-Ne laser tube 12 from the side of the glass cell 11.

As for the laser beam, a first photo diode 16a is arranged through the polarizer 21 on the extention of the laser beam axis crossing the glass cell 11 through. A second photo diode 16b is arranged at a position deviated from the light axis of the laser beam so that the floating matters 7 should not intervene between it and the magnetic-labeled body-specimen complex 6, or that the condenser lens 20 is sandwiched between it and the glass cell 11. The photo diodes 16a and 16b output electric signals which correspond to incident light by means of the lock-in amplifier 17 which is operated in synchronization with the alternating current power source 19 for the above-described electromagnets 18.

In the apparatus described as above, within the glass cell 11, the magnetic-labeled body-specimen complex 6 is concentrated in the magnetic field formed by the electromagnets 18 to enhance the concentration of the specimen locally. Therefore, the laser beam radiated to a host of the magnetic-labeled body-specimen complexes 6 is scattered depending on the concentration of the complexes.

The first photo diode 16a measures the intensity of the laser beam which passed through a host of the magnetic-labeled body-specimen complexes 6, and the second photo diode 16b measures the intensity of scattered light scattered by a host of the complexes 6. Ordinarily, measurements can be well performed with scattered light only. However, transmitted light enables detection with higher S/N ratio depending on the kind and concentration of the specimen.

In this case, as described above, since the electromagnets 18 are driven by the alternating current power source 18, the magnetic field generated by the electromagnets varies accordingly, and the group of the magnetic-labeled body-specimen complex trapped by the magnetic field oscillate as well. On the other hand, the action of each photo diode is synchronized with the variation in the magnetic field by means of the lock-in amplifier 17 and therefore, each photo diode selectively detects only the variation in the intensity of the laser beam due to the magnetic-labeled body-specimen complex 6 trapped by the magnetic field. With these operations, influences due to change in temperature, disturbances from outside or the like can be avoided, thus enhancing the detection accuracy further.

Upon measurement of background level of the specimen container through the lock-in amplifier by measuring comparative samples not containing the magnetic-labeled body-specimen complex prepared according to the above-described procedures, it revealed that a detection limit in the order of picogram which is substantially as sensitive as RIA method has been attained. With the concentrating step alone without using alternating current magnetic field, detection in the order of $10^{-11}$ g/ml could be effectively performed.

EXAMPLE 10

FIGS. 18 (a) to (h) sequentially illustrate the operations of preparing test specimen liquid in the laser magnetic immunoassay of the present invention. The operations described herein are to immobilize a known antibody on the surface of non-magnetic particles and subject the product to an antigen-antibody reaction with an unknown antigen, and thereafter, further subject to the resulting complex to an antigen-antibody reaction with a specific antibody labeled with micro-particles of a magnetic substance.

FIGS. 18 (a) and (a)' are cross-sectional and plan views, respectively, of a specimen container. FIG. 18 (b) et seq. are drawings representing views from the same visual point. The specimen container 11 is a container which has side walls of a height L defining a storage portion. The container is provided in the inside thereof with two partition walls a and b of a height of l smaller than L to divide it into three storage portions. As shown in FIG. 18 (a), the storage portion serves as three independent wells A, B and C linked to each other for contents not higher than the height l, and when a liquid is filled above the height l, the wells are communicated to each other near the level of the water surface. In the following operations, the wells A, B, and C are used as a well for an antigen-antibody reaction, a well for separation of unused magnetic-labeled body, and a well for collection of specimen, respectively.

A liquid having dispersed therein known antibody 12 fixed to non-magnetic particle was filled in the well A of the specimen container 1 to the height not higher than l, as shown in FIG. 18 (b). The non-magnetic particle used is a polystyrene latex of an average particle size of 0.5 μm.

Subsequently, as shown in FIG. 18 (c), a specimen collected from body fluid of a patient was injected into a well A with a micro-syringe 8a. In the liquid injected contained an unknown virus antigen 53, which formed together with an antibody 52 an antigen-antibody complex as a result of an antigen-antibody reaction.

Further, as shown in FIG. 18 (d), a specific antibody 54 labeled with micro-particles of a magnetic substance 55 was injected into the well A with a micro-syringe 8b. Anti-immunoglobulin was used as the specific antibody. The thus-injected specific antibody 54 underwent an antigen-antibody reaction with the above-described antigen-antibody complex.

Thus, the following substances coexisted in the well A1.

(1) Complex of "non-magnetic particle 51-antigen 52-antibody-53-specific antibody 54-micro-particles of magnetic substance 55".
(2) Unused "specific antibody 54-micro-particles of magnetic substance 55".
(3) Unused "non-magnetic particle 51-antibody 53".
(4) Inevitably contained impurity particles.

As shown in FIG. 18 (e), purified water was poured into wells B and C with a divider 9 to elevate the level of water higher than l.

In this state, as shown in FIG. 18 (f), when a magnet 5L with weak magnetic force was moved closer to above the well A, the above-described (2) alone was attracted by the magnet 5L. Then, (2) in the well A was guided to the well B by moving the magnet 5L horizontally toward the well B. At this moment, (1) was not attracted by the magnetic force of the magnet 5L since its mass increased due to the non-magnetic particle 51 attached threreto. Therefore, (1), (3) and (4) remained in the well A. In this case, a porous filter can be provided on the upper end of the partition wall between the wells A and B so that the total height becomes above the liquid surface in order to pass (2) therethrough but not (1) and (3), thus ensuring separation. Further, the magnet 5L may be immersed under the liquid surface in the region of the well B so that collection of (2) can be performed effectively (FIG. 18 (f)').

Subsequently, as shown in FIG. 18 (g), a magnet 5H having a sufficiently strong magnetic force was moved closer to the well A. This time, since the magnetic force of the magnet 5H was sufficiently strong, (1) was attracted by the magnet. Therefore, movement of the magnet 5H toward the well C results in that only (1) was guided into the well C.

In this manner, purified water having dispersed therein only complex of "non-magnetic particle 51-antigen 52-antibody 53-specific antibody 54-micro-particles of magnetic substance 55" formed as a result of an antigen-antibody reaction was obtained in the well C of the specimen container 11. Then, this was taken out using a micro-syringe 8c or a like and subjected to measurement by laser beam scattering to detect an antigen-antibody complex.

Further, as described later hereinbelow, the prepared specimen as is in the specimen container 11 can be subjected to measurement by laser beam scattering.

In the operation shown in FIG. 18 (e), it is preferred to pour purified water from the side of the wells B and C since improvement in the detection limit or detection accuracy will be prevented if unused magnetic-labeled specimen or unused micro-particles in the well A, or further, various floating matters inevitably contained in the liquid flow into the wells B or C. For the same reason, it is preferred to guide particles containing micro-particles of the magnetic substance by means of magnetic force only in the vicinity of the water surface of each well.

Further, in the operation shown in FIG. 18 (g), it is preferred to use another magnet in order to guide unused micro-particles of the magnetic substance, which has been guided to the well B by the operation shown in FIG. 18 (f), to the bottom of the well B so that they are set aside.

Laser beam scattering measurement on the specimen prepared as described above was performed as follows. That is, FIG. 19 illustrates this operation.

Figure 19:
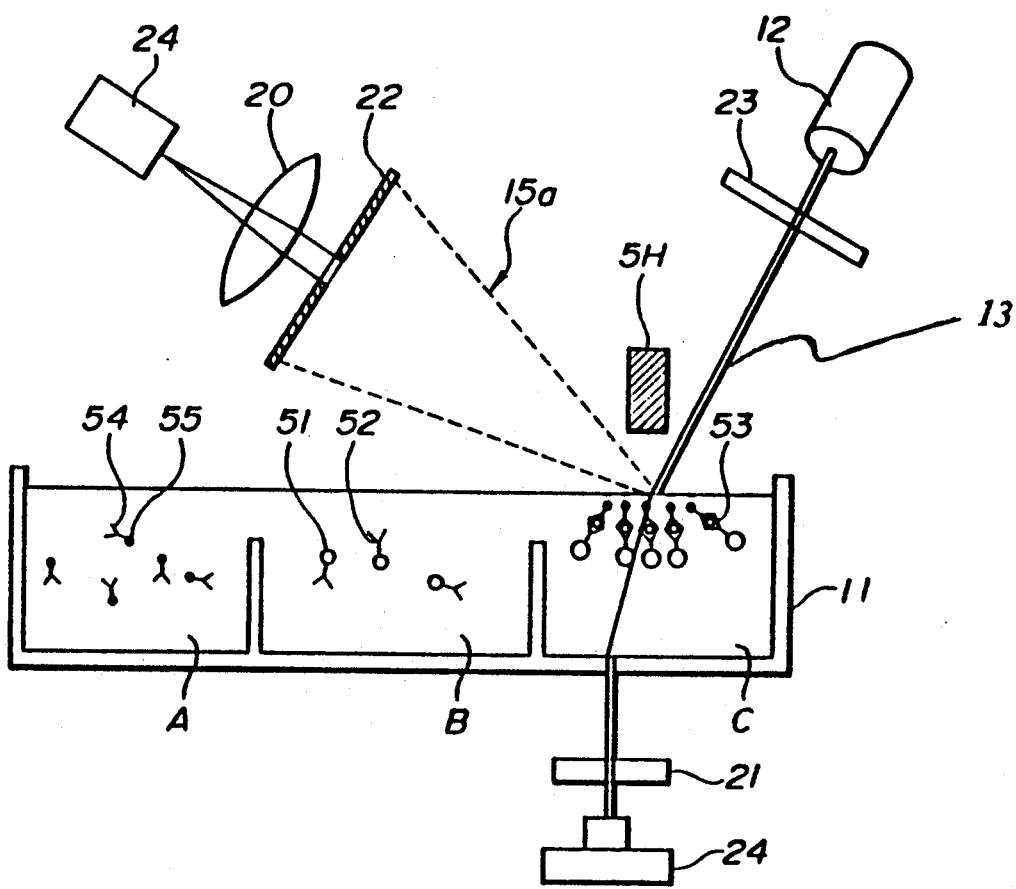
FIG. 19 illustrates measurement with laser beam scattering and transmitting applied to the specimen prepared according to the method illustrated in FIG. 18.
Figure 20A:
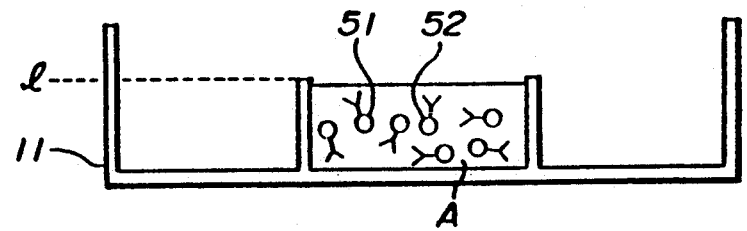
FIGS. 20 (a) to 20(e) illustrate preparation of a specimen upon a laser magnetic immunoassay according to another embodiment of the present invention.
Figure 20B:
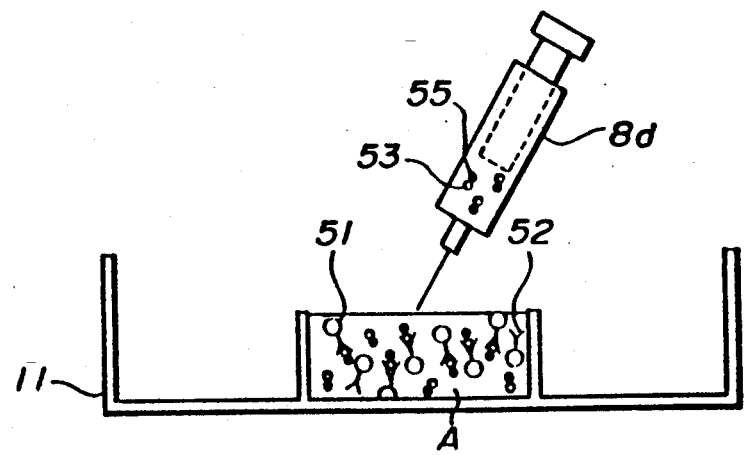
Figure 20C:
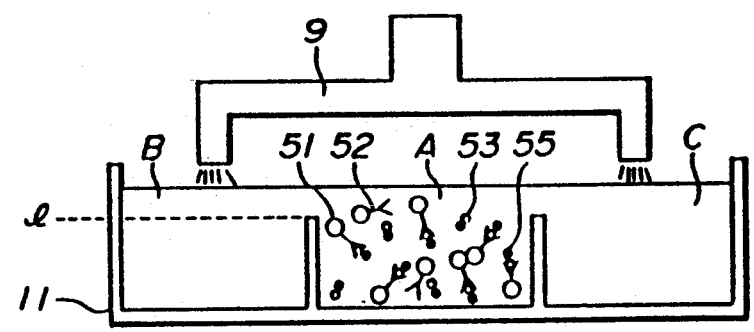
Figure 20D:
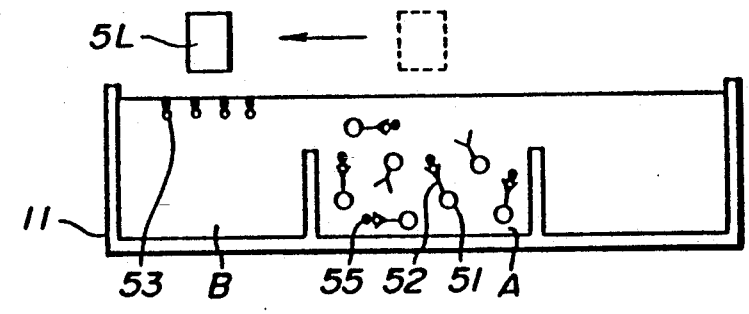
Figure 20E:
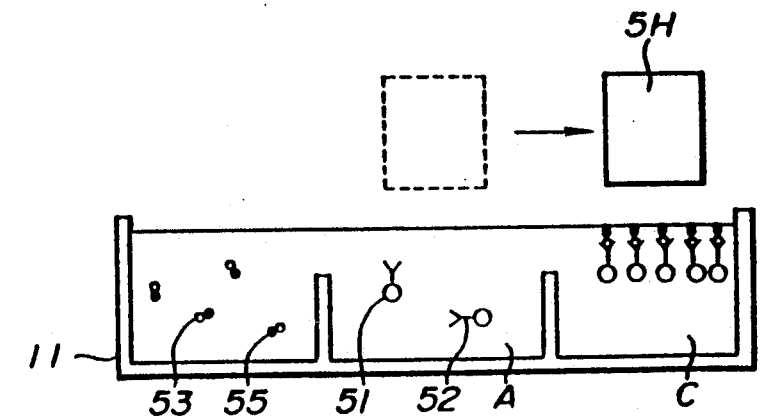

The specimen shown in FIG. 19 is under the same conditions as in FIG. 18 (b). Therefore, the purified water in the specimen container 11 contained dispersed therein unused antibody 53 and non-magnetic particle 51 to which the unused antibody 53 is attached in the well A, unused antibody 54 labeled with micro-particles of the magnetic substance 55 in the well B, and antigen-antibody complex after reaction (51-52-53-54-55) in the well C. Further, the antigen-antibody complex (51-52-53-54-55) in the well C was came together thickly near the water surface by means of the magnet 4.

While keeping such conditions, the laser beam 13 was radiated from above to the region crowded with the antigen-antibody complex (51-52-53-54-55) using He-Cd laser tube 12. Most of the radiated laser beam 13 was transmitted through the purified water in the well C and went out below the specimen container, with a part of the beam being scattered by the antigen-antibody complex (51-52-53-54-55) in the purified water.

The methods for measuring scattering of the laser beam 13 divide roughly into two, one is a method in which the intensity of scattered light 15a at a position deviated from the light beam axis, and another a method in which a polarizer 21 is arranged on the axis of the radiated laser beam so that the laser beam is extinguished when no scattering of the laser beam occurs and the intensity of the scattered light which passed through the polarizer 21. In each case, light receiving elements and the like are arranged at appropriate positions. FIG. 19 shows the both methods together.

A light receiving element 24 shown is one for measuring the intensity of the scattered light. In this example, a photomultiplier is used. Since scattered light is relatively weak, a slit 22 is provided between the magnetic-labeled body-specimen complex and the light receiving element 24 to restrict the range of measurement, and also a condenser lens 20 is provided to improve the sensitivity of light reception and the accuracy of measurement.

On the other hand, the light receiving element shown in FIG. 19 is one for measuring scattering on the light axis of the laser beam which passed through the magnetic-labeled body-specimen complex, and in this example, photo diode is suitable. Further, it is preferred to provide an ND filter between the laser beam 13 and the specimen in order to control the amount of the laser beam radiated to the magnetic-labeled body-specimen complex.

It is necessary to select the angle of radiation of the laser beam so that influence of reflection of the laser beam on the water surface of the well C can be avoided as far as possible. As a typical example of such value, it is designed so that the radiated laser beam 13 is incoming at an angle of 60° with respect to the water surface in the well A, and the light receiving element 24 which receives the scattered light 15 can measure the intensity of the scattered light radiated in the direction at an angle of 45° with respect to the water surface in the well A.

In this example, purified water such as deionized water or distilled water was used. However, the present invention is not limited to use of purified water but any ordinary liquid may be used. In contrast to the conventional EIA method in which the pH and the like of the liquid to be used must be selected carefully so as not to deteriorate the activity of enzymes, the present invention is free of such consideration on the liquid to be used after antiben-antibody reaction. Rather, organic solvents which have been unable to be used in the conventional methods and non-volatile ones, for example, paraffin oil and the like are preferred to prevent evaporation of the liquid.

EXAMPLE 11

FIGS. 20 (a) to (e) sequentially illustrate the operations of preparing test specimen in another laser magnetic immunoassay according to the present invention. The operations described herein are to immobilize a known antibody on the surface of non-magnetic particles and subject the product to an antigen-antibody reaction with unknwon antigen labeled with micro-particles of a magnetic substance, and thereafter separate the resulting complex.

The specimen container 11 used in this method is the same as that shown in FIGS. 18 (a) and (a)'. That is, the specimen container 11 is a container whose storage portion is partitioned by two partition walls a and b each having the height l smaller than the height L of the side walls into three wells, i.e., wells A, B and C.

In the well A of the specimen container 11 as described above, a liquid having dispersed therein known antibody 52 immobilized on non-magnetic particles 51 was filled in to a height smaller l than as shown in FIG. 20 (a). Polystyrene latex having an average grain size of 3 $\mu$m was used as the non-magnetic particle.

Subsequently, as shown in FIG. 20 (b), specimen collected from body fluid of a patient was injected into the well A with a micro-syringe 8a. The injected unknown virus antigen 52 was attached to micro-particles of a magnetic substance beforehand, and therefore, it underwent antigen-antibody reaction with the above-described knwon antibody 53, in the well A, to form a complex of "non-magnetic particle-antigen-antibody-micro-particles of magnetic substance" (51-52-53-55).

Thus, in this state, the following substances coexisted in the well A.

(1) Complex of "non-magnetic particle 51-antigen 52-antibody-53-micro-particles of magnetic substance 55".

(2) Unused "non-magnetic particle 51-antibody 53".

(3) Inevitably contained impurity particles.

As shown in FIG. 20 (c), purified water was poured into wells B and C with a divider 9 to elevate the level of water in the specimen container 11 higher than l.

In this state, as shown in FIG. 20 (d), when a magnet 5L with weak magnetic force was moved to closer to above the well A, the above-described (2) alone was attracted by the magnet 5L. Then, (2) in the well A was guided to the well B by moving the magnet 5L horizontally toward the well B. At this moment, (1) was not attracted by the magnetic force of the magnet 5L since its mass increased due to the non-magnetic particle 51 attached threreto. Therefore, (1), (3) and (4) remained in the well A.

Subsequently, as shown in FIG. 20 (e), a magnet 5H having a sufficiently strong magnetic force was moved closer to the well A. This time, since the magnetic force of the magnet 5H was sufficiently strong, (1) was attracted by the magnet. Therefore, movement of the magnet 5H toward the well C results in that only (1) was guided into the well C.

In this manner, purified water having dispersed therein only complex of "non-magnetic particle 51-antigen 52-antibody 53-micro-particles of magnetic substance 55" formed as a result of an antigen-antibody reaction was obtained in the well C of the specimen container 11. It is also preferred to use a porous filter in combination with guiding by means of magnetic force as shown in FIG. 18 (f) in the step (d) in order to assure separation furthermore. As described later hereinbelow, the prepared specimen as is in the specimen container 11 can be subjected to measurement by laser beam scattering.

Laser beam scattering measurement can be performed in the same manner as explained in FIG. 19 using the magnetic-labeled body-specimen complex shown in FIG. 20 (e).

EXAMPLE 12

Figure 21A:
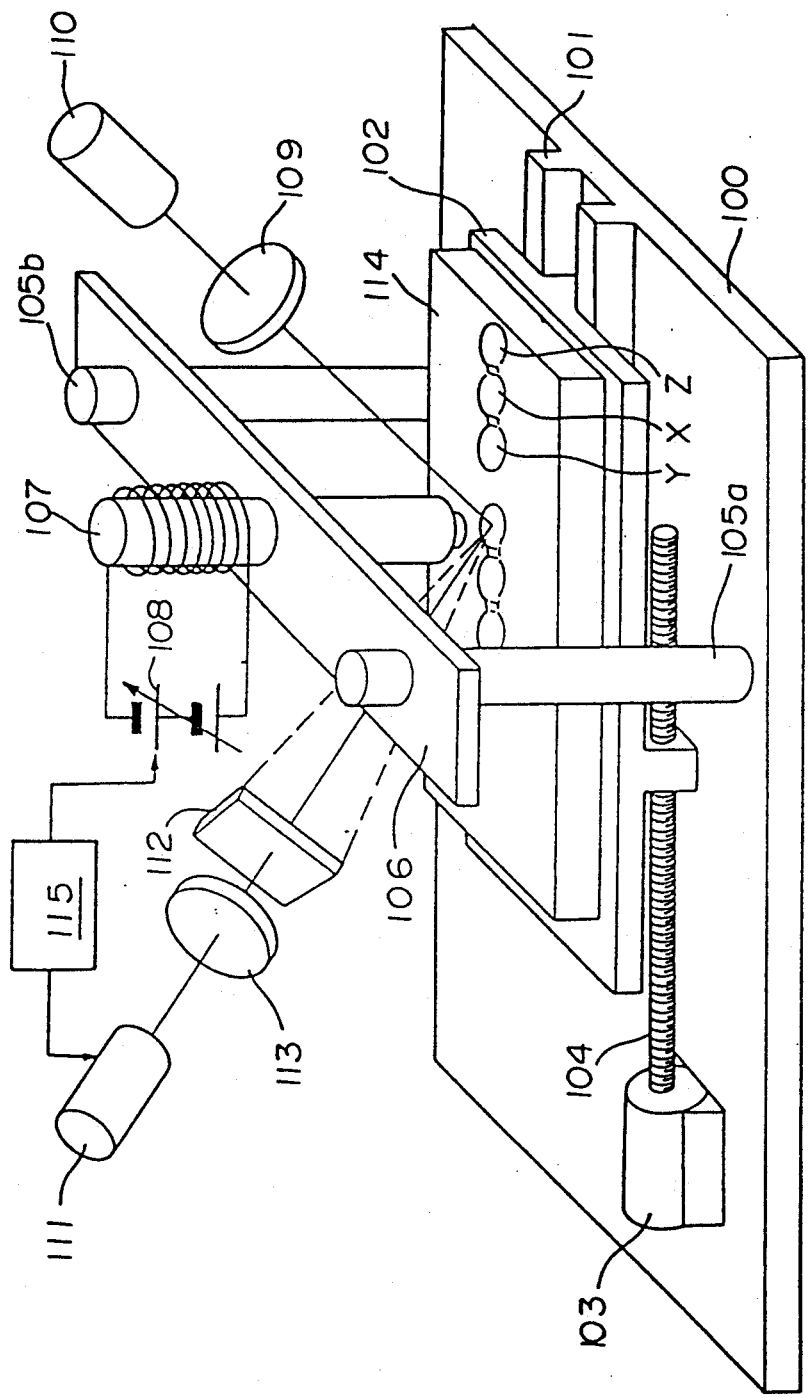
FIG. 21 (a) illustrates an apparatus which can carry out the operations shown in FIGS. 18(a) to 18(h), FIGS. 20(a) to 20(e) and FIG. 19 in the lump.

FIG. 21 (a) illustrates a laser magnetic immunoassay apparatus which can perform the operations as described in Examples 10 and 11 without interruption.

On a frame 100 constructed integrally with a guide member 101 is mounted a table 102, which is movable with a screw 104 driven by a motor 103. The table 102 is provided thereon a pair of poles 105a and 105b as well as a upport member 106, which together support an electromagnet 107. The electromagnet 107 is driven by a power source 108 whose output is variable so that it can generate desired magnetic force.

Further, although a support means is not shown, this apparatus is provided with an exchangeable ND filter 109, and also an He-Cd laser tube 110 for radiating a laser beam to a specimen immediately below the above-described electromagnet 107 as well as a light receiving element 11 for detecting the laser beam scattered by the specimen mounted on the table 102, the light receiving element 11 being described later herein. A slit plate 112 and a condenser lens 113 are arranged between the light receiving element and the specimen.

The specimen container 114 mounted on the table 102 comprises a set of wells X, Y and Z each of which is partitioned by a low partition wall p and q as shown in FIGS. 21 (b-1) and (b-2). Each well X, Y or Z of the specimen container in this example corresponds to each well A, B or C of the speciment container 1 shown in FIG. 18 (a); care being taken that the operations shown in FIG. 18 can be performed in the same procedures. In addition, the specimen container is provide with 3 sets of wells on a plate-like member. The wells X, Y and Z are arranged in the direction along the longitudinal axis of the memberand other sets of wells are arranged on the extension of the direction in which the wells are arranged in alignment.

Subsequently, the operation of the laser magnetic immunoassay shown in FIG. 21 (a) will be explained below.

Firstly, in the specimen container 114, the operations shown in FIGS. 18 (b) to (e) are performed to fill it with pure water having dispersed therein a specimen.

Without further treatment, the specimen container 114 is mounted on the table 102 so as to be fixed thereon. In this case, the container 114 is fixed in such a manner that the direction of arrangement of the well and each specimen container coincides with the direction of the movement of the table 102. Further, the table 102 is moved by driving the motor 103 so that one of wells, e.g., X can be positioned directly below the electromagnet 107.

Subsequently, the electromagnet 107 is weakly excited by the power source 108, and the table 102 is moved toward the right hand side on the drawing under the conditions where unused magnetic-labeled body having a small mass is guided to near the water surface in the well X. This means that the electromagnet 107 is moved relatively with respect to the specimen container 114 toward the well Y, and thus unsused magnetic-labeled body is guided to the water surface. Therefore, unsused magnetic-labeled body is removed. This operation corresponds to the operation shown in FIG. 18 (f).

Next, the power supply is cut off to return the movable table to the original position, and then the electromagnet 107 is excited strongly. As the result, the magnetic-labeled antigen-antibody complex is guided to near the water surface of the well X, and the magnetic-labeled antigen-antibody complex is guided to the water surface of the well Z with the movement of the table 102 toward the left hand side on the drawing. That is, this operation corresponds to that shown in FIG. 18 (g).

Finally, while keeping these conditions, i.e., maintaining the state in which the magnetic-labeled antigen-antibody complex guided to the water surface within the well Z is concentrated, detection and measurement of the specimen by the scattering of the laser beam. In this manner, measurement on one set of the wells is completed.

Further, as shown in FIGS. 21 (b-1) and (b-2), the specimen container 114 is provided with three sets of wells and if similar operations are repeated on other wells a plurality of specimens can be measured continuously. The sensitivity of detection achieved by the above operations was about 5 picograms.

Figures 22A, 22B:
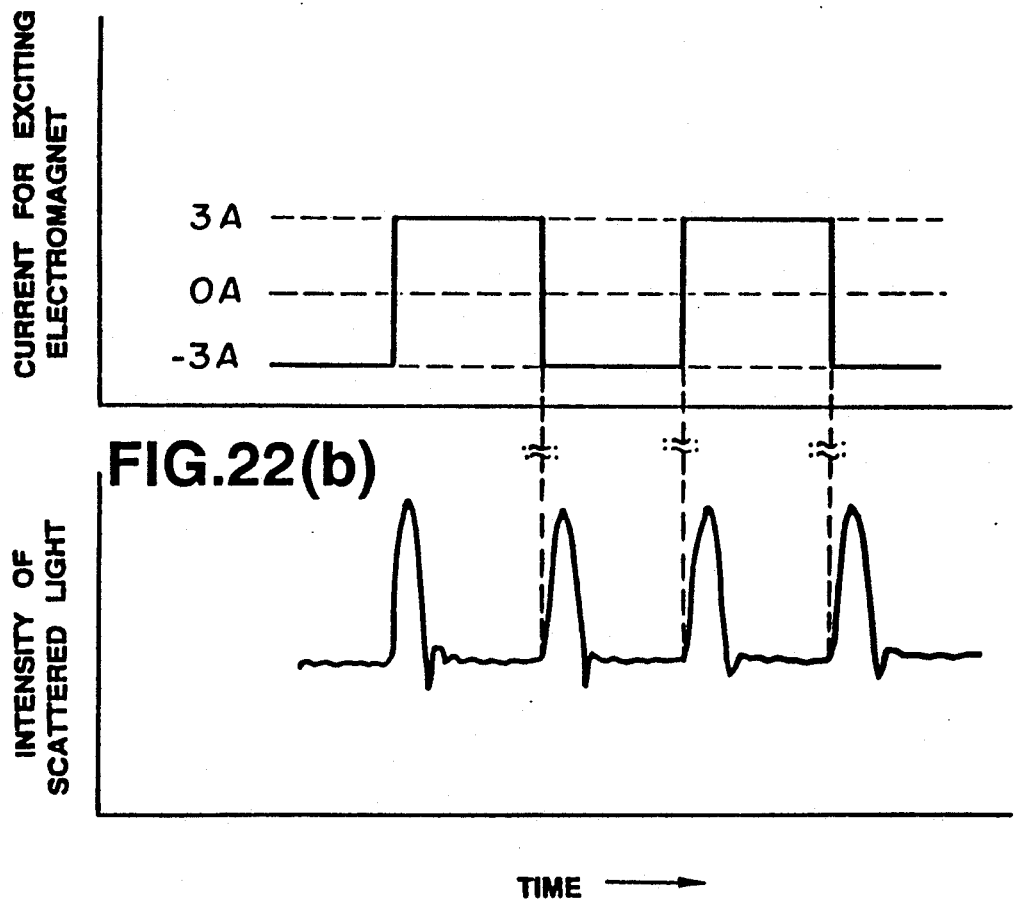
FIG. 22 (a) is a graph showing a modified waveform of a power source in the apparatus shown in FIG. 21(a)

Subsequently, measurement by laser beam scattering was performed in different manners. More particularly, upon measurement by laser beam scattering, the electromanet 107 for guiding and concentrating the magnetic-labeled antigen-antibody complex was driven by a power supply modulated with a rectangular wave having an amplitude from +3A to −3A and a predetermine frequency as shown in FIG. 22 (a). Detection of scattered beams by the receiving element 111 was performed using a lock-in amplifier 115 synchronized with the modulation of the power supply.

Assuming the magnetic field generated by the electromagnet 107 is alternating magnetic field, the magnetic substance trapped by the magnetic field rotates in synchronization with the variation in the polarity of the magnetic field. Therefore, detection of variation in scattered beams synchronized with the power supply current reults in that influences of background due to unavoidable impurity particles dispersed in the specimen can be eliminated.

FIG. 22 (b) is a graph showing the results of measurement on the variation in the laser beam scattering performed with the above-described operations. For information, FIG. 22 (b) uses the same scale as that used in FIG. 22 (a) with respect to horizontal axis.

Mesurements while performing the above operations achieved a detection sensitivity of not higher than 2 picograms, which is by three times as high as that of the static measurement.

EXAMPLE 13

Figure 23A:
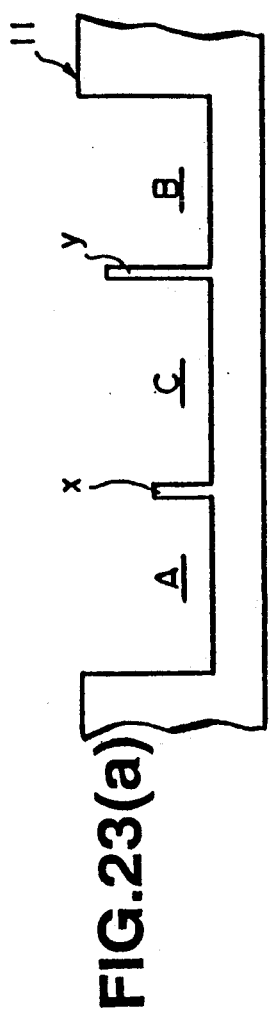
FIG. 23 (a) illustrates the construction of a specimen container which can be used advantageously in a laser magnetic immunoassay apparatus according to another embodiment of the present invention.
Figure 23B:
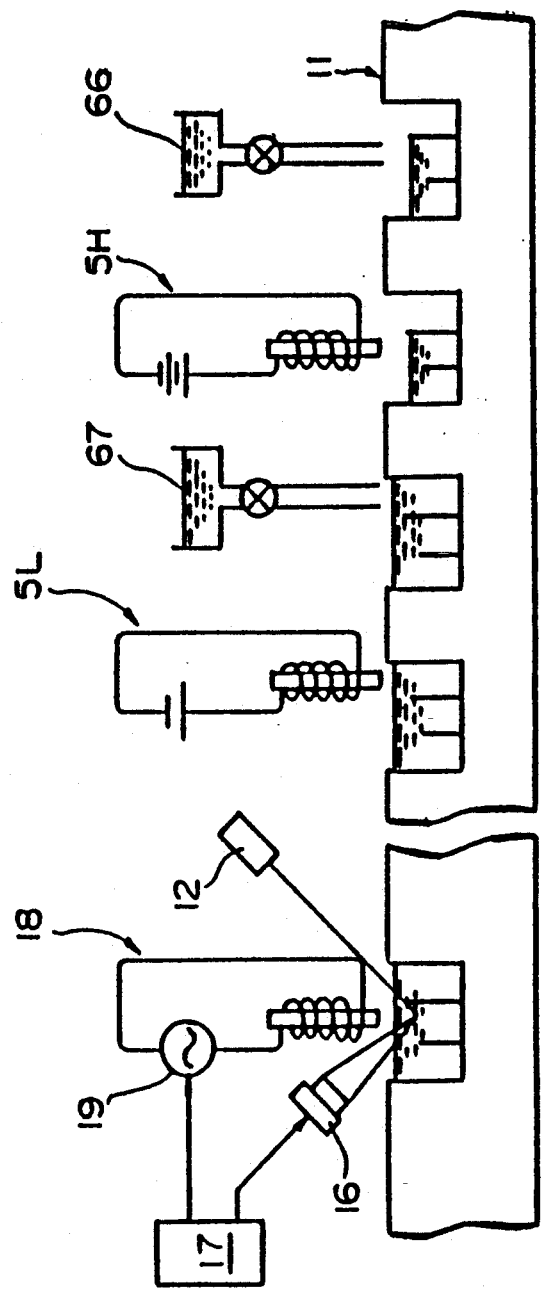

FIGS. 23 (a) and (b) schematically illustrate the construction of an apparatus which perform the method of the present invention continuously.

Although the specimen container used in the instant apparatus is similar to that shown in FIGS. 18 (a) and (a') in that it comprises a well A for performing an antigen-antibody reaction therein, a well B for storing unused antigen or antibody separated from the well A, and a well C for storing an antigen-antibody complex containing a specimen to be detected, it differs from the apparatus previously described in the order of arrangement of each well. That is, the wells are arranged in the order of A-C-B as shown in FIG. 23 (a). Further, partition walls X and Y for partitioning each well are so designed that the partition wall X which partitions the wells A and C is lower than the partition wall which partitions the wells C and B, which is also shown in FIG. 23 (a).

FIG. 23 (b) schematically illustrates the construction of an apparatus which can treat specimens stored in such container continuously.

The apparatus is designed so that it can move a plurality of specimen containers arranged and connected to each other in the direction of the arrangement of the wells as shown in FIG. 23 (b) from right to left on the drawing at a predetermined speed. Above the specimen container 11 are arranged a water injection means 66 for supplying water to the specimen container, a magnet 5H with strong magnet force, another water injection means 67 for supplying water to the specimen container, a magnet 5L with weak magnet force, and a measurement means 68 for measuring specimens by laser beam scattering in this order.

The operation of preparation of test sepcimen liquid using the above container is performed as follows. Firstly, as shown in FIG. 23 (c-o), an antibody 62 attached to a non-magnetic particle 61 was subjected to an antigen-antibody reaction in pure water filled in the specimen container, and further the product was subjected to an antigen-antibody reaction with anti-immunoglobulin 64 to which micro-particles of a magnetic substance was attched.

Therefore, the well contained therein in a floating state:

(1) Antigen-antibody complex (61-62-63-64-65).

(2) Anti-immunoglobulin to which micro-particles of magnetic substance was attached (64-65).

(3) Antibody to which non-magnetic particle was attached (61-62).

Subsequently, as shown in FIGS. 23 (c-1), the specimen container 11 was filled with pure water to the height of the partition wall X from the side of the well X using a water injection means 66.

Next, as shown in FIG. 23 (c-2), the specimen container 11 was passed below the electromagnet H which generated strong magnetic force. Then, those attched to micro-particles of magnetic substance, i.e., (1) and (2) above, were guided by the magnet 5H to the well C. With further movement of the specimen container, (1) and (2) collided the partition wall Y and therefore all of them remained in the well C.

Subsequently, as shown in FIG. 23 (c-3), the specimen container reached below the water injection means 67, and pure water was injected thereto from the side of the well B. As the result, all the wells were communicated with each other near the water surface.

The specimen container 11 was further moved to below the magnet 5L as shown in FIG. 23 (c-4). The magnet 5L generated magnetic force which could guide (2), which was light, but could not guide (1), which was heavy, so that only (2) could be guided to the well B with this operation.

Thus, only the antigen-antibody complex (61-62-63-64-65) containing the specimen was stored in the well C. Therefore, as shown in FIG. 23 (c-5), the antigen-antibody complex (61-62-63-64-65) in the well C could be measured by means of the measurement means 68 arranged further downstream of the apparatus. The sensitivity of measurement could further be enhanced by providing the apparatus with an electromagnet 18 driven by alternating current 19 in addition to a laser beam radiation means 12 and a light receiving element 16 and detecting laser beam scattering.

What is remarkable in a series of operations described-above is that the direction of relative movement between the magnets 5H and 5L and the specimen container 11 in each operation is always constant. Therefore, preparation and measurement of the test specimen liquid can be performed continuously and efficiently if the specimen container 11 is moved always at a constant speed and each equipment is operated along a predetermined schedule.

EXAMPLE 14

Figure 24A:
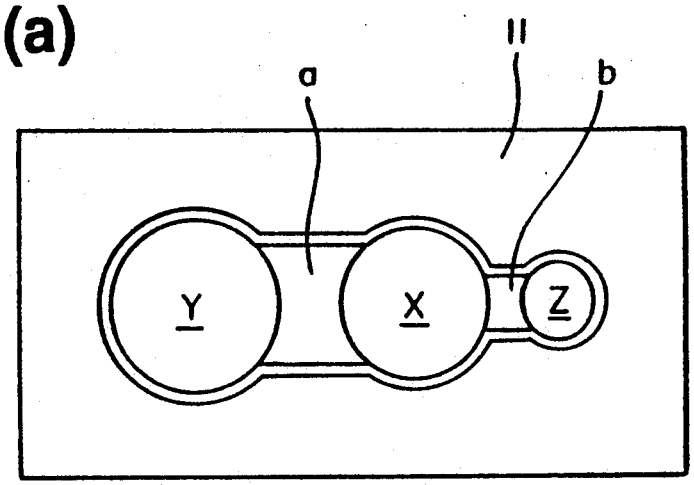
FIGS. 24(a) and 24(b) illustrate the construction of a container for storing a specimen for use in the laser magnetic immunoassay according to the present invention.
Figure 24B:
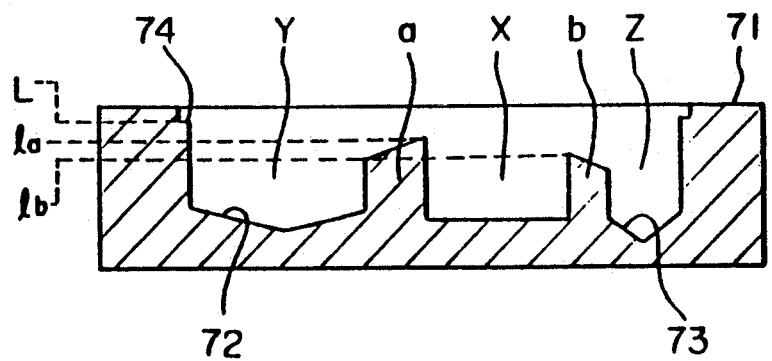

FIGS. 24 (a) and (b) illustrate the shape of the specimen container. FIG. 24 (a) is a top plan view and FIG. 24 (b) is a side cross-sectional view.

The specimen container of the present invention is constructed such that three wells X, Y and Z are arranged on a support 71 in a straight line, with the well X being positioned in the center. The wells X and Y are separeated from each other with a partition wall a, and the wells Y and Z are separated one from another with a partition wall b. As shown in FIG. 24 (b), the partition wall a has a height of $l_a$ and is lower than the common side walls. On the other hand, the partition wall b has a height of $l_b$ which is smaller than $l_a$. A step 74 is provided at a height of L which is smaller than the height of the common side walls but is larger than $a$ as a guide for water injection.

The support 71 for the well is made of a polystyrene. The size of each well is set up as follows.

|        | Diameter | Volume |
|--------|----------|--------|
| Well X | 10 mm    | 0.6 ml |
| Well Y | 5 mm     | 0.2 ml |
| Well Z | 10 mm    | 0.6 ml |

The container is so dimensioned that the upper end of the partition wall a is by 1 mm lower than the guide 74 for water injection and the upper end of the partition wall b is by 1 mm lower than that of the partition wall a.

The term "volume" of each well as used herein refers to the volume of a liquid that can be taken out from each well independently of the other wells after the specimen container is filled with the liquid up to the level of the guide for water injection. Therefore, the volume of X is the volume of a portion not higher than the height $l_b$; the volume of Y is a sum of the volume of a portion from the guide for water injection to the height $l_a$ which is common to all the wells and the volume of a portion not higher than the height $l_a$; the volume of the well Z is a sum of the volume of a storage portion common to the wells X and Z and not higher than $l_a$ and the volume of a storage portion not higher than $l_b$ and is specific to the well Z.

Further, in the operation of preparing a test specimen solution described later herein, the contents of the well is transferred to the well Y or Z, and therefore, it is desired to provide the partition walls a and b on the respective top surface thereof with a slope inclined down toward the wells Y and Z, respectively. Also, each of the wells Y and Z is provided on its bottom surface 72 or 73 with a slope downward to the center thereof in order to facilitate the operation of withdrawing the contents of the wells Y and Z.

When the specimen container 11 constructed as described above is filled with a liquid from one of the wells up to the guide for water injection 74, the storage portions come to be communicated at the tops of the partition walls a and b, and thus the liquid prevails in all the wells.

On the other hand, when the liquid in, for example, the well Y is drained the whole contents of the well Y are extracted while the contents of the respective wells X and Z remain as is and communication between the wells X and Z is maintained near the water surface. When the contents of the well Z are extracted, the contents of the well X remain substantially as is. Further, when the liquid is collected from the wells the liquid of a predetermined volume corresponding to the volume of the well is obtained.

FIGS. 25 (a) to (i) illustrate sequentially the method of preparing test sepcimen liquid using the specimen container shown in FIG. 24. The following operations are to quantitatively determine an antibody extracted from a patient. Labeling was performed by attaching an antibody having attached thereto micro-particles of a magnetic substance to a specimen.

Firstly, as shown in FIG. 25 (a), a known antigen immobilized to a support 81 was fixed to the bottom of the well X. The support 81 used is a film of a Novolak resin prepared according to Example 21 hereinbelow. That is, a 20% ethanol solution of Novolak resin was coated and dried on the bottom of the well X and the surface thereof was contacted with a PBS solution containing a known virus antigen 80, for example, inactivated influenza virus, for one night to immobilize the virus onto the Novolak resin film.

Subsequently, as shown in FIG. 25 (b), a liquid having dispersed therein an antibody 82 collected from the neurolymph of a patient was injected into the well X with a micro-syringe 8a, and as the result the antibody 82 and the antigen 80 underwent an antigen-antibody reaction to form an antigen-antibody complex.

Further, as shown in FIG. 25 (c), a liquid having dispersed therein an anti-immunoglobulin 83 to which micro-particles of a magnetic substance were attached was injected into the well X with a micro-syringe 8b. The anti-immunoglobulin 83 underwent an antigen-antibody reaction with the antigen-antibody complex 80-82 by the operation shown in FIG. 25 (b), thus forming a magnetic-labeled antigen-antibody complex 80-82-83-84 which was labeled with microp-particles of the magnetic substance. The remaining anti-immunoglobulin which did not contribute to the reaction were floating in the well X as is.

All the operations were performed in the well X. Therefore, upon injection of the liquid into the well X, care must be taken so that the height of the contents should not exceed the height b.

Subsequently, as shown in FIG. 25 (d), pure water was injected up to the guide for water injection from the side of the well X with a micro-syringe 8c. Pure water injected into the well Z before long overflew over the partition walls b and a, and the wells X, Y and Z were all filled with pure water and at the same time the part of the anti-immunoglobulin 83 which did not contribute to the reaction and was floating in the well X was washed out toward the well Y.

Next, as shown in FIG. 25 (e), a magnet 5 was moved to near the water surface of the well Z and then toward the well Y along the surface of pure water. With this operation, unused anti-immunoglobulin 83 to which micro-particles of a magnetic substance are attached were wholly guided to the well Y.

As shown FIG. 25 (f), excessive antibody with micro-particles of the magnetic substance could be removed by sucking up the liquid in the well Y with a micro-syringe 8d. In the operation shown in FIG. 25 (c), if the amount of the anti-immunoglobulin 83 to be injected is quantitatively determined beforehand, the amount of the anti-immunoglobulin 83 which contributed to the antigen-antibody reaction can be obtained by quantitatively determining the excessive anti-immunoglobulin 83 removed during the operation.

Subsequently, as shown in FIG. 25 (g), an alcohol such as methanol or ethanol was added to the well X with a micro-syringe 8e or pipette to dissolve the Novolak resin film to fluidize the specimen. The addition of alcohol was performed preferably by firstly removing most of the liquid in the well with a micro-syringe, adding an alcohol and then adding water. In the drawing, decomposed support is schematically indicated by a symbol (Δ) and reference numeral 81a. Actually, a part of the support 81 is dispersed as solid. Thus, the antigen-antibody complex 80-82-82-84 containing micro-particles of the magnetic substance 84 floated in the well X. In this case, although a heater 85 is described in the drawing, it was not used (unnecessary).

Next, as shown in FIG. 25 (h), the magnet 5 was moved near the water surface and dislocated along the water surface from the well X to the well Z. With this, the antigen-antibody complex 80-82-83-84 containing the micro-particles of the magnetic substance 84 was guided into the well Z. At this t±me, particles not containing the magnetic substance, i.e., fragments of the support 81 or impurities inevitably contained floating in the liquid remained in the well X.

Thus, pure water in the well Z contained dispersed therein only the antigen-antibody complex 80-82-83-84 containing the specimen. Therefore, as shown in FIG. 25(i), the desired specimen could be obtained by collecting the liquid only in the well Z with a micro-syringe 2f.

Although the above-described method involved immobilization of antigen by forming a Novolak resin film on the bottom of the specimen container, a silicon chip having immobilized thereto virus and prepared according to Example 21 can be placed on the bottom of the well X as is followed by similar operations.

For comparison, immobilization to the conventional gelatin support was also performed.

In this case, as shown in FIG. 25 (a), 20 μl of a 5 wt. % aqueous gelatin solution heated at 60° C. was injected into the well X to form a gell on the bottom of the well X, and thus immobilizing the known virus antigen 80 on the surface thereof.

Subsequently, the operations shown in FIGS. 25 (b) to (f) were the same as those shown above, but when a gelatin support was used, in the step shown in FIG. 25 (g), the well X was heated from below at 60° C. for about 2 minutes with a heater 85 to dissolve the support 81 having fixed thereto the antigen 80 so as to fluidize the specimen. In this case, the micro-syringe 8e was not used. In the drawing, the decomposed support was schematically indicated by a symbol (Δ) with a reference numeral 81a. Actually, a part of the support 81 is dispersed as solid. Thus, the antigen-antibody complex 80-82-82-84 containing micro-particles of the magnetic substance 84 floated in the well X.

Subsequent operations were the same as in the case of the alcohol dissolution described above.

Although the method of immobilization can be used in the present invention, the method of immobilization according to this example can achieve fluidization almost immediately by mere addition of alcohol and water but requires heating at 60° C. or more, and therefore is very easy and advantageous.

EXAMPLE 15

Figure 26A:
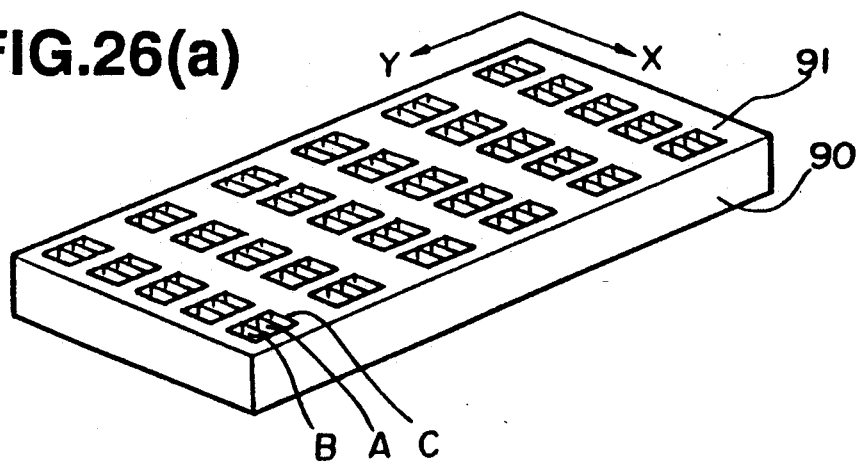
FIGS. 26 (a) and 26(b) illustrate another embodiment of the specimen container according to the present invention, with FIG. 26 (a) being whole view and FIG. 26 (b) a view illustrating one unit included in the apparatus.
Figure 26B:
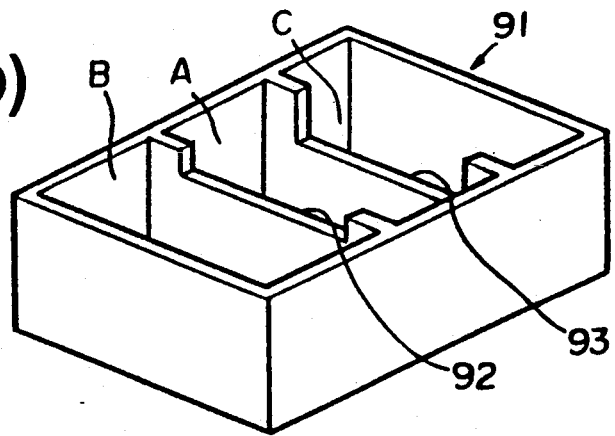

FIG. 26 (a) illustrates the construction of other example of the specimen container according to the present invention.

As shown in FIG. 26 (a), in this example, a plurality of specimens 91 having substantially the same construction as that shown in Example 14 are arranged on a support 90 for wells. Each specimen container 91 comprises a set of wells A, B and C partitioned with partition walls 92 and 93 of different heights as shown in FIG. 26 (b). In the specimen container, the partition wall 92 is formed as being lower than the partition wall 93, and each of the wells A, B and C corresponds to each of the wells X, Y and Z shown in FIG. 24. Therefore, the operational procedures upon use is the same as that shown in Example 14 (FIG. 25). It is preferred to use a Novolak resin film in immobilization.

The arrangement of specimen containers is such that they are arranged in a straight line along the direction of arrangement of the wells in a single specimen container (as shown in FIG. 26(a), the direction being indicated hereinafter as "direction Y"), and also a plurality of specimen containers are arranged in alignment in the direction perpendicular to the above-described direction (as shown in FIG. 26 (a), the direction being indicated hereinafter as "direction X"). Further, all the specimen containers arranged on the support 90 for wells are of uniform order of arrangement of wells.

Figure 27:
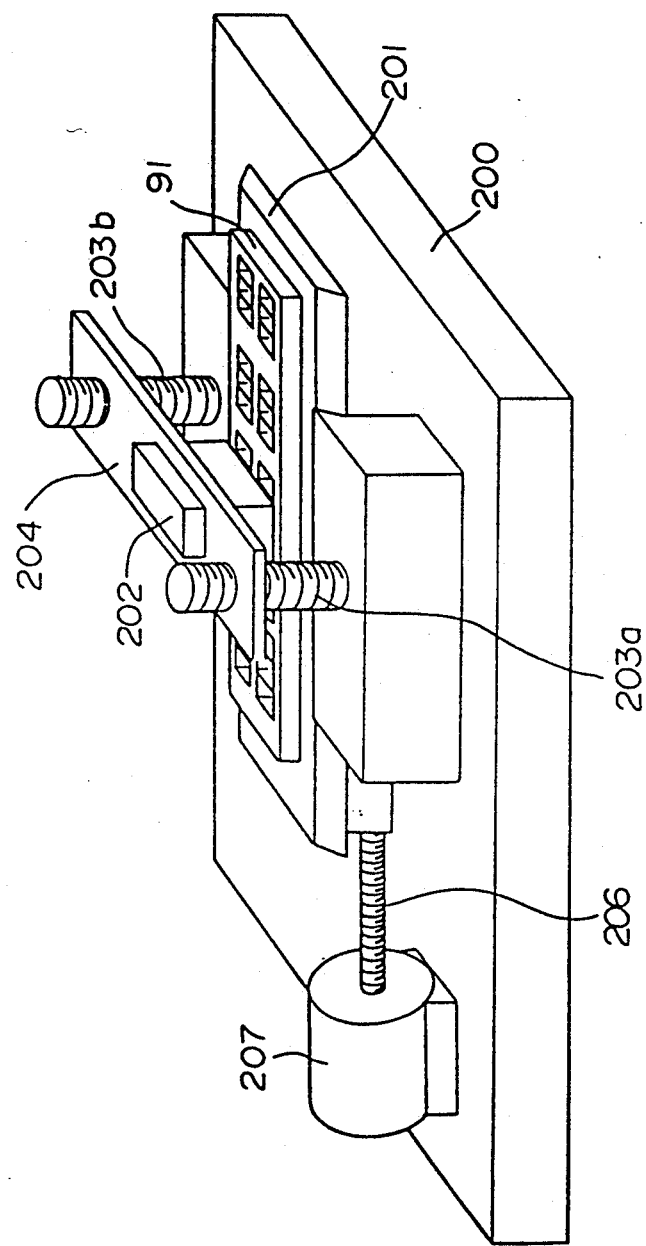
FIG. 27 illustrates the action of an instrument for utilizing the specimen container shown in FIG. 26 (a) advantageously.

As described above, the integral specimen container comprising a plurality of specimen containers is very advantageous in treating many specimens in the lump as described hereinbelow. FIG. 27 illustrates the construction of an instrument for preparing specimens for use in the application of the above-described specimen container.

That is, as shown in FIG. 27, this apparatus comprises a frame 200, a rectangular table 201 provided on the frame 200 and movable in the longitudinal direction, and a permanent magnet 202 supported on the table 201 by two poles 203a and 203b as well as a support member 204 so that the movement of the table 201 should not be obstructed. The table 201 is driven by a motor 207 through a sreaded bar 206 penetrating the base portion the table 201. The poles 203a and 203b are also threaded. By rotating the poles, the permanent magnet 202 can be moved up and down so that magnetic force onto an object mounted on the table 201 can be controlled. Although details will be described hereinbelow, the magnet 202 has a width substantially the same as total width of the table 201. Then, the operation of the instrument shown in FIG. 27 will be explained.

Firstly, the operations shown in FIGS. 25 (a) to (d) were performed in each central well in the specimen container shown in FIG. 26 (a). Then, as shown in FIG. 27, the specimen container was mounted on the table 201 in such a manner that the direction Y coincided with the direction in which the table moved and that the magnet 202 was positioned above the well C of one of the specimen containers arranged in a row in the direction X. Subsequently, the motor 207 was driven to move the table 201 so that the magnet 202 could move relatively from the well C to the well B. That is, the operation shown in FIG. 25 (e) was performed here. Further, after removing the contents from each well B in the row concerned the contents of each well B were fluidized. Tehreafter, the table 201 was moved in the opposite direction with respect to the above-described direction, and the operation shown in FIG. 24 (h) was performed to guide the specimen to the well C. Thus, only the antigen-antibody complex containing the specimen and micro-particles of a magnetic substance were stored in each well C of a plurality of specimen containers arranged in the direction X.

Although an antigen or antibody was immobilized to wells for use in antigen-antibody reactions with a Novolak resin, the present invention is not limited to such example. For example, it can be used in a method in which an antigen or antibody is immobilized on the surface of particles of a non-magnetic substance such as polystyrene latex, the resulting particles is subjectd to an antigen-antibody reaction in the state of floating in the well for antigen-antibody reaction according to the present invention, and unused labeled body is discriminated by difference in mass between the antigen-antibody complex containing non-magnetic particles and the antigen or antibody which does not contain such.

As described in detail above, specimen labeled with micro-particles of the magnetic substance with containing very little contamination can be extracted using the specimen container and method of preparing specimens according to the present invention.

EXAMPLE 16

Figure 28:
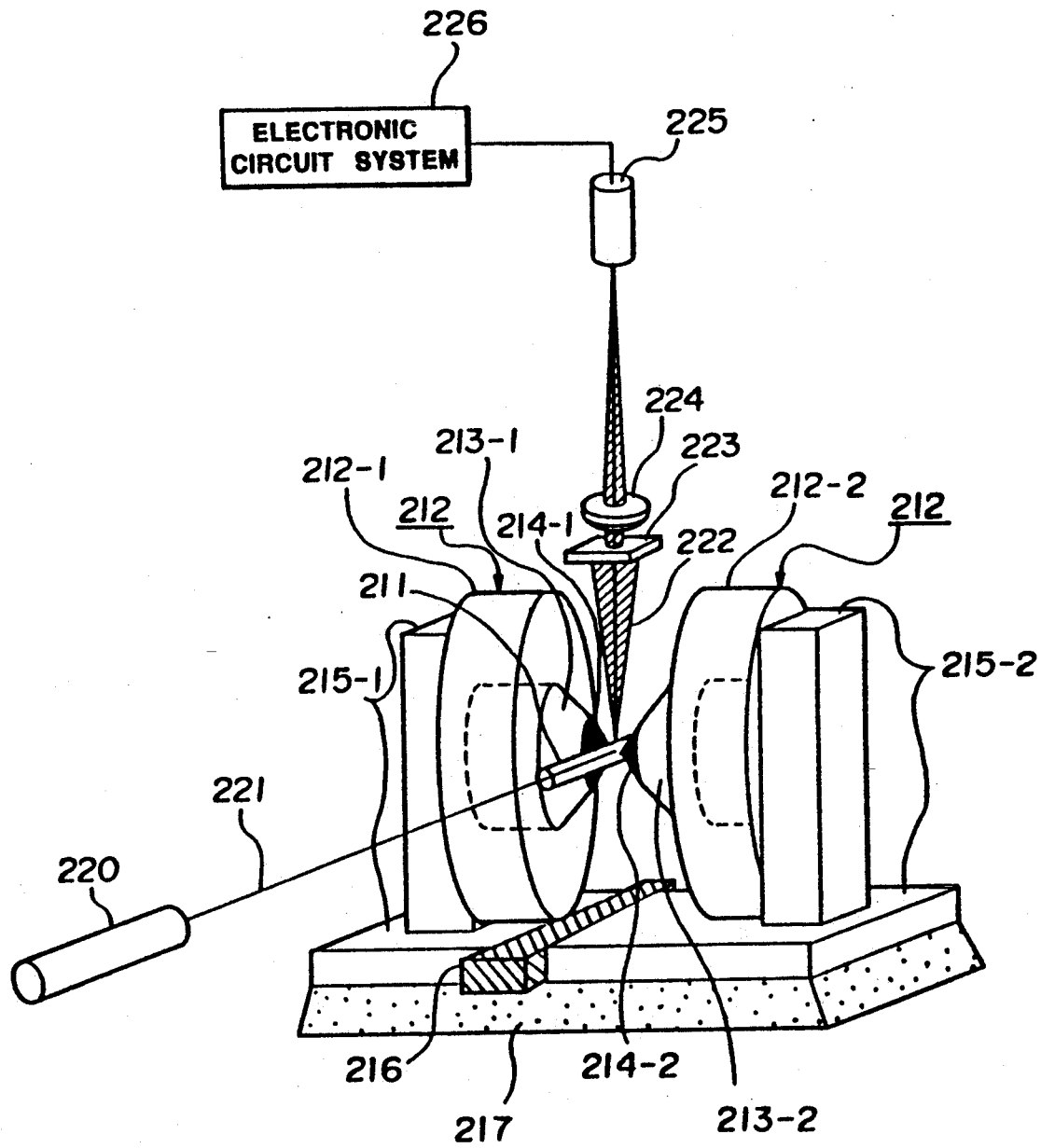
FIG. 28 is a schematical view illustrating the construction of the laser magnetic immunoassay apparatus according to the present invention.

FIG. 28 is a schematical view of a laser magnetic immunoassay apparatus illustrating an example of the present invention, in which 211 is a specimen container, 212 is an electromagnet, 212-1 and 212-2 are electromagnet coils, 213-1 and 213-2 are cores of the electromagnets, 214-1 and 214-2 are magnetic pole pieces of the electromagnet, 215-1 and 215-2 are yokes of the electromagnet, 216 is a magnetic flux controlling piece, 217 is a stand, 220 is a laser beam source (laser beam radiating optical system), 221 is a radiated laser beam, 222 is a scattered laser beam flux, 223 is a slit, 224 is a condensing lens for condensing the scattered laser beam, 225 is a photomultiplier for receiving the scattered laser beam, and 226 is an electronic circuit system for processing output from the photomultiplier. The specimen container 211 is a small tube having an inner diameter of 2.5 mm, which is fitted in the center of the pair of electromagnets horizontally. The laser beam source 220 is arranged so that the laser beam 221 passes through the small tube at the central portion in parallel to the axis of the small tube. The slit 223, the lens 224 and the photomultiplier 225 (these members constituting a light receiving system for receiving the scattered laser beam flux) are arranged so that the scattered light from the magnetic-labeled body in the specimen container 221 in the central portion of the pairs of the electromagnets can be received from just below. The pairs of the electromagnets comprise coils, cores made of pure iron, magnetic pole pieces and yokes. The coils 212-1 and 212-2 are wound in the same direction each 5,000 turns. The yokes 215-1 and 215-2 are mounted on the stand 217 made of a non-magnetic substance and can be slided on the stand 217 in order to control the magnetic gap distance between the pair of the electromagnets. The magnetic flux control piece 216 is of a wedge shape and is detacheably fitted between the yokes 215-1 and 215-2. The magnetic flux generated by the electromagnet 212 is controlled by the magnetic flux control piece 216, and when the magnetic flux control piece 216 is inserted between the yokes 215-1 and 215-2, the magnetic flux in the magnetic gap portion in which the specimen has been inserted increases. On the other hand, when the magnetic control piece 216 is removed from between the yokes 215-1 and 215-2, the pair of the electromagnets function as two independent electromagnets. Since the magnetic flux control piece 216 is of a wedge shape, the magnetic flux density of the magnetic gap portion between the electro-magnets can be controlled freely within a predetermined range by inserting and withdrawing the magnetic flux control piece in and from between the yokes. The magnetic pole pieces 214-1 and 214-2 preferably are of a conical shape, and they are fastened to the core 213-1 and 213-2, respectively, with bolts.

Figure 29:
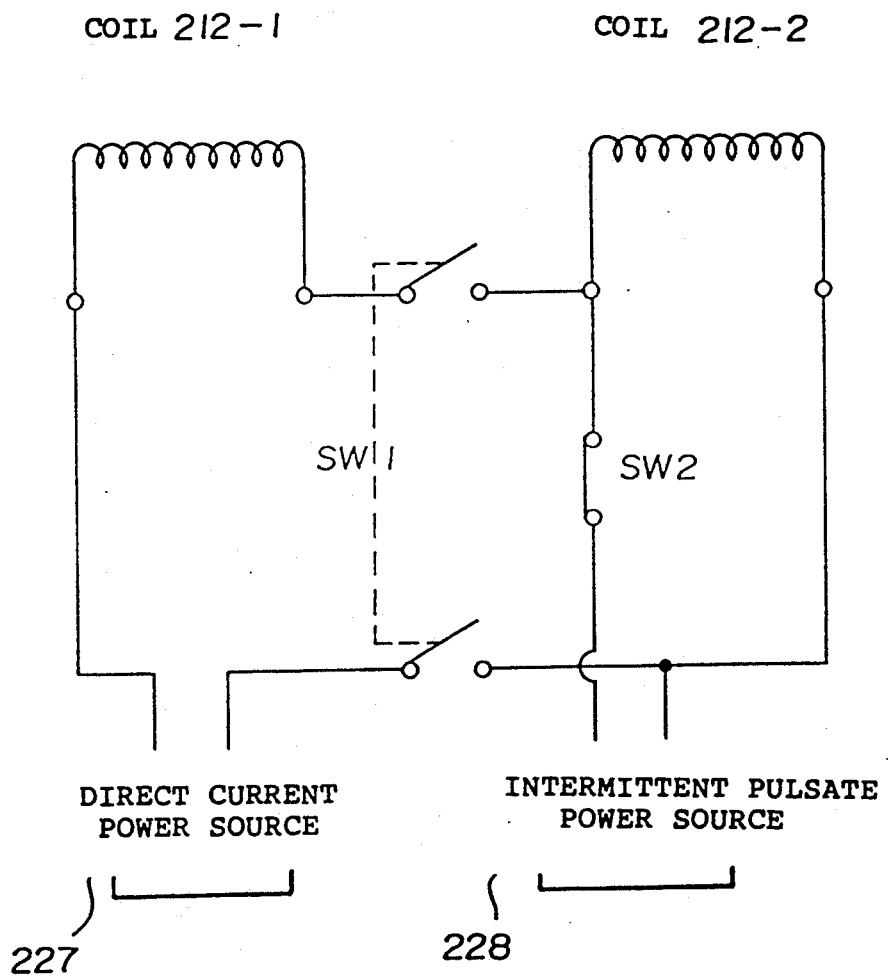
FIG. 29 is a diagram showing a circuitry for a power source for energizing a pair of electromagnets.

FIG. 29 illustrates a power source and a power supply circuit for exciting the pairs of the electromagnets. The power source is used for concentrating the magnetic-labeled body and driving it after the concentration. The electromagnet coils 212-1 and 212-2 can be connected or separated by means of a switch SW1, which at the same time is interlocked with a switch for a direct current power supply 227. On the other hand, the electromagnet coil 212-2 is connected to an intermittent pulse power source 228 through a switch SW2. The switch SW2 is in opposite on-off direction to switch SW1, and when the switch SW1 is closed, the switch SW2 is open.

Figure 30A:
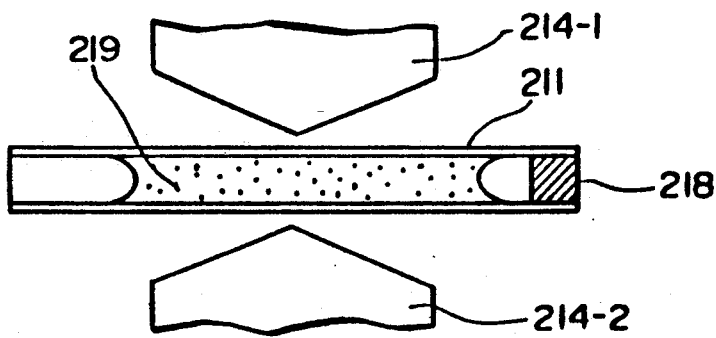
FIGS. 30 (a) and 30(b) and FIGS. 31 (a) and 31(b) are plan views illustrating a magnet piece and a specimen container when a pair of the electromagnets are viewed from above, with FIGS. 30(a) and 30(b) illustrating a step of concentrating a magnetic-labeled body and FIGS. 31 (a) and 31(b) a step of driving the magnetic-labeled body after concentration.
Figure 30B:
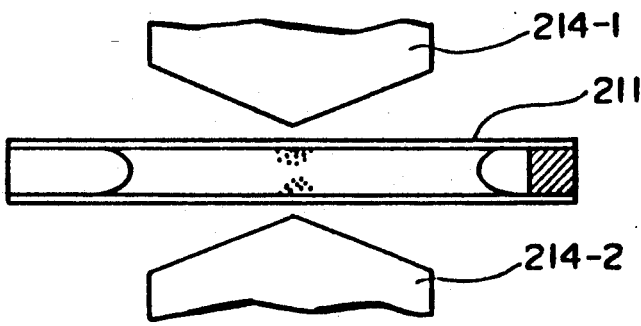
Figure 31A:
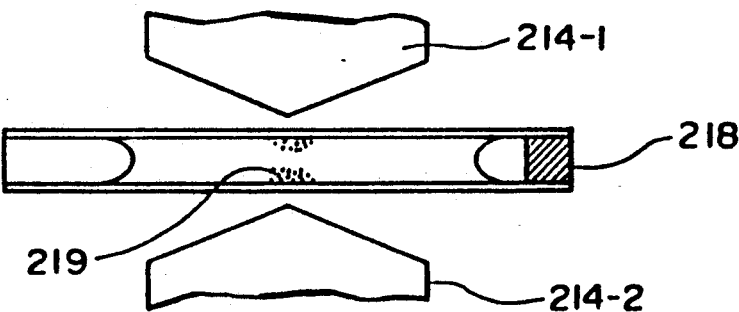
Figure 31B:
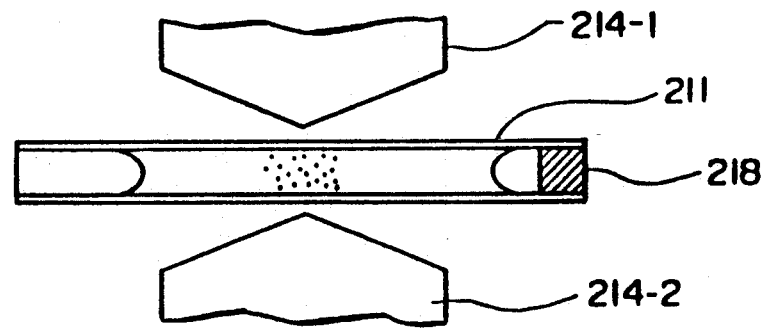

FIGS. 30 and 31 are plan views of the magnetic pole pieces 214-1 and 214-2 when the electromagnet pair is viewed from above in FIG. 28; 218 is vaselin for sealing the specimen and 219 is a magnetic-labeled body. FIG. 30 illustrates a step of concentrating the above-described magnetic-labeled body, and FIG. 31 illustrates a step of driving the magnetic-labeled body after the concentration.

Then, the step of concentrating the magnetic-labeled body will be described. Firstly, the switch SW1 in FIG. 29 is closed and the direct current power source 227 is connected to the coils 212-2 and 212-2. Upon this, the magnetic flux control piece 216 in FIG. 29 is inserted between the yokes 215-1 and 215-2. Since the magnetic pole piece is conical in shape, excitation of the electromagnet pair with direct current results in that the magnetic flux density of the magnetic gap portion at the central portion of the electromagnet pair is maximum. In this example, the magnetic gap length was 5 mm and application of current of 1A gave rise to a maximum of 12,000 G at the central portion of the electromagnet pair.

FIGS. 30 (a) and (b) schematically show distribution of magnetic-labeled body in the specimen container before concentration and after concentration, respectively. In FIG. 30 (a), before the excitation of the electromagnet pair, the magnet-labeled bodies distribute in the solution uniformly while after direct current excitation of the electromagnet pair the magnetic-labeled bodies are gathered on the inner wall of the sepcimen container corresponding to the apex of the magnetic pole piece as shown in FIG. 30 (b).

Then, the step of driving the magnetic-labeled bodies after concentration will be described. The switch SW1 in FIG. 29 is opened and the switch SW2 is closed, and intermittent pulse power supply 228 is connected to the electromagnet 212. Upon this, the magnetic flux control piece 216 in FIG. 28 is removed from between the yokes 215-1 and 215-2, and the electromagnet coils 212-1 and 212-2 are separated.

FIG. 31 (a) schematically illustrates the distribution of magnetic-labeled bodies during excitation of the electromagnet coil 212-1 with intermittent pulses of a pulse peak value of 0.2 A and a frequency of 0.2 Hz, and FIG. 31 (b) schematically illustrates the distribution of magnetic-labeled bodies during non-excitation of the electromagnet coils. That is, in FIG. 31 (a), the magnetic-labeled bodies distribute concentratedly on the surface of the inside wall of the specimen container corresponding to the apex of the magnetic pole piece while in FIG. 31 (b), the magnetic field at the central portion of the electromagnet pair is almost negligible since the core 213-1 and 213-2 as well as the magnetic pole piece have low residual magnetization, and therefore, the magnetic-labeled bodies are dispersed in the solution from the wall surface of the specimen container to the circumference as the result of Brownian movement, and as time elapses they distribute unformly inside the specimen container around the apex of the magnetic pole piece as a center. Therefore, the laser beam guided to the central portion of the small tube along the axis thereof is scattered by the specimen placed at the central portion of the electromagnet pair, with the intensity of the scattered light being varied in accordance with the period of the pulse power supply. The scattered light from the specimen can be taken out from above or below the specimen container.

The specimen container 211 is a small tube preferably having an aperture larger than the diameter of the diameter of the laser beam, and it is advantageous for further handling if the specimen after the antigen-antibody reaction is inspired into inside the small tube attached to a micro-syringe and then one of the openings is sealed with vaselin or a like. It is preferred that the small tube is fitted at the central portion of the electromagnet pair horizontally since it is disadvantageous that when the small tube is held vertically, the magnetic-labeled bodies concentrated at the central portion of hte magnetic pole piece will fall down from the central portion of the magnetic pole piece due to its gravity if the electromagnet coil is non-excited and thus the central portion of scatter-ing goes up and down whenever the pulse excitation occurs.

Preferred range of the period of the pulse excitation is from 0.05 Hz to 10 Hz since below 0.05 Hz, it takes a long time for measurement, and above 10 Hz, the magnetic-labeled bodies cannot follow the variation in the magnetic field. Further, it is preferred that the pulses have a peak value smaller than the direct current excitation current value and DC off-set is absent. If DC off-set is present, the magnetic-labeled bodies are always trapped on the inner wall of the small tube at the central portion of the magnetic pole piece and there will be no variation in the intensity of scattered light.

Further, in order to efficiently perform concentration and driving of magnetic field, it is preferred that two electromagnetic coils of the electromagnet pair are provided with electric current circuit and magnetic circuit as in this example to enable selection between independent excitation and dependent excitation The scattered light from the specimen is received by a photomultiplier 225. The output from the photomultiplier 225 is fed to an electronic circuit system 226, which detects scattered light in synchronization with the intermittent poulses selectively, and repeatedly add and make an average of the scattered light signals. By so doing, detection of magnetic-labeled body in a very small amount in the order of picogram is possible.

EXAMPLE 17

Figure 32:
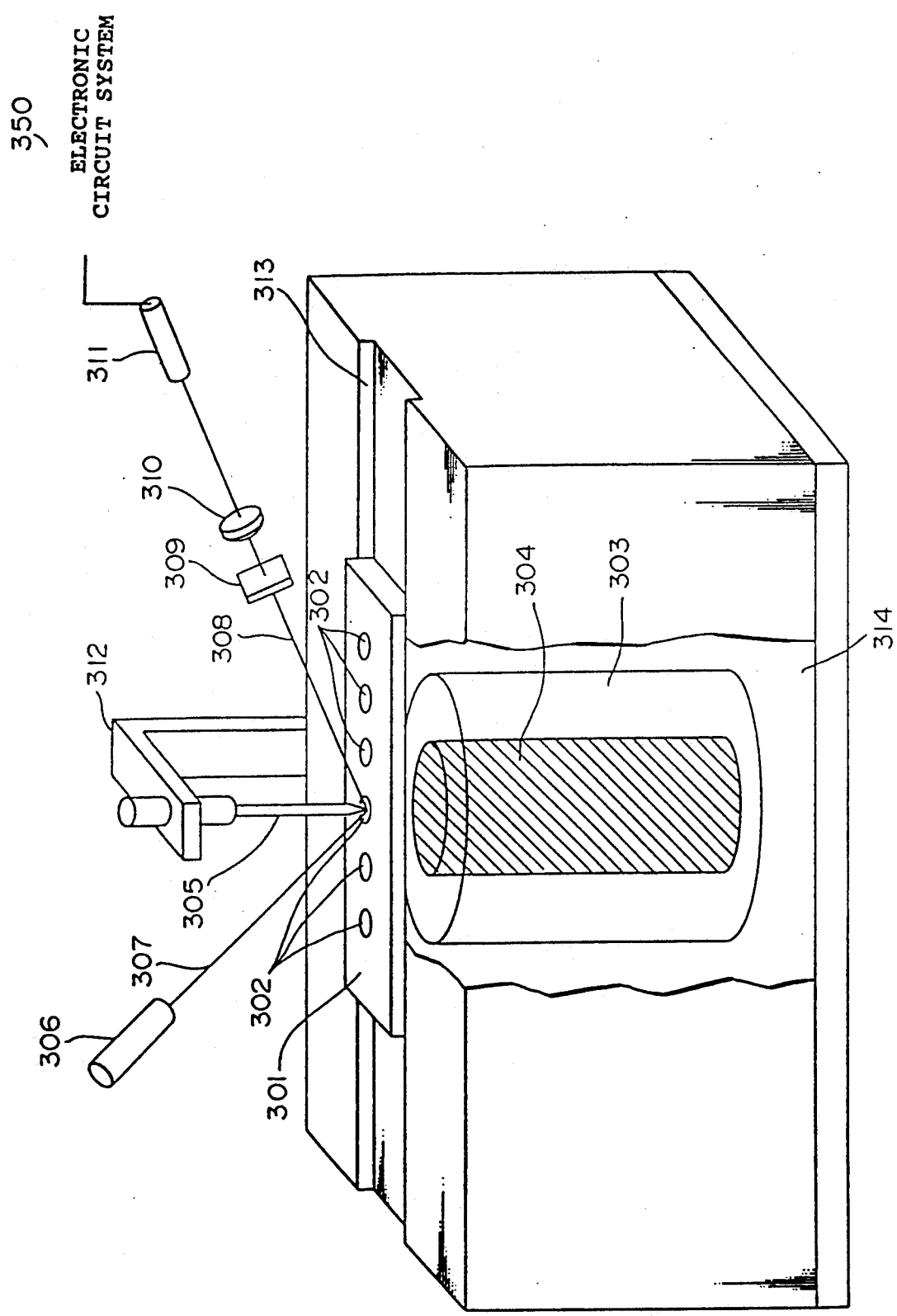
FIG. 32 is a schematical view illustrating the construction of a laser magnetic immunoassay apparatus according to one example of the present invention in which scattered light is measured.

FIG. 32 is a schematical view of a laser magnetic immunoassay apparatus which illustrates an example of the present invention.

301 is a specimen container, 302 is a specimen storage portion of the specimen container, 302 is an electromagnet, 304 is a core of the electromagnet, 305 is a magnet pole piece, 306 is a laser beam source, 307 is an incident laser beam axis, 308 is a scattered light detection axis, 309 is a slit, 310 is a condensing lens, 311 is a photomultiplier, 312 is a holding member for holding the magnetic pole piece, 313 is a guide groove for displacement of the specimen container, 314 is a support base for supporting the electromagnet, and 350 is an electronic circuit system.

The specimen storage portion 302 of the specimen container 301 opens upward, and the specimen storage portion 302 stores for example magnetic-labeled specimen after an antigen-antibody reaction. The specimen container 301 and the method of preparing specimens are preferably those described in Example 15. Since the specimen container 301 can move in one direction on a horizontal plane along the guide groove 313 and since measurement of a plurality of specimens can be made in the same container continuously.

The electromagnet core 304 and the magnetic pole piece 305 are made of preferably high permeability material which has low residual magnetization, and for example, pure iron with high purity or permaloy alloy is recommended. It is indispensable that the diameter of the electromagnet core 304 is sufficiently larger than the aperture of the specimen storage portion 302 of the specimen container 301, and the diameter of the magnetic pole piece 305 is sufficiently smaller than the aperture of the specimen storage portion 302 of the specimen container 301. For example, when the aperture of the specimen storage portion 302 is 10 mm, the diameter of the core 304 and that of the magnetic pole piece 305 are 50 mm and 5 mm, respectively. Further, the magnetic pole piece 305 preferably has a sharp end on the side facing the core 304. The magnetic pole piece 305 is fastened to a holding member 312 for holding magnetic pole piece with a screw so that the gap between the magnetic pole piece and the specimen container 301 can be adjusted. In the case of measurement of scattered light, an incident laser beam axis 308 and a scattered light detection axis 308 are set up at angles of 30° and 45°, respectively, with respect to the water surface of the specimen container 301. The slit 309 and the condensing lens 310 are used to guide only scattered light from specimens concentrated just below the magnetic pole piece 305. The slit 309, the lens 310 and a photomultiplier 311 constitute a light receiving system for receiving scattered laser beam. The scattered light detection axis 308 is set up so that reflected light of the radiated laser beam from the water surface can be avoided, and it is preferred that the angle of the incident laser beam axis 307 is smaller than that of the scattered light detection axis 308. The electronic circuit system 350 is to process the output from the photomultiplier 311.

Figure 33:
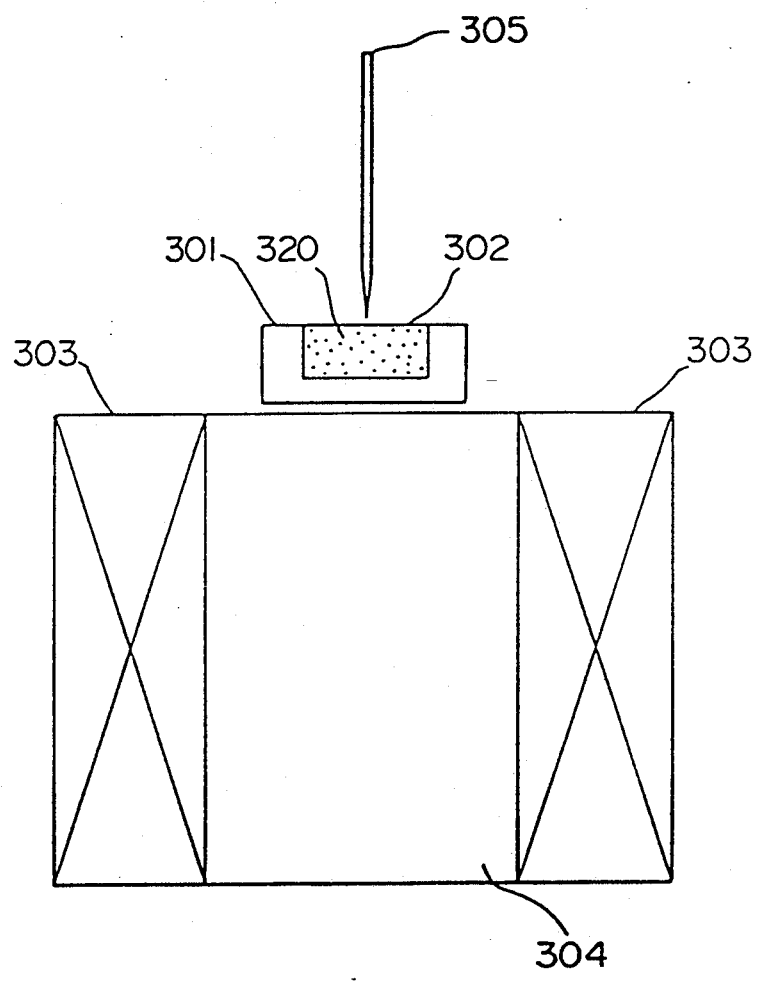
FIGS. 33 (a) to 33(d) are illustrations of the principle of operation of the laser magnetic immunoassay apparatus of the present invention, in which FIG. 33 (a) shows a state immediately after introduction of a specimen prepared into a specimen storage portion, FIG. 33 (b) illustrates a state where electromagnets are connected to a a direct current power source and are excited with direct current, FIG. 33 (c) shows a state where electromagnets are connected to intermittent pulsate power source and excited therewith, and FIG. 33(d) schematically indicates the state of dispersion of magnetic-labeled body-specimen complex under non-excited conditions.
Figure 33:
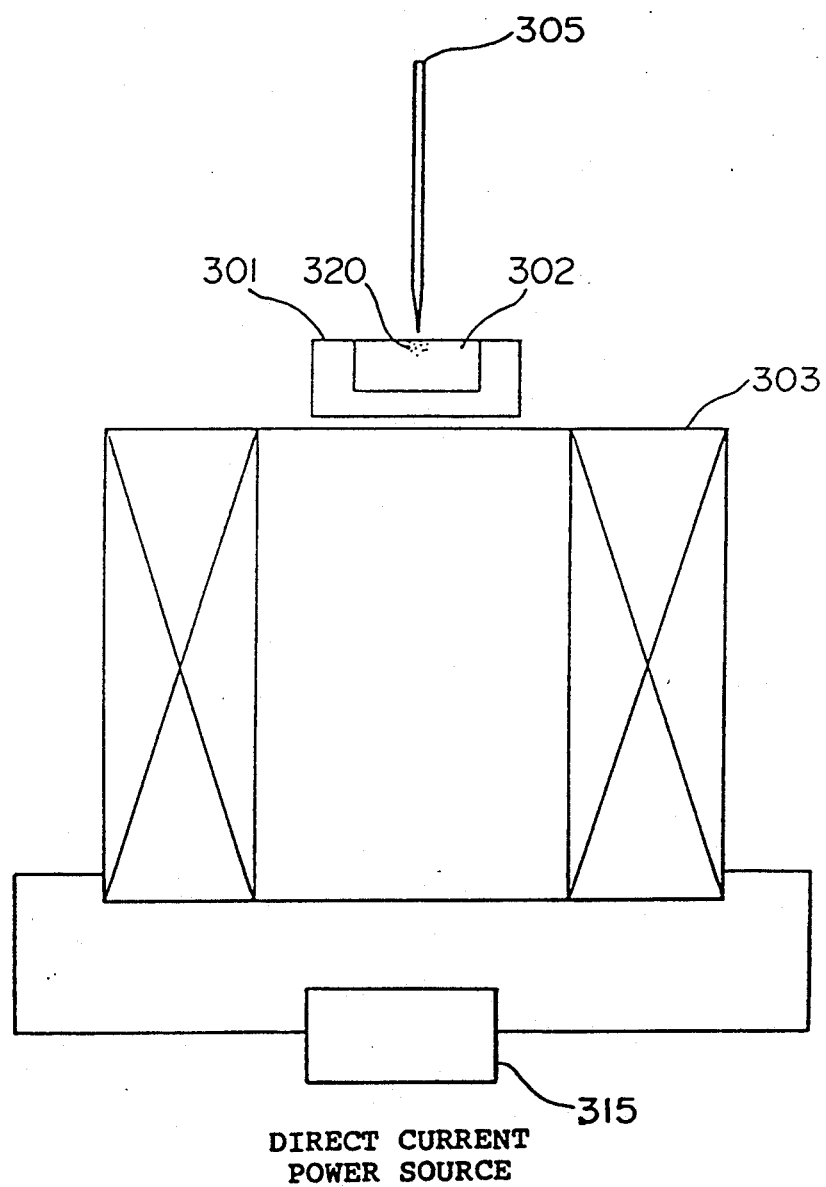
Figure 33:
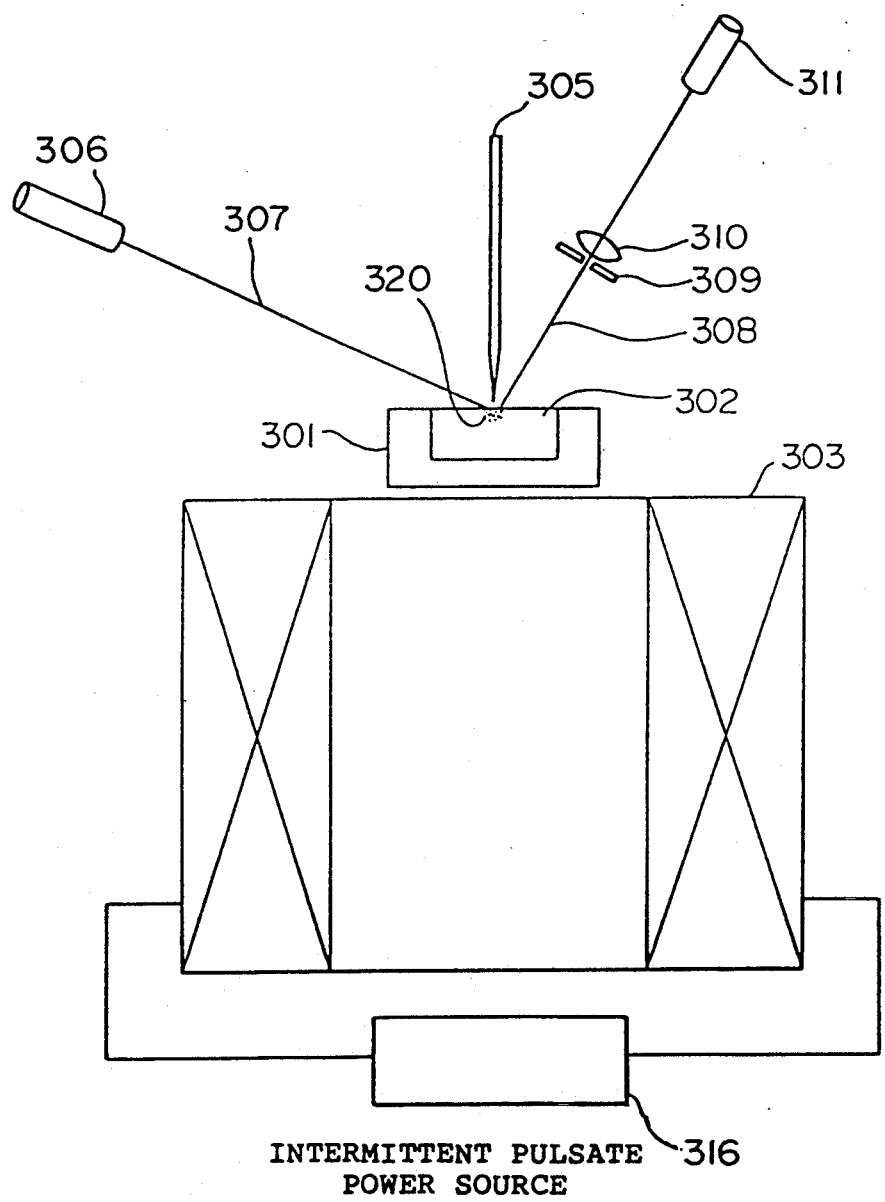
Figure 33:
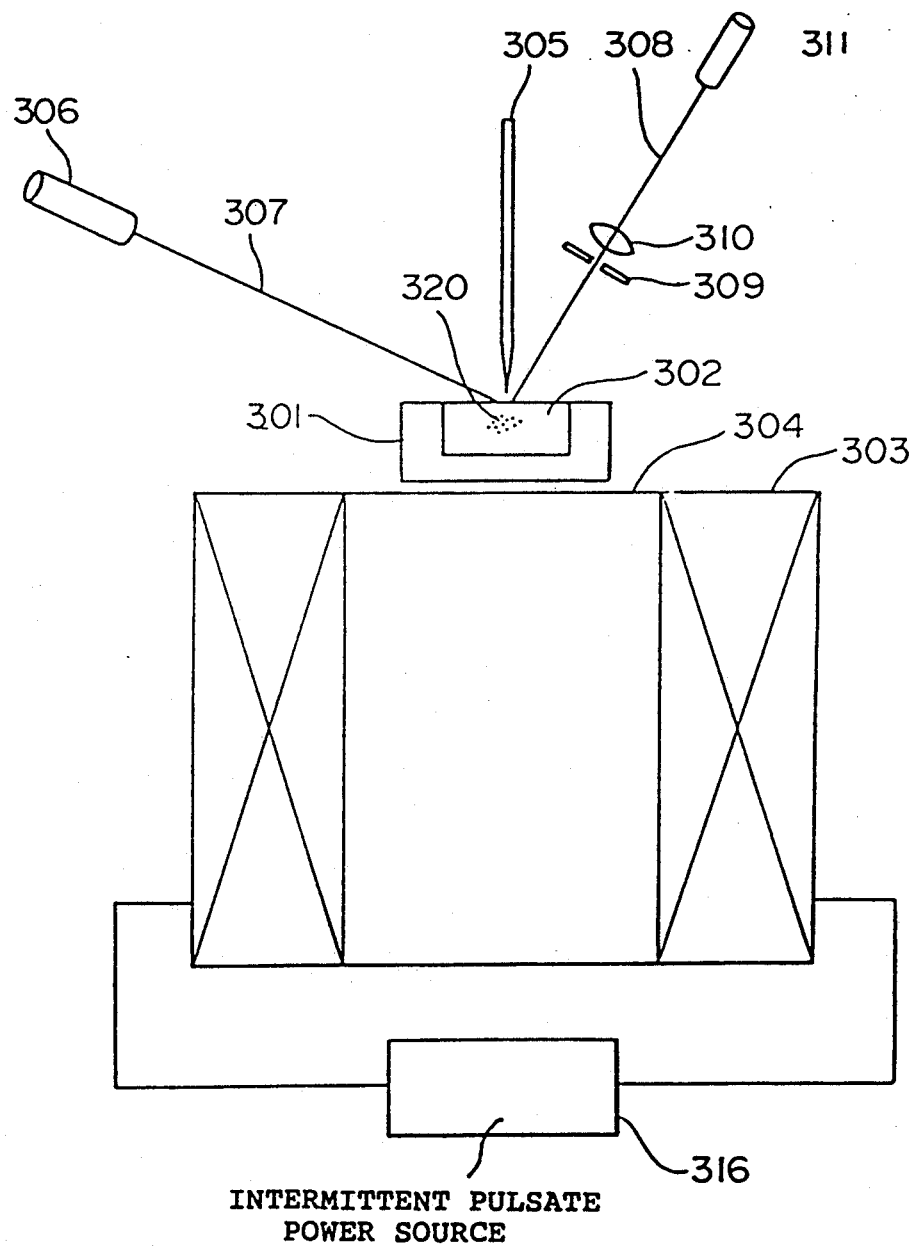

FIG. 33 is a drawing illustrating the principle of operation in the case of measurement of scattered light with the apparatus of the present invention, in which 315 is a direct current power source, 316 is an intermittent pulse power source, and 320 is a magnetic-labeled body. FIG. 33 schematically shows the state of dispersion of the magnetic-labeled body in (a) a state just after the adjusted specimen has been introduced into the specimen storage portion 302, (b) a state in which the electromagnet 303 is connected to the direct current power source 315 and excited with direct current, (c) a state in which the electromagnet 303 is connected to the intermittent pulse power source and excited therewith, and (d) a state in which the magnetic-labeled specimen is under non-excited conditions.

In the step of FIG. 33 (a), the electromagnet 303 is non-excited and therefore the specimen distributes uniformly in the container. In the step of FIG. 33 (b), since magnetic field concentrates on the magnetic pole piece 305 placed just above the specimen container 301, the magnetic-labeled specimen 320 is concentrated on the water surface just below the magnetic pole piece 305. As the result, The sharper the apex of the magnetic pole piece 305 the more localized the concentration. The steps of FIGS. 33 (c) and (d) are steps to excite the specimen concentrated just below the magnetic pole piece 305 with intermittent pulses and detect the scattered laser beam from the specimen. When the related pulse power source 316 is switched to non-excitation state, the concentrated specimen is dispersed in the solution due to Brownian movement. Therefore, periodical intermittent excitation of the electromagnet 303 results in periodical repetition of concentration and diffusion of the specimen in synchronization with the period of excitation. In order to cause speedy diffusion to occur in the non-excitation state, it is important that the core 304 of the electromagnet 303 and the magnetic pole piece 305 have not residual magnetization. Since diffusion of the specimen occurs mainly toward downwards due to the action of gravity, it had better set up the incident laser beam axis 307 at low angle as described above and radiate only an area of the specimen storage portion 302 near the water surface in order to increase variation in the intensity of scattered light.

In this apparatus, the magnetic-labeled specimen after concentration is driven periodically as described above, and the scattered light from the specimen is received by the photomultiplier 311. The output from the photomultiplier 311 is fed to the electronic circuit system 350, which selectively detects only that scattered light which is in synchronization with the intermittent pulse and repeatedly adds and makes an average of the scattered light signals. Detection of scattered light from the specimen can be performed with advantageously avoiding influences of disturbances from outside or background with repeatedly accumulate components of variation synchronized with the frequency of the intermittent pulses. The intermittent pulse frequency is suitably in the range of from 0.05 Hz to 20 Hz. With not higher than 0.05 Hz, it takes a long time for measurement, and with not lower than 20 Hz, the specimen does not follow. The pulse has a peak value smaller than direct current excitation current value, and it is preferred that DC off-set is absent. Thus, with this apparatus, the magnetic-labeled specimen in a minute amount in the order of picogram can be detected.

In the above-described example, although the specimen container 301 is constructed such that it can move in a horizontal plane, it can be constructed such that despite the above-described construction, the electromagnet and magnetic pole piece can be moved relatively with respect to the specimen container in a horizontal plane.

The laser magnetic immunoassay apparatus of the present invention is constructed to use an electromagnet and a magnetic pole piece opposing the electromagnet, and therefore is of a simple construction and can generate a high gradient magnetic field locally. Therefore, the adjusted specimen after antigen-antibody reaction can be concentrated locally in a very short period of time. Further, since the specimen concentrated just below th edmagnetic pole piece moves up and down in intermittent pulse magnetic field, variation in the intensity of scattered light from the specimen can be increased by introducing a laser beam to the specimen at a low angle.

Also, upon measurement with scattered laser beam, sensitivity and repeatability of measurement can be improved remarkably by performing repeated addition and making an average of scattered light signals from the specimen in addition to the method of detecting scattered light synchronized with the period of the intermittent pulse. When selectively measuring scattered light synchronized with the intermittent pulses, removal of influences from outside, background scattering and the like can be performed very effectively, thus enabling further improvement of the sensitivity of detection.

In the case of measuring reflected light, the incident laser beam axis 307 and the reflected light detection axis 308 must be set up at the same angle with respect to the water surface of the above-described specimen container 301. In this example the angles $\theta$ are 45°. The slit 309 is used to guide only reflected light from the magnetic-labeled specimen concentrated just below the magnetic pole piece 305 to the light receptor 310.

Figure 34:
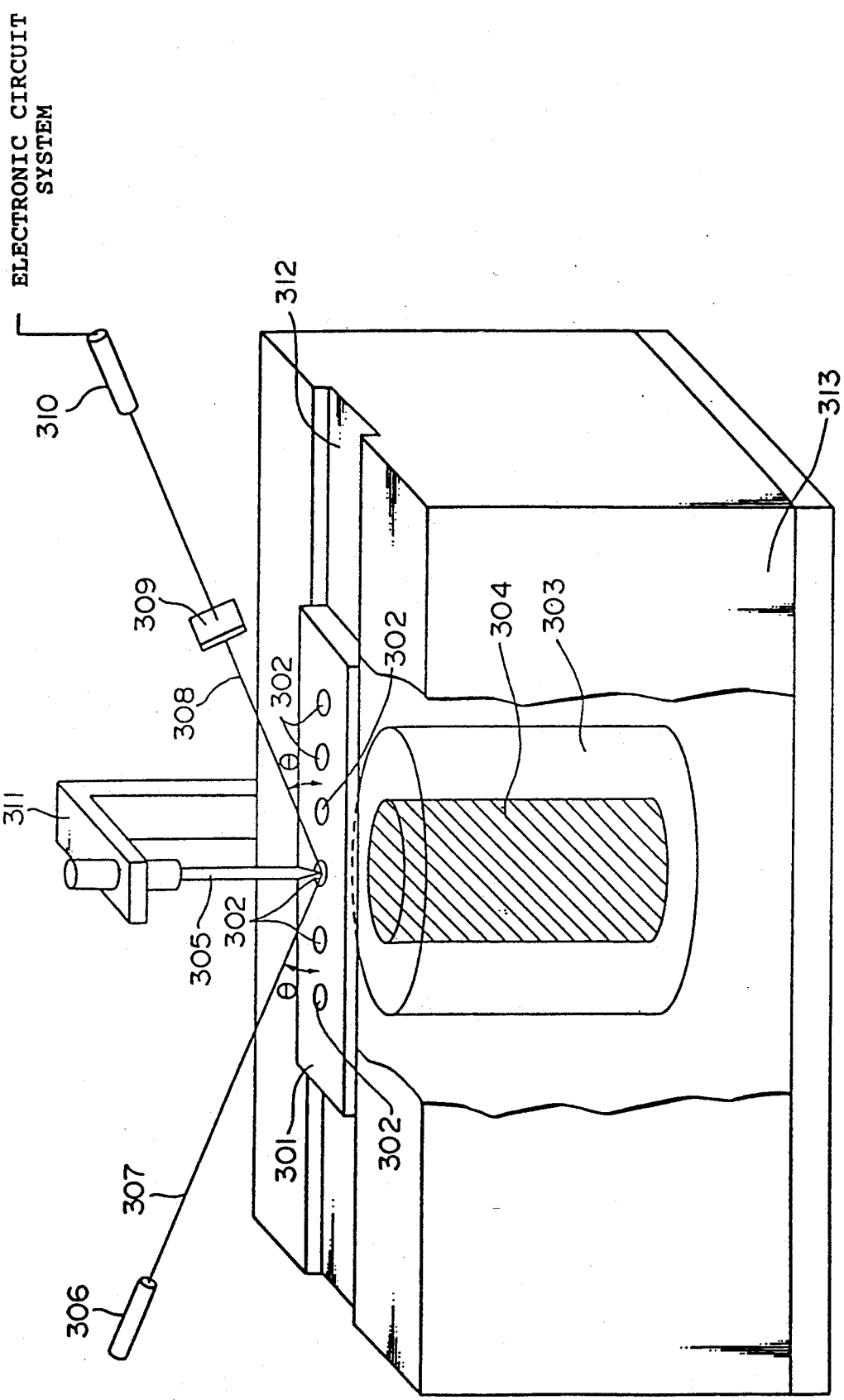
FIG. 34 is a schematical view of a laser magnetic immunoassay apparatus illustrating one example of the present invention in which reflected beams are measured.

FIG. 34 is a schematic view of a laser magnetic immunoassay apparatus illustrating one example in which the reflected beams are measured.

Figure 35:
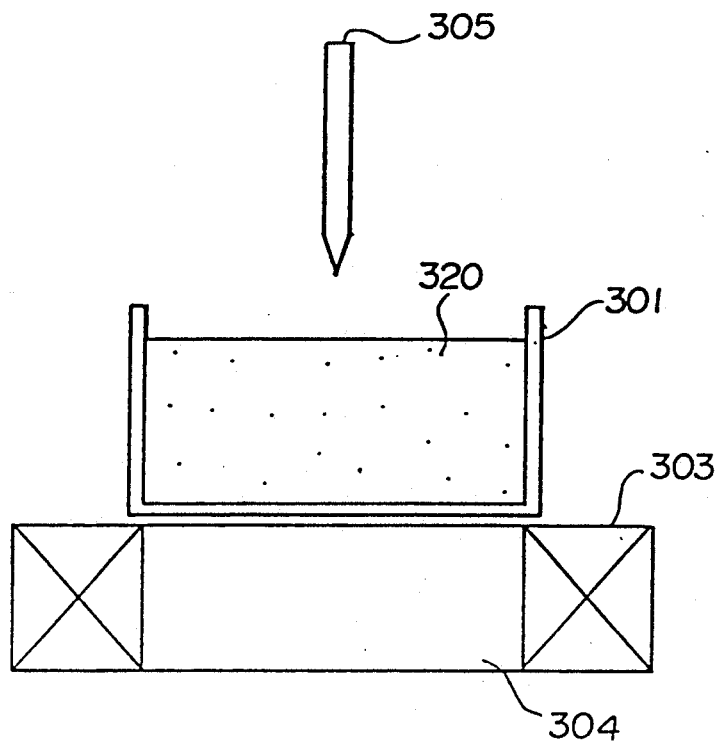
FIGS. 35 (a) to 35(d) are illustrations of the principle of operation of the laser magnetic immunoassay apparatus of the present invention, in which FIGS. 35 (b), 35(c) and 35(d) schematically illustrate the states of dispersion of magnetic-labeled body-specimen complex under the conditions where electromagnets are connected to a power source and excited with direct current, where electromagnets are energized strongly, and where electromagnets are energized weakly, respectively.
Figure 35:
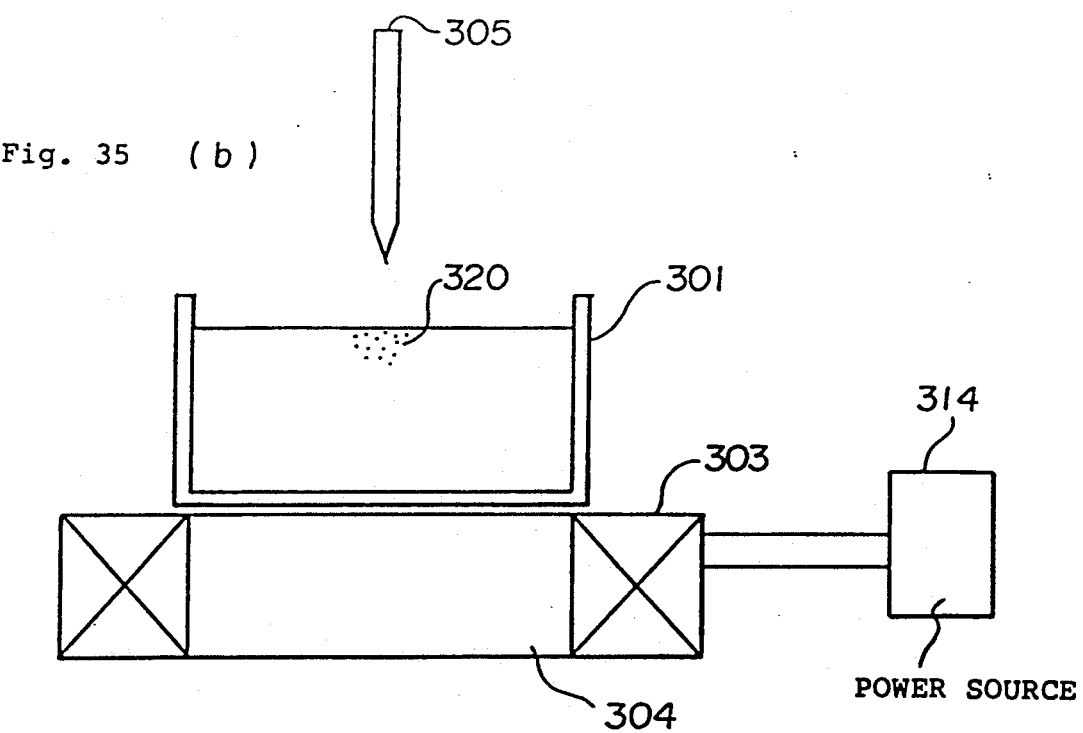
Figure 35:
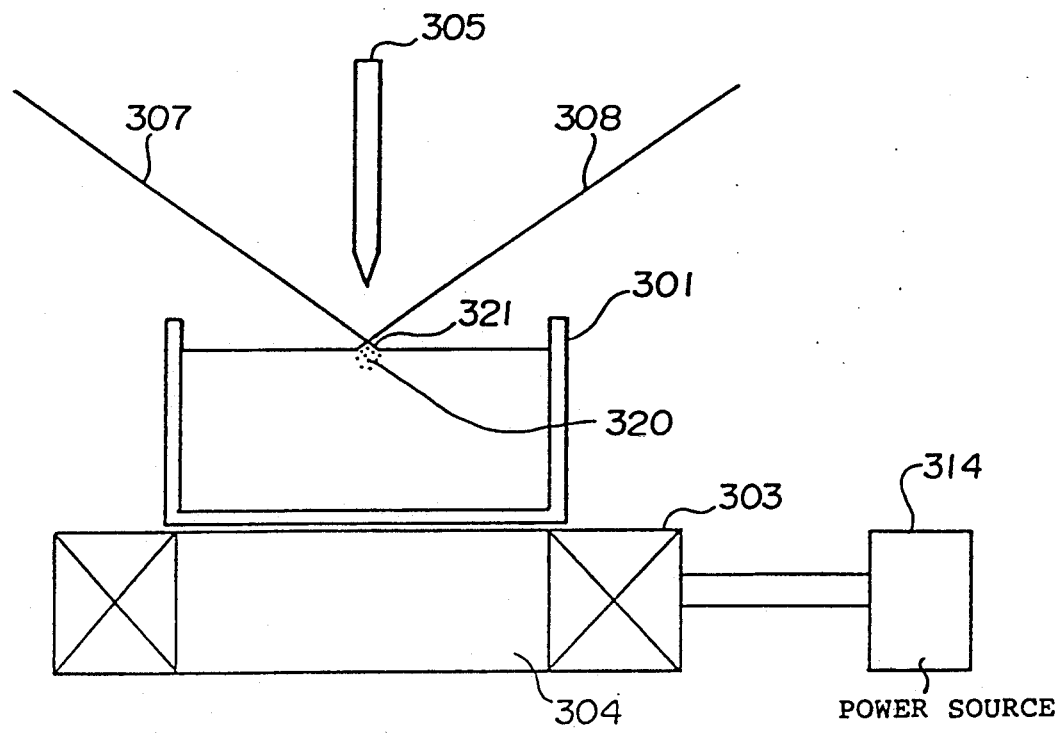
Figure 35:
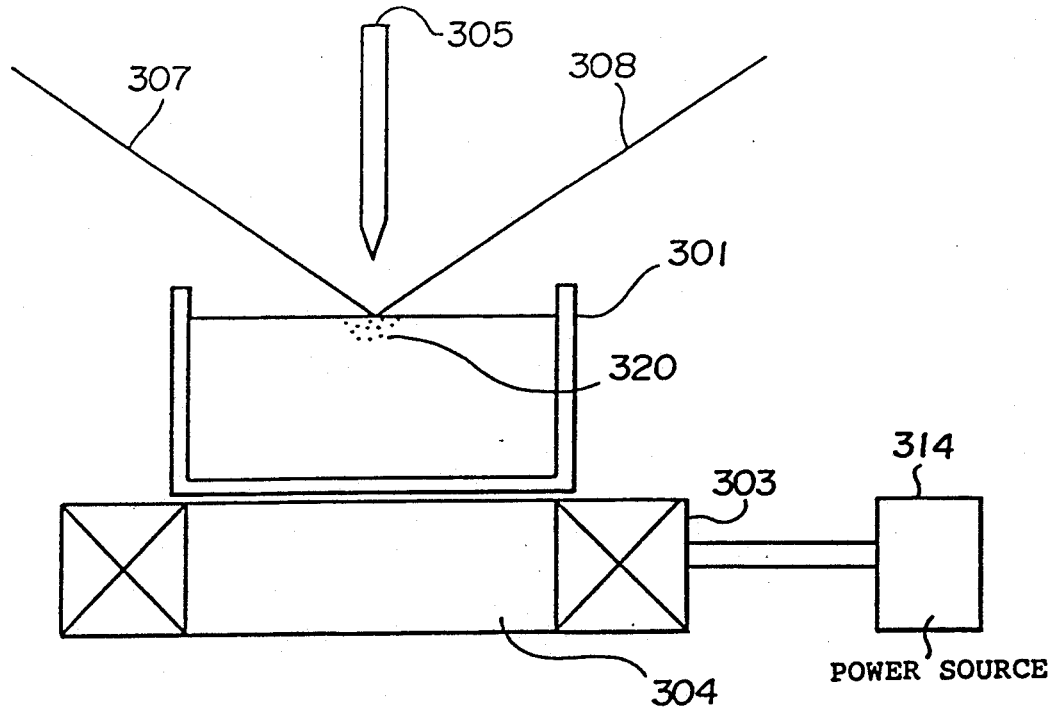

FIG. 35 is a drawing illustrating the principle of operation with the apparatus of the present invention, in which 314 is a power source for exciting the electromagnet 303, 320 is a magnetic-labeled body, and 321 is a raised portion of the water surface. FIG. 35 schematically shows the state of dispersion of the magnetic-labeled body in (a) a state just after the adjusted specimen has been introduced into the specimen storage portion 302, (b) a state in which the electromagnet 303 is connected to the power source 314 and excited with direct current, (c) a state in which the electromagnet magnet 303 is strongly excited, and (d) a state in which the electromagnet 303 is weakly excited. The power source 314 preferably outputs both direct current and alternating current. In this example, the power source 314 is constructed by a function generator and a current amplifier. The strong excitation and weak excitation are achieved by generating, for example, sine waves and corrugated waves or rectangular waves.

In the step of FIG. 35 (a), the electromagnet 303 is non-excited and therefore the specimen distributes uniformly in the container. In the step of FIG. 35 (b), since magnetic flux concentrates on the magnetic pole piece 305 placed just above the specimen container 301, the magnetic-labeled specimen 320 is concentrated on the water surface just below the magnetic pole piece 305. Therefore, it is preferred that the apex of the magnetic pole piece 305 is sharp. The steps of FIGS. 35 (c) and (d) are steps to excite the magnetic-labeled specimen 320 concentrated just below the magnetic pole piece 305 with alternating current and detect the reflected laser beam from the specimen 320. When the power source 314 is set in a strong excitation state, the magnetic-labeled specimen 320 is attracted strongly by the magnetic pole piece 305 and as the result the water surface around the magnetic-labeled body 320 is raised. When the power source 314 is set in a weak excitation state, the raised water surface becomes flat as the result of surface tension of water. Therefore, when the electromagnet 303 is excited with alternating current with current sufficient for raising the water surface, the reflected light from the water surface just below the magnetic pole piece 305 varies its intensity in synchronization with the period of excitation.

Figure 36:
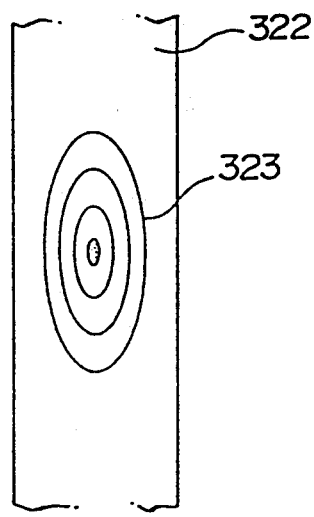
FIG. 36 illustrates interference fringe appearing in reflected beams.

FIG. 36 is a drawing illustrating interference fringes which will appear in reflected light when a white board is placed vertically in place of the light receptor 310 shown in FIG. 1, in which 322 is a reflected light flux, and 323 is interference fringe. Interference fringes appear in reflected light as shown in FIG. 36 when the height of raising is larger than $\frac{1}{2}$ of the wavelength of the laser beam used since the extent of raising of the water surface is proportional to the amount the magnetic-labeled specimen. Therefore, the amount of the magnetic-labeled specimen can be obtained from the number of the interference fringes.

Detection of reflected light from the specimen can be performed with advantageously avoiding influences of disturbances from outside or background with repeatedly accumulate components of variation synchronized with the the alternation frequency. The frequency is suitably in the range of from 0.05 Hz to 100 Hz. With not higher than 0.05 Hz, it takes a long time for measurement, and with not lower than 100 Hz, the specimen does not follow.

In this example, reflected light from themagnetic-labeled specimen 320 is received by the light receptor 310. The output of the light receptor 310 is fed to the electronic circuit system 350, which detects selectively reflected light synchronized with the period of excitation. By so doing, a very small amount of magnetic-labeled specimen can be detected.

As a result of detection of influenza virus labeled with micro-particles of a magnetic substance using the laser magnetic immunoassay apparatus of the present invention, it was confirmed that the method of the present invention enabled detection of virus in a population of about 10 in contrast to the conventional enzyme-immunoassay (EIA) in which detection was impossible unless virus was present in a population in the order of 100,000,000.

In the above-described example, although the specimen container 301 is constructed such that it can move in a horizontal plane, it can be constructed such that despite the above-described construction, the electromagnet and magnetic pole piece can be moved relatively with respect to the specimen container in a horizontal plane.

In the case of measuring reflected light, surface tension is exerted as righting force to the movement of the magnetic-labeled specimen against the attraction of the magnetic-labeled specimen by magnetic force, and therefore, the speed of response of this method has been improved at least ten times as high as that of the method in which the phenomenon of diffusion is used as righting force. Therefore, this method permits very efficient control of reflected light from the magnetic-labeled specimen, thus achieving with high speed a detection of an antigen-antibody reaction with ultrahigh sensitivity comparable to RIA method. Further, the micro-particles of a magnetic substance has no problem in respect of radioactivity or toxicity and those stable to specimens are available with ease.

EXAMPLE 18

Figure 37:
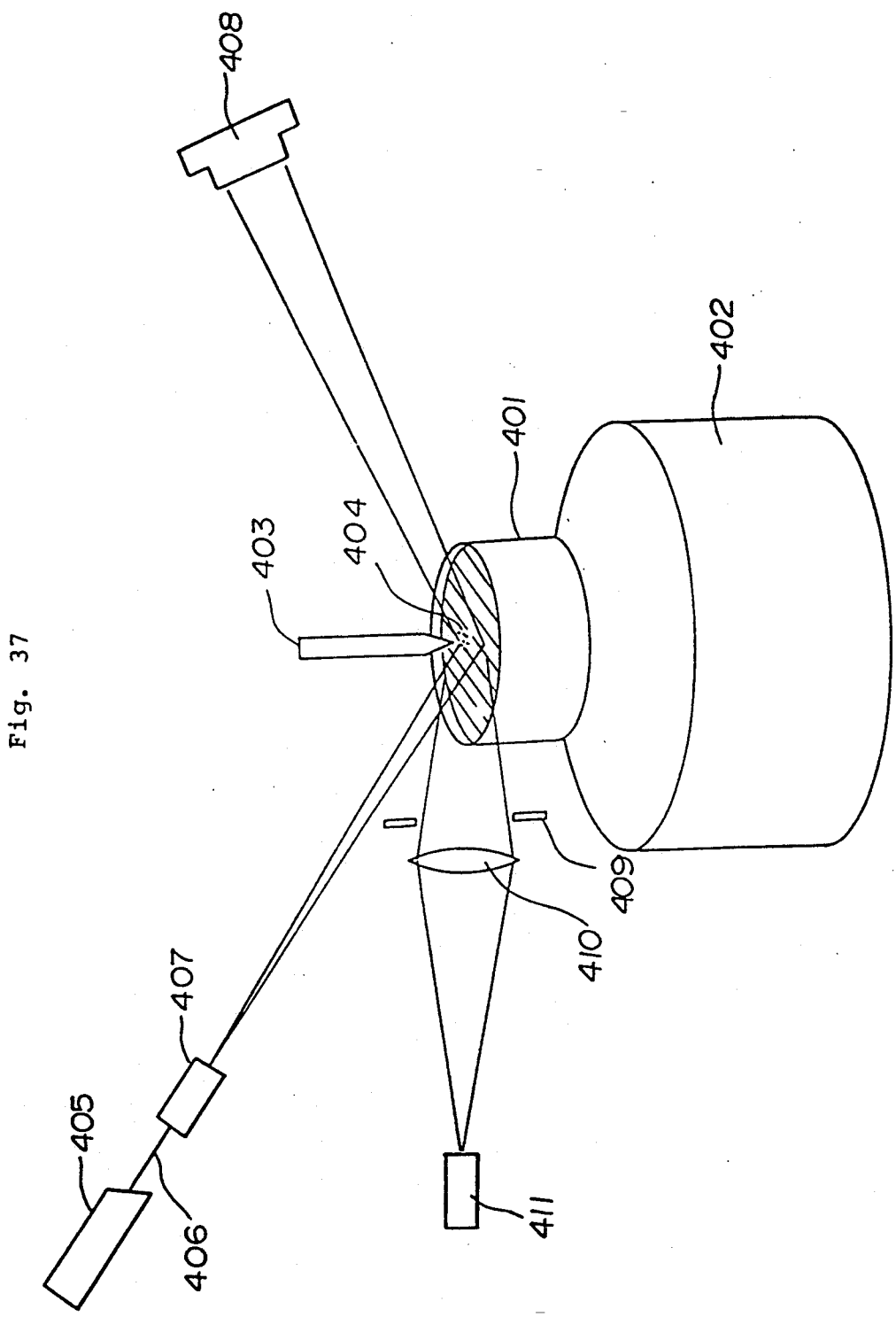
FIG. 37 is a schematical view of a laser magnetic immunoassay apparatus constructed so as to enable chronological radiation by scanning between concentration and non-concentration positions of a magnetic-labeled body-specimen complex to detect differential between respective signals from the two positions.

FIG. 37 is a schematical view of a laser magnetic immunoassay apparatus illustrating one example of the present invention.

A specimen container 401 having an upward opening is mounted horizontally on an electromagnet or permanent magnet 403 directly or through a stand. A magnetic pole piece 403 for guiding and concentrating a magnetic-labeled specimen is mounted just above the specimen container 401. A magnetic-labeled specimen 404 prepared in accordance with one of the above-described Preparation Methods I to V is stored in the specimen container 401. A laser beam source 405 and a deflector 407 for changing the direction of a laser beam 406 outgoing from the source 405 are arranged on one side with respect to the magnetic pole piece so that appropriate incident angle can be formed, and on the other side is arranged a photo diode 408 for detecting reflected light, interfered light or diffracted light. Further, at another position is arranged a light receiving system adapted for scattered light. The light receiving system comprises a slit 409, a condensing lens 410 and a photomultiplier 411. The scattered light receiving system is arranged so that it can receive outgoing light preferably at right angles to the incident light system.

The laser beam 406 from the laser beam source 405 enters the water surface of the specimen container 401 through the deflector 407 just below or near the magnetic pole piece 403 at an angle of 30° with respect to the liquid surface of the specimen container 401 and outgoes as scattered light, reflected light, interefered light or diffracted light in the region where the magnetic-labeled specimen which gathers near the water surface being attracted by th emagnetic pole piece 403, the outgoing light being detected with a photo diode 408 or a photomultiplier 411. In this case, the laser beam 406 is deflected by the deflector 407 to scan the liquid surface and radiate chronologically between the position of concentration where magnetic-labeled specimens gather thickly and the position of non-concentration where magnetic-labeled specimen is absent. The outgoing light signals from the position of concentration and from the position of non-concentration are detected by the photo diode 408 or the photomultiplier 411, respectively, and then differential between the signal from the position of concentration and that from the positio of non-concentration is detected by conventional means.

This example is excellent in followability and enables reduction in measurement time since the signals from the position of concentration and from the postion of non-concentration can be obtained without movement of the magnetic-labeled specimen in the liquid stored in the specimen container 401 and thus receiving no influence of viscous drag.

EXAMPLE 19

Figure 38:
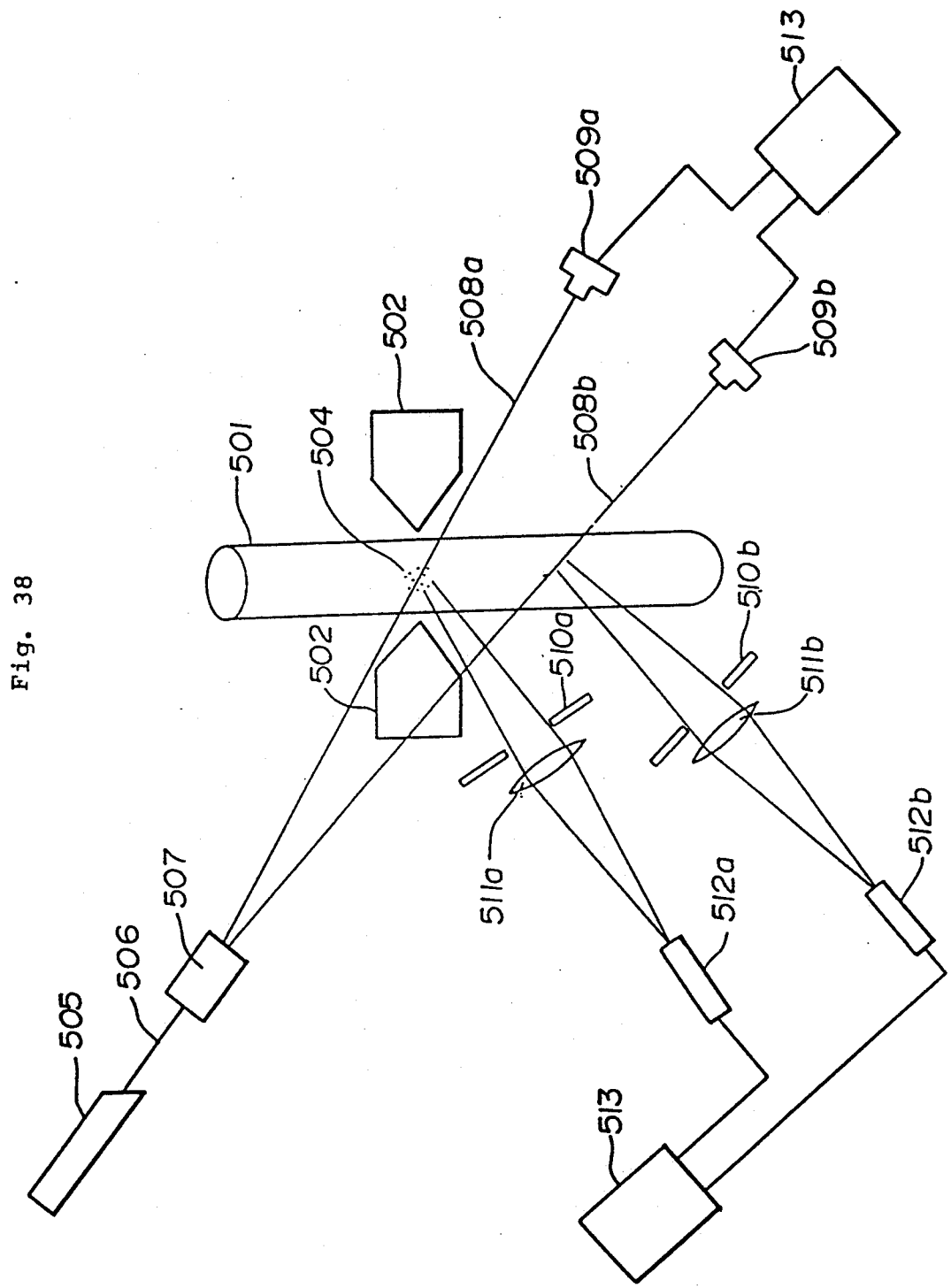
FIG. 38 is a schematical view of a laser magnetic immunoassay apparatus constructed so as to enable simultaneous radiation at concentration and non-concentration positions by bifurcating an incoming laser beam using a laser beam splitter in order to detect differential between respective signals from the two positions.

FIG. 38 is a schematical view illustrating another example of the present invention.

Sandwiching a cylingrical specimen container 501 made of glass arranged vertically are placed a pair of electromagnets or permanent magnets 502 which constitute a gradient magnet field generating apparatus 503. As for the apparatus, one having a construction as shown in FIG. 38 can be used. The specimen container 501 stores a magnetic-labeled specimen 504 prepared by one of the above-described Preparation Methods I to V, which is guided and concentrated by means of the gradient magnetic field generating apparatus. A laser beam source 505 and a beam splitter 507 for splitting a laser beam 506 outgoing from the laser beam source 505 are arranged on one side with respect to the specimen container so that appropriate incident angle can be obtained, and on the other side are arranged photo diodes 509a and 509b for detecting transmitted light or diffracted light corresponding to split laser beams 508a and 508b, respectively. Further, at another position are arranged two light receiving systems for receiving scattered lights comprising slits 510a and 510b, condensing lens 511a and 511b and photomultipliere 512a and 512b so that they correspond to the respective split beams. The scattered light receiving system is arranged such that it can receive scattered light at right angles to the incident light. The two photo diodes or photomultipliers are connected to electronic circuit 513 for processing the thus-obtained outgoing signals.

The laser beam 506 from the laser beam source 505 is split into two beams through the beam splitter 507 and enter the liquid containing the magnetic-labeled specimen through the wall of the specimen containers. It is preferred that incident light enters at right angles in the direction of the axis of the cylindrical specimen container 501. One of the split beams 508a outgoes as transmitted light or diffracted light through the position of concentration where the magnetic-labeled specimen which gathers near the maximum magnetic field point in the specimen container by being attracted by the gradient magnetic field generating apparatus while another split beam 508b outgoes through the position of non-concentration where no magnetic-labeled specimen is present. The outgoing lights are detected with photo diodes 509a and 509b. Further, when scattered light is measured, one of the split beams 508a is scattered at the position of concentration and the other split beam 508b is scattered at the position of non-concentration, and both outgo as scattering lights. The scattering lights are detected by the photo diodes 512a and 512b.

In this case, differential between the signal from the position of concentration and the signal from the position of non-concentration obtained by simultaneous radiation is detected by means of the electronic circuit.

In this example, since the signals from the position of concentration and those from the position of non-concentration can be obtained simultaneously, not only influences of disturbances from outside and background can be removed effectively but also remarkable reduction in measurement time is possible.

EXAMPLE 20

Figure 39:
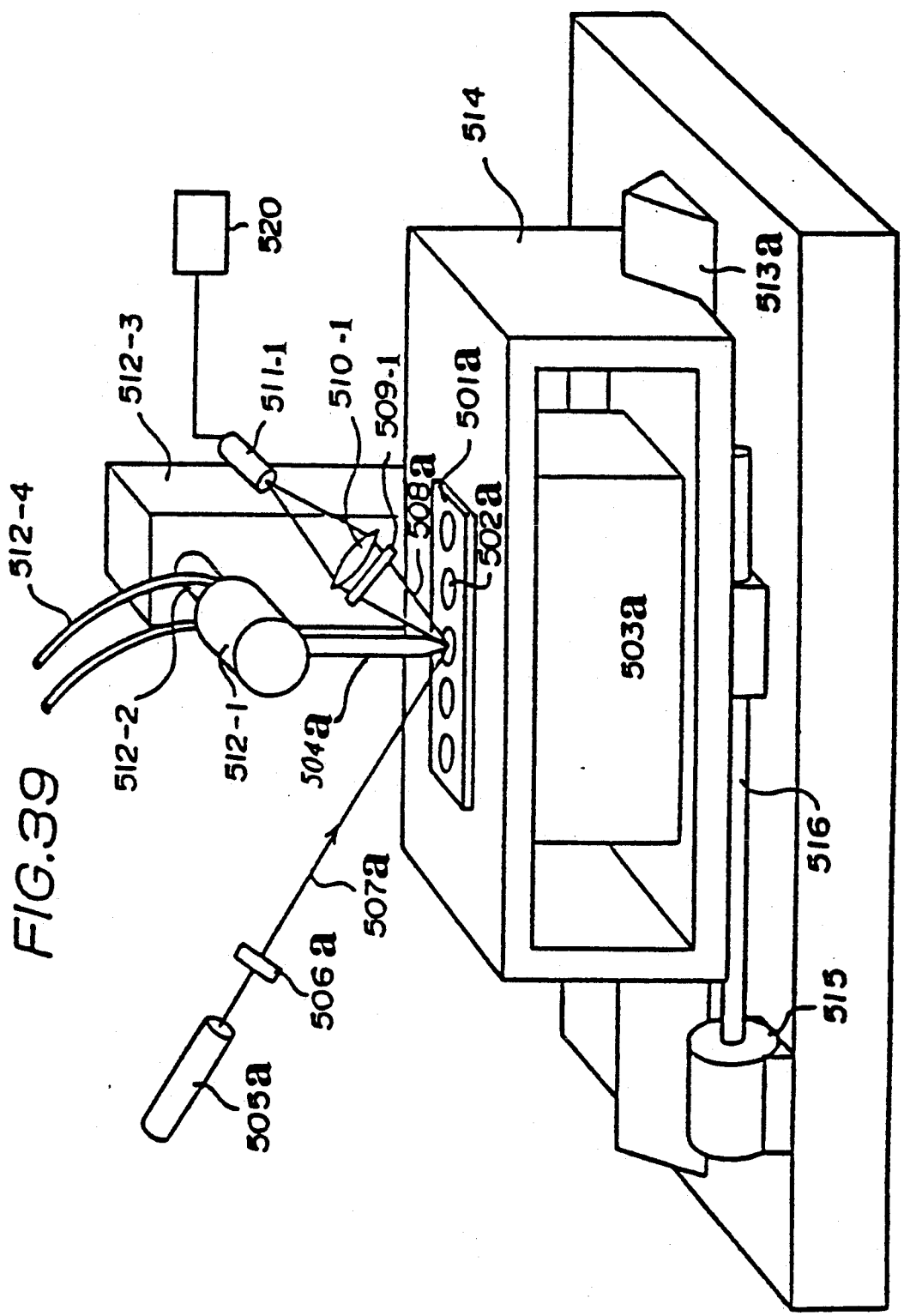
FIG. 39 is a schematical illustration of a laser magnetic immunoassay apparatus according to one example of the present invention which comprises a movement mechanism for moving a magnetic pole piece and that for moving a specimen container.

FIG. 39 is a schematical view of a laser magnetic immunoassay apparatus provided with a driving means for driving a magnetic pole piece and a driving means for driving a specimen container, which illustrates an example of the present invention.

501a is a specimen container, 502a is a specimen storage portion of the specimen container, 503a is a permanent magnet, 504a is a core of the electromagnet, 505a is a laser beam source, 506a is an ND filter, 507a is an incident laser beam axis, 508a is a scattered light detection axis, 509-1 is a slit, 510-1 is a condensing lens, 511-1 is a photomultiplier, 512 is a driving means for driving the magnet pole piece, 512-1 is a a hydraulic-type driving means, 512-2 is a supporting member, 512-3 is pole, 512-4 is a hydraulic tube, 513a is guide for displacement of the specimen container, 514 is a stand for supporting the magnet, and 520 is an electronic circuit system.

The specimen storage portion portion 502 of the specimen container 301 opens upward, and the specimen storage portion 302 stores, for example, magnetic-labeled specimen after an antigen-antibody reaction. The specimen container 501 and the method of preparing specimens are preferably those describd in Example 15. Since the specimen container 501 can slide in one direction on a horizontal plane along the guide groove 513 by being driven by a motor and a feed screw 516 and since measurement of a plurality of specimens can be performed in the same container continuously, a plurality of the specimens can be measured in the same container continuously.

The permanent magnet 503 and the magnetic pole piece 504 are the same as in Example 17. The magnetic pole piece 504 is fastened by screw to the hydraulic displacement means 512-1 of the magnetic pole piece displacement apparatus 512, and the gap between the magnetic pole piece 504 and the specimen 501 is adjustable. The displacement means 512-1 is supported by the spole 512-3 through the support member 512-2 and driven by means of hydraulic pressure transmitted by the hydraulic tube 512-4 so that the magnetic pole piece can be moved in the direction at right angles to the direction of the movement of the specimen container. In the case of measurement of scattered light, the incident laser beam axis 507 and the scattered light detection axis are set up at angles of 30° and 45°, respectively, with respect to the water surface of the specimen container 501. The slit 509 and the condensing lens 510 are used to guide only scattered light from specimens concentrated just below the magnetic pole piece 504. The slit 509, the lens 510 and a photomultiplier 511 constitute a light receiving system for receiving scattered laser beam. The scattered light detection axis 508 is set up so that reflected light of the radiated laser beam from the water surface can be avoided, and it is preferred that the angle of the incident laser beam axis 507 is smaller than that of the scattered light detection axis 508. The electronic circuit system 520 is to process the output from the photomultiplier 511.

In this apparatus, relative movement between the incident laser beam axis and the magnetic-labeled body-specimen complex by the movement of the magnetic pole piece while fixing the direction of the incident light axis of the laser beam to cause the movement of the magnetic-labeled body-specimen complex placed in a constant magnetic field following the movement of the magnetic pole piece, the incident laser beam radiates in a moment the position of concentration where the magnetic-labeled body-specimen complex is locally concentrated and in another moment the position of non-concentration where the magnetic-labeled body-specimen complex is absent, and outgoing light from the position of concentration and outgoing light from the position of non-concentration are chronologically received by the above-described light receiving system followed by processing the lights by the electronic circuit system 520 to obtain differential between the two outgoing lights.

Although description has been made with a stress layed on the displacement means for the magnetic pole piece in this example, it is of course possible to adopt what is described in the above-described example with respect to other members.

According to this example, the sensitivity of measurement was further improved.

EXAMPLE 21

FIG. 40 is a drawing which illustrates a method of immobilization according to one example of the present invention.

601 is a silicon wafer, 601' is a silicon chip, 602 is a Novolak resin film, 603 is a container, 604 is a PBS solution containing inactivated influenza virus, and 605 is inactivated influenza virus. On the surface of the silicon wafer which is 3 inch in diameter, 0.3 mm thick, was formed the Novolak resin film 2 by spin-coating a 20% ethanol solution of the Novolak resin at a rotation number of 3,000 rpm for 1 minute. After coating and drying, the wafer was cut into chips of 5 mm each side using a dicing saw, and the chips were dipped in the PBS solution containing inactivated influenza virus for one night to immobilize the influenza virus on the Novolak resin film. Influenza virus was also immobilized on another resin film, i.e., resin M film in the same manner as above.

Figure 41A:
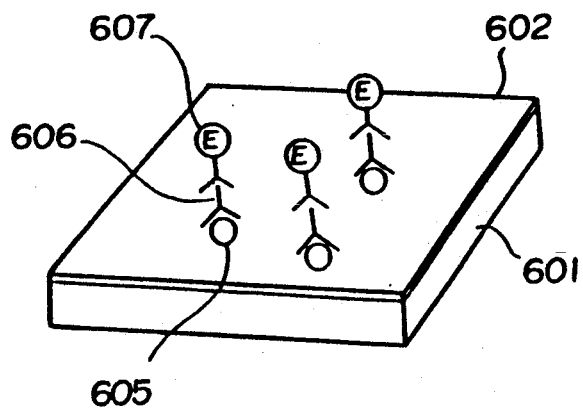
FIGS. 41(a) to 41(c) show a test sample and comparative test sample immobilized according to the method illustrated in FIGS. 40(a) to 40(e).
Figure 41B:
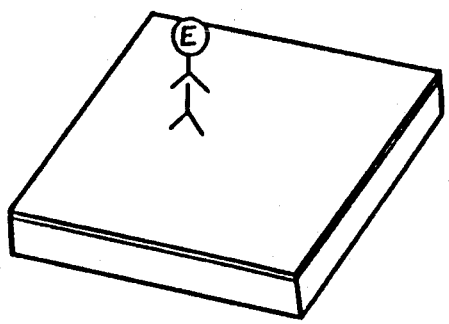
Figure 41C:
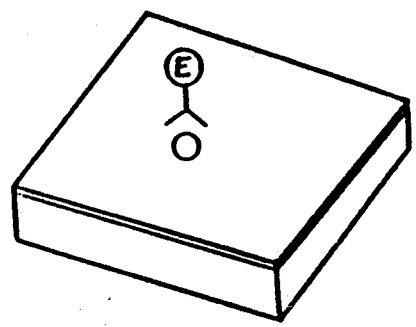

FIG. 41 shows a test piece used for confirming effectiveness of the immobilization method of the present invention, and Table 1 indicates the examination results.

606 is anti-viral antibody to the immobilized influenza virus and 607 is an enzyme antibody. After subjecting the immobilized influenza virus and the anti-viral anti-body to antigen-antibody reaction and wasing, unused anti-viral anti-body was separated and removed, and then known enzyme antibody used in EIA was subjected to antigen-antibody reaction with the anti-viral antibody. Thereafter, unused enzyme antibody was washed out and further a substrate was added to obtain a test piece (a). For comparison, similar enzyme anti-body was labeled using chips after the step shown in FIG. 1 (c) without immobilization of the influenza virus to obtain control antibody (b) and control virus (c).

The control antibody (b) was washed out since no virus was present on the immobilization film. On the other hand, the control virus (c) was removed with ease by washing since influenza virus was not attached to the immobilization film in a short period of time.

Table 1 shows measurement results for the test piece (a), control antibody (b) and control virus (c).

TABLE 1

| | Novolak Resin | Resin M |
|---|---|---|
| Test Piece (a) of Present Invention | 0.34 | 0.17 |
| Control Antibody (b) | 0.09 | 0.13 |
| Control virus (c) | 0.08 | 0.07 |

It is clear when the Novolak resin is used as the immobilization film, the EIA value of the test piece was higher than the resin M, and it was lower than the control antibody and the control virus. Therefore, in the case of influenza virus, effectiveness of the present example using the Novolak resin was confirmed.

The method of immobilization is not limited to the above-described examples but the present invention can be applied to the above-described micro-particles of the nonmagnetic substance, plastic resin and glass in addition to silicon wafers as support. Further, it is also applicable to various organic and inorganic resist materials which can be used in photo resist step of production of semiconductors such as AZ in addition to Novolak resin as the immobilization film.

INDUSTRIAL APPLICABILITY

The measurement method and apparatus of the present invention are particularly suited for high sensitivity test of antigen-antibody reaction. Although virus such as influenza virus is described indetail in examples of the present invention, it is clear that the invention is also applicable as it is to immunological diagnosis of cancers. That is, it is known that changes for specifically recognizing cancer cells appear in lymphocytes in blood and the lymphocytes gather densely around the cancer cells due to immunological guard mechanism of human body even in the case of diseases such as stomach cancer where cancer cells are not released in blood. Known cell electrophoresis utilizes the phenomenon that macrophages and leucocytes gather toward cancer cells and makes diagnosis of cancers, as described in, for example, Cancer Research vol. 30, pages 2265-2270 and American Review of Respiratory Diseases, vol. 111, pages 566-569 to which the present inventors contributed. Taking all these into consideration, immunological diagnosis of cancers can be performed in early stages as in the case of virus by using a method in which lymphocytes of a patient are labeled with micro-particles of a magnetic substance of the present invention instead of the antibody described in examples of the present invention.

Further, since the laser magnetic immunoassay method and apparatus of the present invention are suited for automatization of antigen-antibody reaction tests, they exhibit particular effects if they are used in screening tests and close examinations of various viruses, cancers and the like which are necessary in group examination. In addition, to antigen-antibody reaction, application is made to measurement of various hormons such as peptide hormons or various enzymes, vitamins, medicines and the like to which RIA method has heretofore been applied. As stated above, the method of the present invention can be put to use in early diagnosis and therapy of patients, and thus makes a great contribution to the field of medical treatment.

Further, the measurement method and apparatus of the present invention have a very high detection sensitivity, they provide new effective research techniques in the field of immunology and molecular biology.

What is claimed is:

1. A laser magnetic immunoassay method comprising:
   (a) subjecting magnetic-labeled bodies to an immunoreaction with a specimen containing a target analyte to form magnetic-labeled immunocomplexes, wherein each of said magnetic-labeled bodies consists essentially of an antigen or an antibody, which specifically binds to the target analyte, attached to a microparticle of a magnetic substance;
   (b) collecting, separating and removing unreacted magnetic-labeled bodies from said magnetic-labeled immunocomplexes;
   (c) dispersing said magnetic-labeled immunocomplexes in a liquid contained in a specimen container having an upward opening;
   (d) applying an oscillating magnetic field to said liquid using an electromagnet and a magnetic pole piece so as to periodically concentrate said magnetic-labeled immunocomplexes to a predetermined position of concentration immediately below the surface of the liquid, wherein a core of said electromagnet is positioned below the container and an end of said magnetic pole piece is positioned immediately above the surface of the liquid;
   (e) radiating a laser beam on said predetermined position of concentration;
   (f) detecting and measuring reflected light from said predetermined position when said magnetic-labeled immunocomplexes are concentrated in said predetermined position so as to determine a quantity of said target analyte, said detecting and measuring being in synchronization with the oscillating magnetic field.

2. The laser magnetic immunoassay method as claimed in claim 1, wherein the quantity of target analyte is determined by detecting interference fringes in the reflected light resulting from the attraction of the magnetic-labeled immunocomplexes to said magnetic pole piece which causes a rise in the liquid surface at the predetermined position of concentration.

3. A laser magnetic immunoassay apparatus for quantitatively determining a target analyte in a specimen, said apparatus comprising:
   (a) a specimen container having an upward opening and containing a liquid for storing magnetic-labeled immunocomplexes, the immunocomplexes being formed from an immunoreaction between the specimen containing the target analyte and magnetic-labeled bodies, wherein each of the magnetic-labelled bodies consists essentially of an antigen or an antibody, which specifically binds to the target analyte, attached to a microparticle of a magnetic substance;
   (b) an electromagnet, wherein a core of said electromagnet is positioned below said container;
   (c) a magnetic pole piece, wherein an end of said pole piece is positioned immediately above the surface of said liquid;
   (d) a power source for exciting said electromagnet so as to create an oscillating magnetic field which periodically concentrates the magnetic-labeled immunocomplexes to a predetermined position of concentration immediately below the surface of the liquid;
   (e) a laser beam source for generating a laser beam;
   (f) an incident optical system constructed so as to radiate the laser beam on said predetermined position of concentration;
   (g) a light receiving system for receiving reflected light from said predetermined position;
   (h) detecting and measuring means associated with said light receiving system and said power source for detecting and measuring reflected light from said predetermined position when said magnetic-labeled immunocomplexes are concentrated in said predetermined position so as to determine a quantity of said target analyte, said detecting and measuring being in synchronization with the oscillating magnetic field.

4. The laser magnetic immunoassay apparatus as claimed in claim 3, wherein the core of the electromagnet and the magnetic pole piece are made of a high permeability material which has low residual magnetization, and wherein the end of the magnetic pole piece is pointed.

5. The laser magnetic immunoassay apparatus as claimed in claim 3, wherein the magnetic pole piece is constructed so as to be movable with respect to the specimen container.

6. The laser magnetic immunoassay apparatus as claimed in claim 3, wherein the specimen container, or the electromagnet and the magnetic pole piece, are constructed so as to be movable in a horizontal plane.

7. The laser magnetic immunoassay apparatus as claimed in claim 3, wherein said detecting and measuring means comprise an electronic circuit system for selectively detecting reflected light which is in synchronization with the oscillating magnetic field created by said power source.

* * * * *